United States Patent
Kipps et al.

(10) Patent No.: US 11,312,787 B2
(45) Date of Patent: *Apr. 26, 2022

(54) ANTIBODIES AND VACCINES FOR USE IN TREATING ROR1 CANCERS AND INHIBITING METASTASIS

(71) Applicant: The Regents of the University of California, Oakland, CA (US)

(72) Inventors: Thomas James Kipps, San Diego, CA (US); Jian Yu, San Diego, CA (US); Bing Cui, San Diego, CA (US); Liguang Chen, San Diego, CA (US); George F. Widhopf, II, San Diego, CA (US); Charles Prussak, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/412,202

(22) Filed: May 14, 2019

(65) Prior Publication Data

US 2019/0389962 A1 Dec. 26, 2019

Related U.S. Application Data

(63) Continuation of application No. 15/619,119, filed on Jun. 9, 2017, now Pat. No. 10,344,096, which is a continuation of application No. 14/422,519, filed as application No. PCT/US2013/032572 on Mar. 15, 2013, now Pat. No. 9,758,591.

(60) Provisional application No. 61/709,803, filed on Oct. 4, 2012, provisional application No. 61/709,055, filed on Oct. 2, 2012, provisional application No. 61/693,230, filed on Aug. 24, 2012.

(51) Int. Cl.
| | |
|---|---|
| A61K 39/00 | (2006.01) |
| C07K 16/30 | (2006.01) |
| C07K 16/28 | (2006.01) |
| C07K 14/435 | (2006.01) |

(52) U.S. Cl.
CPC ...... C07K 16/30 (2013.01); A61K 39/001102 (2018.08); C07K 14/435 (2013.01); C07K 16/2803 (2013.01); C07K 16/3015 (2013.01); A61K 2039/505 (2013.01); A61K 2039/6081 (2013.01); C07K 2317/34 (2013.01); C07K 2317/73 (2013.01); C07K 2317/92 (2013.01); C07K 2317/94 (2013.01)

(58) Field of Classification Search
CPC .......... C07K 16/30; C07K 14/435; A61K 39/001102; A61K 2039/505; A61K 39/39558; A61P 35/00

See application file for complete search history.

(56) References Cited

U.S. PATENT DOCUMENTS

| | | | |
|---|---|---|---|
| 5,219,837 A | 6/1993 | Cohen et al. |
| 5,843,749 A | 12/1998 | Maisonpierre et al. |
| 5,855,885 A | 1/1999 | Smith et al. |
| 5,858,725 A | 1/1999 | Crowe et al. |
| 5,985,279 A | 11/1999 | Waldmann et al. |
| 6,001,575 A | 12/1999 | Huganir et al. |
| 6,133,426 A | 10/2000 | Gonzalez et al. |
| 6,303,341 B1 | 10/2001 | Hiatt et al. |
| 6,586,251 B2 | 7/2003 | Economides et al. |
| 6,596,541 B2 | 7/2003 | Murphy et al. |
| 6,605,709 B1 | 8/2003 | Breton |
| 6,663,863 B2 | 12/2003 | Horvath et al. |
| 6,677,436 B1 | 1/2004 | Sato et al. |
| 6,703,018 B2 | 3/2004 | Jardieu et al. |
| 6,919,183 B2 | 7/2005 | Fandl et al. |
| 7,105,348 B2 | 9/2006 | Murphy et al. |
| 7,138,501 B2 | 11/2006 | Ruben et al. |
| 7,193,069 B2 | 3/2007 | Isogai et al. |
| 7,214,786 B2 | 5/2007 | Kovalic et al. |
| 7,223,393 B2 | 5/2007 | Landolfi et al. |
| 7,235,380 B1 | 6/2007 | Joliffe et al. |
| 7,244,430 B2 | 7/2007 | Throsby et al. |
| 7,314,974 B2 | 1/2008 | Cao et al. |
| 7,323,553 B2 | 1/2008 | Fahrner et al. |
| 7,332,582 B2 | 2/2008 | Hardy et al. |
| 7,381,801 B2 | 6/2008 | Renner et al. |
| 7,396,530 B2 | 7/2008 | Goffe |
| 7,427,399 B2 | 9/2008 | Jakobovits et al. |
| 7,429,382 B2 | 9/2008 | Albone et al. |
| 7,435,549 B1 | 10/2008 | Kufer et al. |
| 7,435,553 B2 | 10/2008 | Fandl et al. |
| 7,473,423 B2 | 1/2009 | Rodriguez et al. |
| 7,504,086 B2 | 3/2009 | Shiotsuka et al. |
| 7,524,498 B2 | 4/2009 | Hardy et al. |

(Continued)

FOREIGN PATENT DOCUMENTS

| | | |
|---|---|---|
| CA | 2 705 923 A1 | 5/2009 |
| CA | 2 734 645 A1 | 2/2010 |

(Continued)

OTHER PUBLICATIONS

Balmana, J. et al. (May 20, 2009). "BRCA in breast cancer: ESMO clinical recommendations," *Ann Oncol* 20 Suppl 4:19-20.

Baskar, S. et al. (Jan. 1, 2008). Targeting Human B Cell Chronic Lymphocytic Leukemia with a Monoclonal Antibody Specific for the receptor Tyrosine Kinane ROR1, *Journal of Immunotherapy* 31(9):969.

Brand, F.X. et al. (Jan.-Feb. 2006). "Prospect for anti-HER2 receptor therapy in breast cancer," *Anticancer Res* 26(1B):463-470.

Casset, F. et al. (Jul. 18, 2003). "A peptide mimetic of an anti-CD4 monoclonal antibody by rational design," *Biochem Biophys Res Commun* 307(1):198-205.

(Continued)

*Primary Examiner* — Sheela J. Huff
(74) *Attorney, Agent, or Firm* — Mintz, Levin, Cohn, Ferris, Glovsky and Popeo, P.C.

(57) ABSTRACT

The present invention relates to pharmaceutical compositions and a method of inhibiting metastasis using anti-ROR1 antibodies or antigen binding fragments, ROR1 binding peptides and ROR1 vaccines.

20 Claims, 63 Drawing Sheets

Specification includes a Sequence Listing.

(56) References Cited

U.S. PATENT DOCUMENTS

| | | |
|---|---|---|
| 7,534,604 B2 | 5/2009 | Fandl et al. |
| 7,544,790 B2 | 6/2009 | Joliffe et al. |
| 7,569,389 B2 | 8/2009 | Feldmann et al. |
| 7,604,800 B2 | 10/2009 | Lin et al. |
| 7,605,235 B2 | 10/2009 | Anderson et al. |
| 7,608,453 B2 | 10/2009 | Cattaneo et al. |
| 7,612,179 B2 | 11/2009 | Nordstedt et al. |
| 7,619,069 B2 | 11/2009 | Davies et al. |
| 7,625,561 B2 | 12/2009 | Finnern et al. |
| 7,700,098 B2 | 4/2010 | Ferlin et al. |
| 7,718,774 B2 | 5/2010 | Mather et al. |
| 7,736,647 B2 | 6/2010 | Boumsell et al. |
| 7,750,124 B2 | 7/2010 | Gurney et al. |
| 7,763,249 B2 | 7/2010 | Sugimura et al. |
| 7,807,160 B2 | 10/2010 | Presta et al. |
| 7,807,166 B2 | 10/2010 | Rodriguez et al. |
| 7,867,493 B2 | 1/2011 | Damiano et al. |
| 7,868,141 B2 | 1/2011 | Endl et al. |
| 7,910,100 B2 | 3/2011 | Stuhmer et al. |
| 7,919,089 B2 | 4/2011 | Kufer et al. |
| 7,960,515 B2 | 6/2011 | Min et al. |
| 7,968,687 B2 | 6/2011 | McDonagh et al. |
| 7,981,416 B2 | 7/2011 | Hardy et al. |
| 8,008,445 B2 | 8/2011 | Devy et al. |
| 8,043,839 B2 | 10/2011 | Weiner et al. |
| 8,062,635 B2 | 11/2011 | Hattori et al. |
| 8,067,671 B2 | 11/2011 | Boukharov et al. |
| 8,071,730 B2 | 12/2011 | Goetsch et al. |
| 8,075,885 B2 | 12/2011 | Bebbington et al. |
| 8,076,459 B2 | 12/2011 | Hofmeister et al. |
| 8,084,584 B2 | 12/2011 | Sugo et al. |
| 8,101,179 B2 | 1/2012 | Numazaki et al. |
| 8,101,722 B2 | 1/2012 | Kufer et al. |
| 8,119,130 B2 | 2/2012 | Barry et al. |
| 8,124,093 B2 | 2/2012 | Lanzavecchia et al. |
| 8,147,836 B2 | 4/2012 | Wood et al. |
| 8,163,279 B2 | 4/2012 | Bergstein |
| 8,168,757 B2 | 5/2012 | Finnefrock et al. |
| 8,183,346 B2 | 5/2012 | Leung et al. |
| 8,187,601 B2 | 5/2012 | Weng et al. |
| 8,188,234 B2 | 5/2012 | Condra et al. |
| 8,212,008 B2 | 7/2012 | Presta et al. |
| 8,212,009 B2 | 7/2012 | Kipps et al. |
| 8,258,266 B2 | 9/2012 | Deshpande et al. |
| 8,298,532 B2 | 10/2012 | Fandl et al. |
| 8,298,545 B2 | 10/2012 | Payne et al. |
| 8,298,769 B2 | 10/2012 | Smith et al. |
| 8,299,318 B2 | 10/2012 | Brover et al. |
| 8,309,693 B2 | 11/2012 | Smith et al. |
| 8,313,747 B2 | 11/2012 | Allison et al. |
| 8,314,213 B2 | 11/2012 | Bernett et al. |
| 8,318,163 B2 | 11/2012 | Appleton et al. |
| 8,323,646 B2 | 12/2012 | Swanson et al. |
| 8,343,764 B2 | 1/2013 | Abad et al. |
| 8,362,325 B2 | 1/2013 | Troukhan et al. |
| 8,410,250 B2 | 4/2013 | Ashkenazi et al. |
| 8,410,251 B2 | 4/2013 | Matsuura et al. |
| 8,414,893 B2 | 4/2013 | Biere-Citron et al. |
| 8,420,795 B2 | 4/2013 | Rodriguez et al. |
| 8,444,981 B2 | 5/2013 | Hsu et al. |
| 8,455,719 B2 | 6/2013 | Frankard et al. |
| 8,468,130 B2 | 6/2013 | Bhandari et al. |
| 8,470,324 B2 | 6/2013 | Fandl et al. |
| 8,481,692 B2 | 7/2013 | Sidhu et al. |
| 8,524,869 B2 | 9/2013 | Smith et al. |
| 8,545,847 B2 | 10/2013 | Okamoto et al. |
| 8,546,546 B2 | 10/2013 | Nakano |
| 8,551,715 B2 | 10/2013 | Gurney et al. |
| 8,568,719 B2 | 10/2013 | Williamson et al. |
| 8,575,317 B2 | 11/2013 | Kuramochi et al. |
| 8,580,257 B2 | 11/2013 | Tremblay et al. |
| 8,580,714 B2 | 11/2013 | Almagro et al. |
| 8,580,928 B2 | 11/2013 | Dennis |
| 8,586,006 B2 | 11/2013 | Hood et al. |
| 8,592,559 B2 | 11/2013 | Wakita et al. |
| 8,597,898 B2 | 12/2013 | Fandl et al. |
| 8,603,474 B2 | 12/2013 | Ritter et al. |
| 8,609,095 B2 | 12/2013 | Pedersen et al. |
| 8,632,774 B2 | 1/2014 | Misher et al. |
| 8,637,026 B2 | 1/2014 | Zauderer et al. |
| 8,637,036 B2 | 1/2014 | Mascola et al. |
| 8,673,307 B1 | 3/2014 | Nussenzweig et al. |
| 8,710,022 B2 | 4/2014 | Takahashi et al. |
| 8,715,941 B2 | 5/2014 | Abo et al. |
| 8,716,195 B2 | 5/2014 | Cappuccilli et al. |
| 8,722,046 B2 | 5/2014 | Amemiya et al. |
| 8,747,847 B2 | 6/2014 | Rotem-Yehudar et al. |
| 8,759,105 B2 | 6/2014 | Economides et al. |
| 8,790,649 B2 | 7/2014 | Setiady et al. |
| 8,816,055 B2 | 8/2014 | Sexton et al. |
| 8,846,402 B2 | 9/2014 | Economides et al. |
| 8,858,941 B2 | 10/2014 | Gurney et al. |
| 8,865,430 B2 | 10/2014 | Fandl et al. |
| 8,895,010 B2 | 11/2014 | Nadler et al. |
| 8,906,635 B2 | 12/2014 | Jin et al. |
| 8,916,160 B2 | 12/2014 | Grandea, III et al. |
| 8,926,976 B2 | 1/2015 | Corbin et al. |
| 8,927,233 B2 | 1/2015 | Fandl et al. |
| 8,937,159 B2 | 1/2015 | Harding et al. |
| 8,968,736 B2 | 3/2015 | Croll et al. |
| 8,986,972 B2 | 3/2015 | Stull et al. |
| 8,992,910 B2 | 3/2015 | Bergstein |
| 9,012,723 B2 | 4/2015 | Guo et al. |
| 9,029,508 B2 | 5/2015 | Ghayur et al. |
| 9,029,636 B2 | 5/2015 | Wu et al. |
| 9,056,910 B2 | 6/2015 | Chen et al. |
| 9,062,115 B2 | 6/2015 | Oestergaard et al. |
| 9,067,986 B2 | 6/2015 | Gurney et al. |
| 9,073,990 B2 | 7/2015 | Paas et al. |
| 9,073,991 B2 | 7/2015 | Allan et al. |
| 9,074,006 B2 | 7/2015 | Himanen et al. |
| 9,090,674 B2 | 7/2015 | Reddy et al. |
| 9,090,679 B2 | 7/2015 | Yokoseki et al. |
| 9,102,724 B2 | 8/2015 | Cummings et al. |
| 9,150,647 B2 | 10/2015 | Mellstedt et al. |
| 9,163,258 B2 | 10/2015 | Riddell et al. |
| 9,173,962 B2 | 11/2015 | Beau-Larvor et al. |
| 9,217,040 B2 | 12/2015 | Kipps et al. |
| 9,228,023 B2 | 1/2016 | Rohlff et al. |
| 9,228,208 B2 | 1/2016 | Frendewey et al. |
| 9,260,512 B2 | 2/2016 | Rodriguez et al. |
| 9,266,952 B2 | 2/2016 | Teige |
| 9,316,646 B2 | 4/2016 | Rader et al. |
| 9,758,591 B2 | 9/2017 | Kipps et al. |
| 10,344,096 B2 | 7/2019 | Kipps et al. |
| 2006/0030015 A1 | 2/2006 | Uda et al. |
| 2008/0318212 A1 | 12/2008 | Wilson et al. |
| 2009/0137416 A1 | 5/2009 | Fandl et al. |
| 2009/0203886 A1 | 8/2009 | Uchiyama et al. |
| 2010/0129817 A1 | 5/2010 | Wei et al. |
| 2011/0104053 A1 | 5/2011 | Rodriguez et al. |
| 2011/0165650 A1 | 7/2011 | Fandl et al. |
| 2012/0058051 A1 | 3/2012 | Rader et al. |
| 2012/0282177 A1 | 11/2012 | Rohlff et al. |
| 2013/0039925 A1 | 2/2013 | Bansal |
| 2013/0251642 A1 | 9/2013 | Rader et al. |
| 2014/0065167 A1 | 3/2014 | Rodriguez et al. |
| 2014/0072979 A1 | 3/2014 | Fandl et al. |
| 2014/0072980 A1 | 3/2014 | Fandl et al. |
| 2014/0134719 A1 | 5/2014 | Despande et al. |
| 2015/0232569 A1 | 8/2015 | Kipps et al. |

FOREIGN PATENT DOCUMENTS

| | | |
|---|---|---|
| CA | 2 851 941 A1 | 5/2013 |
| CA | 2 854 126 A1 | 5/2013 |
| CN | 103792364 A | 5/2014 |
| EP | 2 617 320 A1 | 7/2013 |
| JP | 2006-311857 A | 11/2006 |
| KR | 2014-0008308 A | 1/2014 |
| WO | WO-2003/018632 A2 | 3/2003 |
| WO | WO-2003/018632 A3 | 3/2003 |
| WO | WO-2004/009805 A1 | 1/2004 |
| WO | WO-2006/106959 A1 | 10/2006 |

(56) References Cited

FOREIGN PATENT DOCUMENTS

| | | |
|---|---|---|
| WO | WO-2007/102230 A1 | 9/2007 |
| WO | WO-2007/146957 A2 | 12/2007 |
| WO | WO-2007/146957 A3 | 12/2007 |
| WO | WO-2008/062063 A1 | 5/2008 |
| WO | WO-2008/076868 A2 | 6/2008 |
| WO | WO-2008/076868 A3 | 6/2008 |
| WO | WO-2008/103849 A2 | 8/2008 |
| WO | WO-2008/103849 A3 | 8/2008 |
| WO | WO-2008/103849 A4 | 8/2008 |
| WO | WO-2009/031230 A1 | 3/2009 |
| WO | WO-2009/101611 A1 | 8/2009 |
| WO | WO-2009/154283 A1 | 12/2009 |
| WO | WO-2010/008069 A1 | 1/2010 |
| WO | WO-2010/124188 A1 | 10/2010 |
| WO | WO-2011/054007 A1 | 5/2011 |
| WO | WO-2011057788 A1 | 5/2011 |
| WO | WO-2011/079902 A2 | 7/2011 |
| WO | WO-2011/079902 A3 | 7/2011 |
| WO | WO-2011/107957 A1 | 9/2011 |
| WO | WO-2011/131407 A1 | 10/2011 |
| WO | WO-2012/008494 A1 | 1/2012 |
| WO | WO-2012/069550 A1 | 5/2012 |
| WO | WO-2012/075158 A1 | 6/2012 |
| WO | WO-2012/076066 A1 | 6/2012 |
| WO | WO-2012/076727 A1 | 6/2012 |
| WO | WO-2012/097313 A2 | 7/2012 |
| WO | WO-2012/097313 A3 | 7/2012 |
| WO | WO-2012/156018 A1 | 11/2012 |
| WO | WO-2013/019730 A1 | 2/2013 |
| WO | WO-2013/125636 A1 | 8/2013 |
| WO | WO-2013/125654 A1 | 8/2013 |
| WO | WO-2013/147153 A1 | 10/2013 |
| WO | WO-2013/147169 A1 | 10/2013 |
| WO | WO-2013/147176 A1 | 10/2013 |
| WO | WO-2013/152020 A1 | 10/2013 |
| WO | WO-2013/172961 A1 | 11/2013 |
| WO | WO-2013/174264 A1 | 11/2013 |
| WO | WO-2014/130879 A2 | 8/2014 |
| WO | WO-2014/130879 A3 | 8/2014 |
| WO | WO-2014/167022 A1 | 10/2014 |
| WO | WO-2014/174111 A1 | 10/2014 |
| WO | WO-2014/189973 A2 | 11/2014 |
| WO | WO-2014/189973 A3 | 11/2014 |
| WO | WO-2015/014376 A1 | 2/2015 |
| WO | WO-2015/031693 A1 | 3/2015 |
| WO | WO-2015/069794 A2 | 5/2015 |
| WO | WO-2015/069794 A3 | 5/2015 |
| WO | WO-2015/069794 A9 | 5/2015 |
| WO | WO-2015/089344 A1 | 6/2015 |
| WO | WO-2015/095392 A1 | 6/2015 |
| WO | WO-2015/099838 A2 | 7/2015 |
| WO | WO-2015/099838 A3 | 7/2015 |
| WO | WO-2015/116653 A1 | 8/2015 |
| WO | WO-2015/127407 A1 | 8/2015 |
| WO | WO-2015/150327 A1 | 10/2015 |
| WO | WO-2015/162293 A1 | 10/2015 |

OTHER PUBLICATIONS

Daneshmanesh, A.H. et al. (Sep. 1, 2008). "Ror1, a cell surface receptor tyrosine kinase is expressed in chronic lymphocytic leukemia and may serve as a putative target for therapy," *Int J Cancer* 123(5):1190-1195.

Dermer, G.B. (Mar. 1994). "The Last Word: Another Anniversary for the War on Cancer," *Bio/Technology* 12(3):320.

Freshney, R.I. (1983). Culture of Animal Cells: A Manual of Basic Technique, 4 pages.

George, J. et al. (Mar. 10, 1998). "Differential effects of anti-beta2-glycoprotein I antibodies on endothelial cells and on the manifestations of experimental antiphospholipid syndrome," *Circulation* 97(9):900-906.

Gura, T. et al. (Nov. 7, 1997). "Systems for identifying new drugs are often faulty," *Science* 278(5340):1041-1042.

International Search Report dated Sep. 9, 2013, for PCT Application No. PCT/US2013/032572, filed Mar. 15, 2013, 5 pages.

Jain, R.K. (Jul. 1994). "Barriers to drug delivery in solid tumors," *Sci Am* 271(1):58-65.

Kataja, V. et al. (May 2009). "Primary breast cancer: ESMO clinical recommendations for diagnosis, treatment and follow-up," Annals of Oncology 20(Suppl 4):10-14.

Lippincott-Schwartz, J. (2002). "Antibodies as Cell Biological Tools," Chapter 16 in *Current Protocols in Cell Biology* 16.0.1-16.0.2.

Miyako, H. et al. (2006). Surgery Frontier, 2006, vol. 13, No. 3, pp. 40-43.

Nelson, H.D. et al. (Nov. 17, 2009). "Screening for breast cancer: an update for the U.S. Preventive Services Task Force," Ann Intern Med 151(10):727-737.

Parker, B. (Jun. 12, 2012). "ROR1 Expression in Human Breast Cancer," AIM #3, methods, paragraphs 1-3, 4 pages.

Pascalis, R. et al. (2002). "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.

Paul, W.E. (1993). Fundamental Immunology, 3$^{rd}$ Edition, pp. 292-295.

Rudikoff, S. et al. (Mar. 1982). "Single amino acid substitution altering antigen-binding specificity," *PNAS USA* 79(6):1979-1983.

Strome, S.E et al. (Sep. 2007). "A mechanistic perspective of monoclonal antibodies in cancer therapy beyond target-related effects," *Oncologist* 12(9):1084-1095.

(B)

(C)

(D)

(E)

(F)

(G)

(H)

(I)

(J)

(K)

SEQUENCE LISTING

```
<160> NUMBER OF SEQ ID NOS: 48

<210> SEQ ID NO 1
<211> LENGTH: 116
<212> TYPE: PRT
<213> ORGANISM: Artificial Sequence
<220> FEATURE:
<223> OTHER INFORMATION: Synthetic construct

<400> SEQUENCE: 1

Glu Ile Gln Leu Gln Gln Ser Gly Pro Val Leu Val Lys Pro Gly Ala
1               5                   10                  15

Ser Val Lys Val Ser Cys Lys Ala Ser Gly Tyr Ala Phe Thr Ala Tyr
            20                  25                  30
```

Asn Ile His Trp Val Arg Gln Ser His Gly Lys Arg Leu Glu Trp Ile
        35                  40                  45

Gly Ser Phe Asp Pro Tyr Asp Gly Gly Ser Ser Tyr Asn Gln Lys Phe
    50                  55                  60

Lys Asp Lys Ala Thr Leu Thr Val Asp Lys Ser Ser Thr Thr Ala Tyr
65                  70                  75                  80

Met His Leu Asn Ser Leu Thr Ser Glu Asp Ser Ala Val Tyr Tyr Cys
                85                  90                  95

Ala Arg Gly Trp Tyr Tyr Phe Asp Tyr Trp Gly His Gly Thr Thr Leu
            100                 105                 110

Thr Val Ser Ser
        115

<210> SEQ ID NO 2
<211> LENGTH: 348
<212> TYPE: DNA
<213> ORGANISM: Mus musculus

<400> SEQUENCE: 2
gagatccagc tgcagcagtc tggacctgtc ctggtgaagc ctggggcttc agtgaaggtt     60
tcttgcaagg cttctggtta tgcattcact gcctacaaca tacactgggt gagacagagc    120
catggaaagc gccttgagtg gattggatct tttgatcctt acgatggtgg tagtagttac    180
aaccagaagt tcaaggacaa agccacattg actgtagaca aatcttccac cacagcctac    240
atgcatctca cagcctgac atctgaggac tctgcagtct attactgtgc aaggggggtgg    300 tactactttg actactgggg ccacgggacc actctcacag tctcctca                 348

<210> SEQ ID NO 3
<211> LENGTH: 108
<212> TYPE: PRT
<213> ORGANISM: Mus musculus

<400> SEQUENCE: 3

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Arg Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asp Glu Ser Pro Tyr
                85                  90                  95

Thr Phe Gly Glu Gly Thr Lys Leu Glu Ile Lys Arg
            100                 105

<210> SEQ ID NO 4
<211> LENGTH: 324
<212> TYPE: DNA
<213> ORGANISM: Mus musculus

<400> SEQUENCE: 4
gacgtccaga taacccagtc tccatcttat cttgctgcat ctcctggaga aaccattact     60
attaattgca gggcaagtaa gagcattagc aaatatttag cctggtatca agagaaacct    120

```
gggaaaacta ataagctcct tatctactct ggatccactt tgcaatctgg aattccatca      180
agattcaggg gcagtggatc tggtacagat ttcactctca ccatcagtag cctggagcct      240
gaagattttg caatgtatta ctgtcaacag catgatgaat ccccgtacac gttcggagag      300
gggaccaagc tggaaataaa acgg                                             324
```

<210> SEQ ID NO 5
<211> LENGTH: 116
<212> TYPE: PRT
<213> ORGANISM: Artificial Sequence
<220> FEATURE:
<223> OTHER INFORMATION: Synthetic construct

<400> SEQUENCE: 5

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ala Phe Thr Ala Tyr
             20                  25                  30

Asn Ile His Trp Val Arg Gln Ala Pro Gly Gln Gly Leu Glu Trp Met
         35                  40                  45

Gly Ser Phe Asp Pro Tyr Asp Gly Gly Ser Tyr Asn Gln Lys Phe
     50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                 85                  90                  95

Ala Arg Gly Trp Tyr Tyr Phe Asp Tyr Trp Gly His Gly Thr Leu Val
                100                 105                 110

Thr Val Ser Ser
            115
```

<210> SEQ ID NO 6
<211> LENGTH: 348
<212> TYPE: DNA
<213> ORGANISM: Artificial Sequence
<220> FEATURE:
<223> OTHER INFORMATION: Synthetic construct

<400> SEQUENCE: 6

```
caggtgcagc tgcaggagtc gggcccagga ctggtgaagc cttcacagac cctgtccctc       60
acctgcactg tctctggtta tgcattcact gcctacaaca tacactgggt gcgacaggcc      120
cctggacaag gcttgagtg gatgggttct tttgatcctt acgatggtgg tagtagttac      180
aaccagaagt tcaaggacag actcaccatc tccaaggaca cctccaaaaa ccaggtggtc      240
cttacaatga ccaacatgga ccctgtggac acagccacgt attactgtgc aagagggtgg      300
tactactttg actactgggg ccacggaacc ctggtcaccg tctcctca                   348
```

<210> SEQ ID NO 7
<211> LENGTH: 107
<212> TYPE: PRT
<213> ORGANISM: Artificial Sequence
<220> FEATURE:
<223> OTHER INFORMATION: Synthetic construct

<400> SEQUENCE: 7

```
Asp Ile Val Met Thr Gln Thr Pro Leu Ser Leu Pro Val Thr Pro Gly
 1               5                  10                  15

Glu Pro Ala Ser Ile Ser Cys Arg Ala Ser Lys Ser Ile Ser Lys Tyr
```

```
                 20                  25                  30

Leu Ala Trp Tyr Gln Gln Lys Pro Gly Gln Ala Pro Arg Leu Leu Ile
             35                  40                  45

Tyr Ser Gly Ser Thr Leu Gln Ser Gly Ile Pro Pro Arg Phe Ser Gly
         50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Gln Gln His Asp Glu Ser Pro Tyr
                 85                  90                  95

Thr Phe Gly Glu Gly Thr Lys Val Glu Ile Lys
            100                 105

<210> SEQ ID NO 8
<211> LENGTH: 321
<212> TYPE: DNA
<213> ORGANISM: Artificial Sequence
<220> FEATURE:
<223> OTHER INFORMATION: Synthetic construct

<400> SEQUENCE: 8
gatattgtga tgacccagac tccactctcc ctgcccgtca cccctggaga gccggcctcc      60
atctcctgca gggcaagtaa gagcattagc aaatatttag cctggtacca gcagaaacct     120
ggccaggctc ccaggctcct catctattct ggatccactt tgcaatctgg gatcccacct     180
cgattcagtg gcagcgggta tggaacagat tttaccctca caattaataa catagaatct     240
gaggatgctg catattactt ctgtcaacag catgatgaat ccccgtacac gttcggcgag     300
gggaccaagg tggaaatcaa a                                                321

<210> SEQ ID NO 9
<211> LENGTH: 116
<212> TYPE: PRT
<213> ORGANISM: Artificial Sequence
<220> FEATURE:
<223> OTHER INFORMATION: Synthetic construct

<400> SEQUENCE: 9

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ala Phe Thr Ala Tyr
             20                  25                  30

Asn Ile His Trp Val Arg Gln Ala Pro Gly Gln Gly Leu Glu Trp Met
         35                  40                  45

Gly Ser Phe Asp Pro Tyr Asp Gly Gly Ser Ser Tyr Asn Gln Lys Phe
     50                  55                  60

Lys Asp Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Gly Trp Tyr Tyr Phe Asp Tyr Trp Gly His Gly Thr Leu Val
            100                 105                 110

Thr Val Ser Ser
        115

<210> SEQ ID NO 10
<211> LENGTH: 348
<212> TYPE: DNA
<213> ORGANISM: Artificial Sequence
<220> FEATURE:
```

<223> OTHER INFORMATION: Synthetic construct

<400> SEQUENCE: 10

```
caggtgcagc tgcaggagtc gggcccagga ctggtgaagc cttcacagac cctgtccctc      60
acctgcactg tctctggtta tgcattcact gcctacaaca tacactgggt gcgacaggcc     120
cctggacaag ggcttgagtg gatgggttct tttgatcctt acgatggtgg tagtagttac     180
aaccagaagt tcaaggacag actcaccatc tccaaggaca cctccaaaaa ccaggtggtc     240
cttacaatga ccaacatgga ccctgtggac acagccacgt attactgtgc aagagggtgg     300
tactactttg actactgggg ccacggaacc ctggtcaccg tctcctca                  348
```

<210> SEQ ID NO 11
<211> LENGTH: 107
<212> TYPE: PRT
<213> ORGANISM: Artificial Sequence
<220> FEATURE:
<223> OTHER INFORMATION: Synthetic construct

<400> SEQUENCE: 11

```
Asp Val Val Met Thr Gln Ser Pro Leu Ser Leu Pro Val Thr Leu Gly
1               5                   10                  15
Gln Pro Ala Ser Ile Ser Cys Arg Ala Ser Lys Ser Ile Ser Lys Tyr
            20                  25                  30
Leu Ala Trp Tyr Gln Gln Lys Pro Gly Lys Ala Pro Lys Leu Leu Ile
        35                  40                  45
Tyr Ser Gly Ser Thr Leu Gln Ser Gly Ile Pro Pro Arg Phe Ser Gly
    50                  55                  60
Ser Gly Tyr Gly Thr Asp Phe Thr Leu Thr Ile Asn Asn Ile Glu Ser
65                  70                  75                  80
Glu Asp Ala Ala Tyr Tyr Phe Cys Gln Gln His Asp Glu Ser Pro Tyr
                85                  90                  95
Thr Phe Gly Glu Gly Thr Lys Val Glu Ile Lys
            100                 105
```

<210> SEQ ID NO 12
<211> LENGTH: 321
<212> TYPE: DNA
<213> ORGANISM: Artificial Sequence
<220> FEATURE:
<223> OTHER INFORMATION: Synthetic construct

<400> SEQUENCE: 12

```
gatgttgtga tgactcagtc tccactctcc ctgcccgtca cccttggaca gccggcctcc      60
atctcctgca gggcaagtaa gagcattagc aaatatttag cctggtatca gcagaaacca     120
gggaaagctc ctaagctcct gatctattct ggatccactt tgcaatctgg gatcccacct     180
cgattcagtg gcagcgggta tggaacagat tttaccctca caattaataa catagaatct     240
gaggatgctg catattactt ctgtcaacag catgatgaat ccccgtacac gttcggcgag     300
gggaccaagg tggaaatcaa a                                               321
```

<210> SEQ ID NO 13
<211> LENGTH: 116
<212> TYPE: PRT
<213> ORGANISM: Artificial Sequence
<220> FEATURE:
<223> OTHER INFORMATION: Synthetic construct

<400> SEQUENCE: 13

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Ile Arg Gln Pro Pro Gly Lys Gly Leu Glu Trp Ile
        35                  40                  45

Gly Ser Phe Asp Pro Tyr Asp Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115
```

<210> SEQ ID NO 14
<211> LENGTH: 348
<212> TYPE: DNA
<213> ORGANISM: Artificial Sequence
<220> FEATURE:
<223> OTHER INFORMATION: Synthetic construct

<400> SEQUENCE: 14

```
caggtgcagc tgcaggagtc gggcccagga ctggtgaagc cttcacagac cctgtccctc    60
acctgcactg tctctggtta tgcattcact gcctacaaca tacactggat ccgccagccc   120
ccagggaagg gctggagtg gattggttct tttgatcctt acgatggtgg tagtagttac   180
aaccagaagt tcaaggacag actcaccatc tccaaggaca cctccaaaaa ccaggtggtc   240
cttacaatga ccaacatgga ccctgtggac acagccacgt attactgtgc aagagggtgg   300
tactactttg actactgggg ccacggaacc ctggtcaccg tctcctca                348
```

<210> SEQ ID NO 15
<211> LENGTH: 107
<212> TYPE: PRT
<213> ORGANISM: Artificial Sequence
<220> FEATURE:
<223> OTHER INFORMATION: Synthetic construct

<400> SEQUENCE: 15

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105
```

<210> SEQ ID NO 16

<211> LENGTH: 321
<212> TYPE: DNA
<213> ORGANISM: Artificial Sequence
<220> FEATURE:
<223> OTHER INFORMATION: Synthetic construct

<400> SEQUENCE: 16

```
gatattgtga tgacccagac tccactctcc ctgcccgtca cccctggaga gccggcctcc    60
atctcctgca gggcaagtaa gagcattagc aaatatttag cctggtacca gcagaaacct   120
ggccaggctc ccaggctcct catctattct ggatccactt tgcaatctgg gatcccacct   180
cgattcagtg gcagcgggta tggaacagat tttacccctca caattaataa catagaatct   240
gaggatgctg catattactt ctgtcaacag catgatgaat ccccgtacac gttcggcgag   300
gggaccaagg tggaaatcaa a                                             321
```

<210> SEQ ID NO 17
<211> LENGTH: 116
<212> TYPE: PRT
<213> ORGANISM: Artificial Sequence
<220> FEATURE:
<223> OTHER INFORMATION: Synthetic construct

<400> SEQUENCE: 17

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Ile Arg Gln Pro Pro Gly Lys Gly Leu Glu Trp Ile
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115
```

<210> SEQ ID NO 18
<211> LENGTH: 348
<212> TYPE: DNA
<213> ORGANISM: Artificial Sequence
<220> FEATURE:
<223> OTHER INFORMATION: Synthetic construct

<400> SEQUENCE: 18

```
caggtgcagc tgcaggagtc gggcccagga ctggtgaagc cttcacagac cctgtccctc    60
acctgcactg tctctggtta tgcattcact gcctacaaca tacactggat ccgccagccc   120
ccagggaagg gctggagtg gattggttct tttgatcctt acgatggtgg tagtagttac   180
aaccagaagt tcaaggacag actcaccatc tccaaggaca cctccaaaaa ccaggtggtc   240
cttacaatga ccaacatgga ccctgtggac acagccacgt attactgtgc aagagggtgg   300
tactactttg actactgggg ccacggaacc ctggtcaccg tctcctca                348
```

<210> SEQ ID NO 19
<211> LENGTH: 107

```
<212> TYPE: PRT
<213> ORGANISM: Artificial Sequence
<220> FEATURE:
<223> OTHER INFORMATION: Synthetic construct

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 20
<211> LENGTH: 321
<212> TYPE: DNA
<213> ORGANISM: Artificial Sequence
<220> FEATURE:
<223> OTHER INFORMATION: Synthetic construct

<400> SEQUENCE: 20
gatgttgtga tgactcagtc tccactctcc ctgcccgtca cccttggaca gccggcctcc      60
atctcctgca gggcaagtaa gagcattagc aaatatttag cctggtatca gcagaaacca     120
gggaaagctc ctaagctcct gatctattct ggatccactt tgcaatctgg gatcccacct     180
cgattcagtg gcagcgggta tggaacagat tttaccctca caattaataa catagaatct     240
gaggatgctg catattactt ctgtcaacag catgatgaat ccccgtacac gttcggcgag     300
gggaccaagg tggaaatcaa a                                                321

<210> SEQ ID NO 21
<211> LENGTH: 252
<212> TYPE: PRT
<213> ORGANISM: Artificial Sequence
<220> FEATURE:
<223> OTHER INFORMATION: Synthetic construct

<400> SEQUENCE: 21

Asp Ile Val Met Thr Thr Gln Thr Pro Leu Ser Leu Pro Val Thr Pro
1               5                   10                  15

Gly Glu Pro Ala Ser Ile Ser Cys Arg Ala Ser Lys Ser Ile Ser Lys
            20                  25                  30

Tyr Leu Ala Trp Tyr Gln Gln Lys Pro Gly Gln Ala Pro Arg Leu Leu
        35                  40                  45

Ile Tyr Ser Gly Ser Thr Leu Gln Ser Gly Ile Pro Pro Arg Phe Ser
    50                  55                  60

Gly Ser Gly Tyr Gly Thr Asp Phe Thr Leu Thr Ile Asn Asn Ile Glu
65                  70                  75                  80

Ser Glu Asp Ala Ala Tyr Tyr Phe Cys Gln Gln His Asp Glu Ser Pro
                85                  90                  95

Tyr Thr Phe Gly Glu Gly Thr Lys Val Glu Ile Lys Gly Gly Gly Gly
```

```
            100                 105                 110
Ser Gly Ser Thr Ser Gly Ser Gly Lys Pro Gly Ser Gly Glu Gly Ser
            115                 120                 125

Thr Lys Gly Gly Gly Gly Ser Gln Val Gln Leu Gln Glu Ser Gly
        130                 135                 140

Pro Gly Leu Val Lys Pro Ser Gln Thr Leu Ser Leu Thr Cys Thr Val
145                 150                 155                 160

Ser Gly Tyr Ala Phe Thr Ala Tyr Asn Ile His Trp Val Arg Gln Ala
                165                 170                 175

Pro Gly Gln Gly Leu Glu Trp Met Gly Ser Phe Asp Pro Tyr Asp Gly
            180                 185                 190

Gly Ser Ser Tyr Asn Gln Lys Phe Lys Asp Arg Leu Thr Ile Ser Lys
            195                 200                 205

Asp Thr Ser Lys Asn Gln Val Val Leu Thr Met Thr Asn Met Asp Pro
        210                 215                 220

Val Asp Thr Ala Thr Tyr Tyr Cys Ala Arg Gly Trp Tyr Tyr Phe Asp
225                 230                 235                 240

Tyr Trp Gly His Gly Thr Leu Val Thr Val Ser Ser
                245                 250
```

<210> SEQ ID NO 22
<211> LENGTH: 753
<212> TYPE: DNA
<213> ORGANISM: Artificial Sequence
<220> FEATURE:
<223> OTHER INFORMATION: Synthetic construct

<400> SEQUENCE: 22

```
gatattgtga tgacccagac tccactctcc ctgcccgtca cccctggaga gccggcctcc     60
atctcctgca gggcaagtaa gagcattagc aaatatttag cctggtacca gcagaaacct    120
ggccaggctc ccaggctcct catctattct ggatccactt tgcaatctgg gatcccacct    180
cgattcagtg gcagcgggta tggaacagat tttaccctca caattaataa catagaatct    240
gaggatgctg catattactt ctgtcaacag catgatgaat cccgtacacg gttcggcgag    300
gggaccaagg tggaaatcaa aggtggtggt ggtagcggct ccacctctgg atccggcaag    360
cccggatctg gcgagggatc caccaagggc ggaggaggag gaagtcaggt gcagctgcag    420
gagtcgggcc caggactggt gaagccttca gagaccctgt ccctcacctg cactgtctct    480
ggttatgcat tcactgccta acatacac tgggtgcgac aggcccctgg acaagggctt    540
gagtggatgg gttcttttga tccttacgat ggtggtagta gttacaacca gaagttcaag    600
gacagactca ccatctccaa ggacacctcc aaaaaccagg tggtccttac aatgaccaac    660
atggaccctg tggacacagc cacgtattac tgtgcaagag ggtggtacta ctttgactac    720
tggggccacg gaaccctggt caccgtctcc tca                                 753
```

<210> SEQ ID NO 23
<211> LENGTH: 251
<212> TYPE: PRT
<213> ORGANISM: Artificial Sequence
<220> FEATURE:
<223> OTHER INFORMATION: Synthetic construct

<400> SEQUENCE: 23

```
Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Ile Ser Lys Tyr
```

```
                    20                  25                  30
Leu Ala Trp Tyr Gln Gln Lys Pro Gly Lys Ala Pro Lys Leu Leu Ile
            35                  40                  45

Tyr Ser Gly Ser Thr Leu Gln Ser Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Gly Gly Gly Gly Ser
            100                 105                 110

Gly Ser Thr Ser Gly Ser Gly Lys Pro Gly Ser Gly Glu Gly Ser Thr
        115                 120                 125

Lys Gly Gly Gly Gly Ser Gln Val Gln Leu Gln Glu Ser Gly Pro
    130                 135                 140

Gly Leu Val Lys Pro Ser Gln Thr Leu Ser Leu Thr Cys Thr Val Ser
145                 150                 155                 160

Gly Tyr Ala Phe Thr Ala Tyr Asn Ile His Trp Val Arg Gln Ala Pro
                165                 170                 175

Gly Gln Gly Leu Glu Trp Met Gly Ser Phe Asp Pro Tyr Asp Gly Gly
            180                 185                 190

Ser Ser Tyr Asn Gln Lys Phe Lys Asp Arg Leu Thr Ile Ser Lys Asp
        195                 200                 205

Thr Ser Lys Asn Gln Val Val Leu Thr Met Thr Asn Thr Asp Pro Val
    210                 215                 220

Asp Thr Ala Thr Tyr Tyr Cys Ala Arg Gly Trp Tyr Tyr Phe Asp Tyr
225                 230                 235                 240

Trp Gly His Gly Thr Leu Val Thr Val Ser Ser
                245                 250

<210> SEQ ID NO 24
<211> LENGTH: 753
<212> TYPE: DNA
<213> ORGANISM: Artificial Sequence
<220> FEATURE:
<223> OTHER INFORMATION: Synthetic construct

<400> SEQUENCE: 24
gatgttgtga tgactcagtc tccactctcc ctgcccgtca cccttggaca gccggcctcc      60
atctcctgca gggcaagtaa gagcattagc aaatatttag cctggtatca gcagaaacca     120
gggaaagctc ctaagctcct gatctattct ggatccactt tgcaatctgg gatcccacct     180
cgattcagtg gcagcgggta tggaacagat tttacccctca caattaataa catagaatct     240
gaggatgctg catattactt ctgtcaacag catgatgaat ccccgtacac gttcggcgag     300
gggaccaagg tggaaatcaa aggtggtggt ggtagcggct ccacctctgg atccggcaag     360
cccggatctg gcgagggatc caccaagggc ggaggaggag gaagtcaggt gcagctgcag     420
gagtcgggcc caggactggt gaagccttca cagaccctgt ccctcacctg cactgtctct     480
ggttatgcat tcactgccta acatacac tgggtgcgac aggcccctgg acaagggctt     540
gagtggatgg gttcttttga tccttacgat ggtggtagta gttacaacca gaagttcaag     600
gacagactca ccatctccaa ggacacctcc aaaaaccagg tggtccttac aatgaccaac     660
atggaccctg tggacacagc cacgtattac tgtgcaagag gtggtactac ctttgactac     720
tggggccacg gaaccctggt caccgtctcc tca                                  753
```

```
<210> SEQ ID NO 25
<211> LENGTH: 22
<212> TYPE: PRT
<213> ORGANISM: Artificial Sequence
<220> FEATURE:
<223> OTHER INFORMATION: Synthetic construct

<400> SEQUENCE: 25

Val Ala Thr Asn Gly Lys Glu Val Val Ser Ser Thr Gly Val Leu Phe
1               5                   10                  15

Val Lys Phe Gly Pro Cys
            20

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Glu Val Val Ser Ser Thr Gly Val Leu Phe Val Lys Phe Gly Pro Cys
1               5                   10                  15

<210> SEQ ID NO 27
<211> LENGTH: 8
<212> TYPE: PRT
<213> ORGANISM: Artificial Sequence
<220> FEATURE:
<223> OTHER INFORMATION: Synthetic construct

<400> SEQUENCE: 27

Gly Tyr Ala Phe Thr Ala Tyr Asn
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic construct

<400> SEQUENCE: 28

Phe Asp Pro Tyr Asp Gly Gly Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic construct

<400> SEQUENCE: 29

Gly Trp Tyr Tyr Phe Asp Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic conctruct

<400> SEQUENCE: 30
```

```
Lys Ser Ile Ser Lys Tyr
1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic construct

<400> SEQUENCE: 31

Ser Gly Ser
1

<210> SEQ ID NO 32
<211> LENGTH: 8
<212> TYPE: PRT
<213> ORGANISM: Artificial Sequence
<220> FEATURE:
<223> OTHER INFORMATION: Synthetic construct

<400> SEQUENCE: 32

Gln Gln His Asp Glu Ser Pro Tyr
1               5

<210> SEQ ID NO 33
<211> LENGTH: 15
<212> TYPE: PRT
<213> ORGANISM: Artificial Sequence
<220> FEATURE:
<223> OTHER INFORMATION: Synthetic construct

<400> SEQUENCE: 33

Ser Gly Tyr Ala Phe Thr Ala Tyr Asn Ile His Trp Val Arg Gln
1               5                   10                  15

<210> SEQ ID NO 34
<211> LENGTH: 18
<212> TYPE: PRT
<213> ORGANISM: Artificial Sequence
<220> FEATURE:
<223> OTHER INFORMATION: Synthetic construct

<400> SEQUENCE: 34

Gly Ser Phe Asp Pro Tyr Asp Gly Gly Ser Ser Tyr Asn Gln Lys Phe
1               5                   10                  15

Lys Asp

<210> SEQ ID NO 35
<211> LENGTH: 23
<212> TYPE: PRT
<213> ORGANISM: Artificial Sequence
<220> FEATURE:
<223> OTHER INFORMATION: Synthetic construct

<400> SEQUENCE: 35

Tyr Tyr Cys Ala Arg Gly Trp Tyr Tyr Phe Asp Tyr Trp Gly His Gly
1               5                   10                  15

Thr Leu Val Thr Val Ser Ser
            20

<210> SEQ ID NO 36
<211> LENGTH: 14
<212> TYPE: PRT
<213> ORGANISM: Artificial Sequence
<220> FEATURE:
```

```
<223> OTHER INFORMATION: Synthetic construct

<400> SEQUENCE: 36

Cys Arg Ala Ser Lys Ser Ile Ser Lys Tyr Leu Ala Trp Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic construct

<400> SEQUENCE: 37

Leu Leu Ile Tyr Ser Gly Ser Thr Leu Gln Ser Gly
1               5                   10

<210> SEQ ID NO 38
<211> LENGTH: 20
<212> TYPE: PRT
<213> ORGANISM: Artificial Sequence
<220> FEATURE:
<223> OTHER INFORMATION: Synthetic construct

<400> SEQUENCE: 38

Cys Gln Gln His Asp Glu Ser Pro Tyr Thr Phe Gly Glu Gly Thr Lys
1               5                   10                  15

Val Glu Ile Lys
            20

<210> SEQ ID NO 39
<211> LENGTH: 117
<212> TYPE: PRT
<213> ORGANISM: Mus musculus

<400> SEQUENCE: 39

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser
        115

<210> SEQ ID NO 40
<211> LENGTH: 351
<212> TYPE: DNA
<213> ORGANISM: Mus musculus

<400> SEQUENCE: 40
caggtgcagc tgaaggagtc aggacctggc ctggtggcgc cctcacagac tctgtccatc      60
acttgcactg tctctgggtt ttcattaacc agttatggtg tacactgggt tcgccagcct     120
```

```
ccaggaaagg gtctggagtg gctgggagta atatgggctg gtggattcac aaattataat    180
tcggctctca agtccagact gagcatcagc aaagacaact ccaagagcca agttctctta    240
aaaatgacca gtctgcaaac tgatgacaca gccatgtact actgtgccag agagggtagt    300
tcctattcta tggactattg gggtcaagga acctcagtca ccgtctcctc a             351
```

<210> SEQ ID NO 41
<211> LENGTH: 106
<212> TYPE: PRT
<213> ORGANISM: Mus musculus

<400> SEQUENCE: 41

```
Glu Ile Val Leu Ser Gln Ser Pro Ala Ile Thr Ala Ala Ser Leu Gly
1               5                   10                  15

Gln Lys Val Thr Ile Thr Cys Ser Ala Ser Ser Asn Val Ser Tyr Ile
            20                  25                  30

His Trp Tyr Gln Gln Arg Ser Gly Thr Ser Pro Arg Pro Trp Ile Tyr
        35                  40                  45

Glu Ile Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Gln
            100                 105
```

<210> SEQ ID NO 42
<211> LENGTH: 318
<212> TYPE: DNA
<213> ORGANISM: Mus musculus

<400> SEQUENCE: 42

```
gaaattgtgc tctctcagtc tccagccatc acagctgcat ctctgggcca aaaggtcacc    60
atcacctgca gtgccagttc aaatgtaagt tacatccact ggtaccagca gaggtcaggc   120
acctccccca gaccatggat ttatgaaata tccaaactgg cttctggagt cccagttcgc   180
ttcagtggca gtgggtctgg gacctcttac tctctcacaa tcagcagcat ggaggctgaa   240
gatgctgcca tttattattg tcagcagtgg aattatcctc ttatcacgtt cggctcgggg   300
acaaagttgg aaatacaa                                                 318
```

<210> SEQ ID NO 43
<211> LENGTH: 119
<212> TYPE: PRT
<213> ORGANISM: Mus musculus

<400> SEQUENCE: 43

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
```

```
                65                  70                  75                  80
Gln Met Ser Ser Leu Arg Ser Glu Asp Thr Ala Met Tyr Tyr Cys Gly
                    85                  90                  95

Arg Tyr Asp Tyr Asp Gly Tyr Tyr Ala Met Asp Tyr Trp Gly Gln Gly
                100                 105                 110

Thr Ser Val Thr Val Ser Ser
            115

<210> SEQ ID NO 44
<211> LENGTH: 357
<212> TYPE: DNA
<213> ORGANISM: Mus musculus

<400> SEQUENCE: 44
gaagtgaaac tggtggagtc tgggggaggc ttagtgaagc ctggagggtc cctgaaactc      60
tcctgtgcag cctctggatt cactttcagt agctatgcca tgtcttgggt tcgccagatt     120
ccagagaaga ggctggagtg gtcgcatcc attagtcgtg gtggtaccac ctactatcca      180
gacagtgtga agggccgatt caccatctcc agagataatg tcaggaacat cctgtacctg     240
caaatgagca gtctgaggtc tgaggacacg gccatgtatt actgtggaag atatgattac     300
gacgggtact atgcaatgga ctactgggt caaggaacct cagtcaccgt ctcctca        357

<210> SEQ ID NO 45
<211> LENGTH: 107
<212> TYPE: PRT
<213> ORGANISM: Mus musculus

<400> SEQUENCE: 45

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105

<210> SEQ ID NO 46
<211> LENGTH: 322
<212> TYPE: DNA
<213> ORGANISM: Mus musculus

<400> SEQUENCE: 46
gacatcaaga tgacccagtc tccatcttcc atgtatgcat ctctaggaga gagagtcact     60
atcacttgca aggcgagtcc ggacattaat agctatttaa gctggttcca gcagaaacca    120
gggaaatctc ctaagaccct gatctatcgt gcaaacagat tggttgatgg ggtcccatca    180
aggttcagtg gcggtggatc tgggcaagat tattctctca ccatcaacag cctggagtat    240
gaagatatgg gaatttatta ttgtctacag tatgatgaat tccgtacac gttcggaggg     300 gggaccaagc tggaaatgaa ac                                              322
```

```
<210> SEQ ID NO 47
<211> LENGTH: 20
<212> TYPE: DNA
<213> ORGANISM: Artificial Sequence
<220> FEATURE:
<223> OTHER INFORMATION: Synthetic construct

<400> SEQUENCE: 47
tccggattgg aattcccatg                                              20

<210> SEQ ID NO 48
<211> LENGTH: 21
<212> TYPE: DNA
<213> ORGANISM: Artificial Sequence
<220> FEATURE:
<223> OTHER INFORMATION: Synthetic construct

<400> SEQUENCE: 48
ctttactagg agacgccaat a                                            21
```

ANTIBODIES AND VACCINES FOR USE IN TREATING ROR1 CANCERS AND INHIBITING METASTASIS

CROSS-REFERENCE TO RELATED APPLICATIONS

This application is a continuation of U.S. application Ser. No. 15/619,119, filed Jun. 9, 2017, which is a continuation of U.S. application Ser. No. 14/422,519, filed Feb. 19, 2015, which is a 35 USC § 371 National Stage application of International Application No. PCT/US2013/032572, filed Mar. 15, 2013, which claims the benefit under 35 U.S.C. § 119(e) to U.S. Application Ser. No. 61/709,803, filed Oct. 4, 2012, U.S. Application Ser. No. 61/709,055, filed Oct. 2, 2012 and to U.S. Application Ser. No. 61/693,230, filed Aug. 24, 2012. The disclosure of each of the prior applications is considered part of and is incorporated by reference in the disclosure of this application.

GRANT INFORMATION

This invention was made with government support under CA081534 and CA049870 awarded by the National Institutes of Health. The government has certain rights in the invention.

SEQUENCE LISTING

The material in the accompanying Sequence Listing is hereby incorporated by reference in its entirety. The accompanying file, named "ST-UCSD3820-1WO_ST25.txt", was created on Mar. 14, 2013 and is 33,125 bytes. The file can be accessed using Microsoft Word on a computer that uses Windows OS.

FIELD OF THE INVENTION

The invention relates generally to receptor tyrosine kinase-like orphan receptor 1 antibodies and vaccines, as well as methods for inhibiting metastasis.

BACKGROUND INFORMATION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. Receptor tyrosine kinases (RTKs) play critical roles in cell differentiation, proliferation, migration, angiogenesis, and survival. The receptor tyrosine kinase-like orphan receptor 1 (ROR1) is an evolutionarily-conserved type I membrane protein that belongs to the ROR subfamily and has extracellular domains that contain immunoglobulin (Ig)—like, Frizzled, and Kringle domains. ROR1-deficient mice display a variety of phenotypic defects within the skeletal and urogenital systems, as well as postnatal growth retardation. ROR1 is expressed during embryogenesis and by a variety of different cancers, but not by normal post-partum tissues, and can be considered an onco-embryonic surface antigen. Functional data suggest that ROR1 may function in non-canonical WNT-signaling to promote the survival of malignant cells. More recent studies have shown that non-canonical WNT signaling plays a major role in basal-like and other subtypes of breast cancer metastasis. Expression of ROR1 human breast cancer is also associated with activation of the AKT-CREB pathway and enhanced tumor-cell growth.

Receptor-tyrosine kinase like orphan receptor 1 (ROR1) is a conserved embryonic protein whose expression becomes progressively reduced during embryonic development in mammals. The intact protein, including its extracellular domain, does not appear to be significantly expressed in normal, adult mammal tissues. In particular, studies have not identified significant expression of ROR1 on the cell surface of normal adult human tissues, including normal, non-cancerous B cells (Baker et al., Clin. Cancer Res., 14:396 (2008); DaneshManesh et al., Int. J. Cancer, 123:1190 (2008) and Fukuda et al., Proc. Nat'l. Acad. Sci. USA, 105:3047 (2008)). However, ROR1 is expressed on the cell surface of malignant B-cells (B-CLL) and mantle cell lymphoma (MCL). It has also been reported that ROR1 is expressed in certain other cancer cell lines including Burkett's lymphoma, renal cell carcinoma, colon cancer and breast cancer (U.S. Patent Application 2007/02075110). Therefore, ROR1 can be considered a selective marker for these cancers.

SUMMARY OF THE INVENTION

The invention provides antibodies against ROR1 that can inhibit cancer cell growth and metastasis. This invention provides antibodies against ROR1, ROR1 binding peptides and ROR1 peptide vaccines. Further provided are compositions and methods for inhibiting metastasis using anti-ROR1 antibodies or antigen binding fragments thereof, ROR1 antibody immunoconjugates, ROR1 peptide vaccines or ROR1 binding peptides. In one embodiment, the invention provides for an isolated anti-human ROR1 antibody having the same binding specificity as antibody 99961. In one aspect, the antibody binds to the Ig-like domain, which is contiguous with the CRD domain of human ROR-1 (hROR1). In an additional aspect, the antibody binds to an epitope mapping to amino acids 42-160 of hROR-1. In a further aspect, the antibody binds to an epitope mapping to amino acids 130-160 of hROR-1. In another aspect, the antibody requires the presence of glutamic acid at position 138 of hROR-1 for binding.

In an additional embodiment, the invention provides for an isolated anti-human ROR1 antibody comprising a heavy chain variable region that is selected from the group consisting of SEQ ID. NO:1, SEQ ID. NO:5, SEQ ID. NO:9, SEQ ID. NO:13, and SEQ ID. NO:17, and the light chain variable region is selected from the group consisting of SEQ ID. NO:3, SEQ ID. NO:7, SEQ ID. NO:11, SEQ ID. NO:15 and SEQ ID. NO:19. In one aspect, the antibody according the heavy chain variable region is SEQ ID NO:5 and the light chain variable region is SEQ ID NO:7.

In one embodiment, the invention provides for an isolated anti-human ROR1 antibody comprising a heavy chain variable region comprised of CDR1, CDR2 and CDR3 selected from the group consisting of SEQ ID. NO:27, SEQ ID. NO:28, SEQ ID. NO:29, SEQ ID. NO:33, SEQ ID NO:34 and SEQ ID. NO:35, and the light chain variable region comprised of CDR1, CDR2 and CDR3 selected from the group consisting of SEQ ID. NO:30, SEQ ID. NO:31, SEQ ID. NO:32, SEQ ID. NO:36, SEQ ID NO:37 and SEQ ID. NO:38. In one aspect the a heavy chain variable region comprised of CDR1, CDR2 and CDR3 is comprised of SEQ ID. NO:27, SEQ ID. NO:28 and SEQ ID. NO:29, and the light chain variable region comprised of CDR1, CDR2 and CDR3 selected from the group consisting of SEQ ID. NO:30, SEQ ID. NO:31 and SEQ ID. NO:32.

In a further embodiment, the invention provides for an anti-human ROR-1 antibody with a binding affinity greater than 41 nM. In an aspect, the antibody binding affinity is between about 500 pM and about 6 nM. In one aspect, the antibody binding affinity is about 800 pM.

In another aspect, the antibody inhibits metastasis. In an additional aspect, the antibody internalizes and inhibits cell migration. In a further aspect, the antibody internalizes and down modulates vimentin, snail1/2, or ZEB. In a preferred aspect, the antibody is human, humanized, or chimeric.

In another embodiment, the invention provides for a pharmaceutical formulation comprising the antibody against ROR1 and a pharmaceutically acceptable carrier.

A further embodiment provides an isolated nucleic acid encoding the antibody against ROR1. In another embodiment, the invention provides for an expression vector comprising a nucleic acid encoding an antibody against hROR1. In an additional embodiment, the invention provides for a host cell comprising the nucleic acid encoding an antibody against hROR1. In a further embodiment, the invention provides for a method of producing an anti-human ROR1 antibody comprising culturing the host cells under conditions to produce the antibody, then optionally recovering the antibody.

In one embodiment the invention provides for a vaccine against ROR-1 expressing cells, the vaccine comprising a pharmaceutically acceptable composition of an isolated or synthetically produced peptide having an amino acid sequence with at least 95% sequence identity to the ROR-1 binding region of antibody D10. In one aspect, the amino acid sequence of the ROR-1 binding region of antibody D10 is VATNGKEVVSSTGVLFVKFGPC (SEQ ID NO:25). In a further aspect, the amino acid sequence of the ROR-1 binding region of antibody D10 is EVVSSTGVLFVKFGPC (SEQ ID NO:26). In another aspect, the ROR-1 expressing cell is a cancer cell. In an additional aspect, cancer cell is B cell leukemia, lymphoma, CLL, AML, B-ALL, T-ALL, ovarian, colon, lung, skin, pancreatic, testicular, bladder, uterine, prostate, or adrenal cancer.

In another embodiment, the invention provides for a vaccine comprising a ROR1 binding peptide having an amino acid sequence with at least 95% sequence identity to VATNGKEVVSSTGVLFVKFGPC (SEQ ID NO:25) and a pharmaceutically acceptable carrier. In one aspect, the peptide is mammalian. In an additional aspect, the ROR1 binding peptide is chimeric and/or of human, mouse, rat, porcine, bovine, primate, feline, canine, rabbit, goat, chicken or ursine origin. In another aspect, the vaccine further comprises an immunogenic adjuvant. In a further aspect, the adjuvant is an immunogenic carrier moiety conjugated to the binding peptide. In one aspect, the amino acid sequence of the binding peptide is VATNGKEVVSSTGVLFVKFGPC (SEQ ID NO:25). In another aspect, the immunogenic carrier moiety is a carrier peptide, such as keyhole limpet hemocyanin (KLH), bovine serum albumin (BSA), ovalbumin, aluminum hydroxide or other pharmaceutically acceptable immune adjuvant. Examples of pharmaceutically acceptable immune adjuvants can be found in Methods in Molecular Medicine, Vol. 42: Vaccine adjuvants: Preparation, Methods and Research Protocols; Edited by D. T. O'Hagan; Humana Press Inc., Totowa N.J. and European Agency for the Evaluation of Medicinal Products, Committee for Proprietary Medicinal Products, Guidelines on Adjuvants in Vaccines, London 2004.

In another embodiment, the invention provides for a vaccine comprising a ROR1 binding peptide having an amino acid sequence with at least 95% sequence identity to EVVSSTGVLFVKFGPC (SEQ ID NO:26) and a pharmaceutically acceptable carrier. In an additional aspect, the ROR1 binding peptide is chimeric and/or of human, mouse, rat, porcine, bovine, primate, feline, canine, rabbit, goat, chicken or ursine origin. In a further aspect, the adjuvant is an immunogenic carrier moeity conjugated to the binding peptide. In one aspect, the amino acid sequence of the binding peptide is VATNGKEVVSSTGVLFVKFGPC (SEQ ID NO:25). In another aspect, the immunogenic carrier moiety is a carrier peptide, such as keyhole limpet hemocyanin (KLH), bovine serum albumin (BSA ovalbumin, aluminum hydroxide or other pharmaceutically acceptable immune adjuvant. Examples of pharmaceutically acceptable immune adjuvants can be found in Methods in Molecular Medicine, Vol. 42: Vaccine adjuvants: Preparation, Methods and Research Protocols; Edited by D. T. O'Hagan; Humana Press Inc., Totowa N.J. and European Agency for the Evaluation of Medicinal Products, Committee for Proprietary Medicinal Products, Guidelines on Adjuvants in Vaccines, London 2004.

In an additional embodiment, the invention provides for a pharmaceutical formulation comprising the vaccine comprising a ROR1 binding peptide having an amino acid sequence with at least 95% sequence identity to VATNGKEVVSSTGVLFVKFGPC (SEQ ID NO:25) and a pharmaceutically acceptable carrier.

In an additional embodiment, the invention provides for a pharmaceutical formulation comprising the vaccine comprising a ROR1 binding peptide having an amino acid sequence with at least 95% sequence identity to EVVSSTGVLFVKFGPC (SEQ ID NO:26) and a pharmaceutically acceptable carrier.

In one embodiment, the invention provides for a ROR1 binding peptide comprising the amino acid sequence selected from the group consisting of: SEQ ID NO:25 and SEQ ID NO:26. In one aspect, the peptide has an amino acid sequence with at least 95% sequence identity to VATNGKEVVSSTGVLFVKFGPC (SEQ ID NO:25). In another aspect, the peptide has an amino acid peptide sequence at least 95% sequence identity to EVVSSTGVLFVKFGP (SEQ ID NO:26)C. In another aspect, the binding peptide is mammalian. In an additional aspect, the binding peptide is chimeric and/or of human, mouse, rat, porcine, bovine, primate, feline, canine, rabbit, goat, chicken or ursine origin.

In an embodiment, the invention provides for a pharmaceutical formulation comprising a ROR1 binding peptide comprising the amino acid sequence selected from the group consisting of: SEQ ID NO:25 and SEQ ID NO:26 and a pharmaceutically acceptable carrier.

In another embodiment, the invention provides for an isolated nucleic acid encoding a ROR1 binding peptide comprising the amino acid sequence of SEQ ID NO:25 and SEQ ID NO:26. In another embodiment, the invention provides for an expression vector comprising the nucleic encoding a ROR1 binding peptide comprising the amino acid sequence of SEQ ID NO:25 and SEQ ID NO:26. In a further embodiment, the invention provides for a host cell comprising the nucleic acid encoding a ROR1 binding peptide comprising the amino acid sequence of SEQ ID NO:25 and SEQ ID NO:26. In an additional embodiment, the invention provides for a method of producing a peptide comprising culturing the host cell encoding a ROR1 binding peptide comprising the amino acid sequence of SEQ ID NO:25 and SEQ ID NO:26 under conditions to produce the binding peptide. In one aspect, the method to produce a peptide further comprising recovering the binding peptide.

In one embodiment, the invention provides for a method of suppressing metastasis of ROR-1 expressing cancer, the method comprising disrupting epithelial-mesenchymal transition of tumor cells by administering an antibody having the binding specificity of monoclonal antibody 99961, a vaccine comprised of a peptide having an amino acid sequence with at least 95% sequence identity to the ROR-1 binding region of antibody D10 or a ROR-1 binding peptide having an amino acid sequence with at least 95% sequence identity to VATNGKEVVSSTGVLFVKFGPC (SEQ ID NO:25). In one aspect, the ROR-1 expressing cancer is B cell leukemia, lymphoma, CLL, AML, B-ALL, T-ALL, ovarian, colon, lung, skin, pancreatic, testicular, bladder, uterine, prostate, or adrenal cancer.

In one embodiment, the invention provides for a method of suppressing metastasis of ROR-1 expressing cancer, the method comprising disrupting epithelial-mesenchymal transition of tumor cells by administering an antibody having the binding specificity of monoclonal antibody 99961, a vaccine comprised of a peptide having an amino acid sequence with at least 95% sequence identity to the ROR-1 binding region of antibody D10 or a ROR-1 binding peptide having an amino acid sequence with at least 95% sequence identity to EVVSSTGVLFVKFGPC (SEQ ID NO:26). In one aspect, the ROR-1 expressing cancer is B cell leukemia, lymphoma, CLL, AML, B-ALL, T-ALL, ovarian, colon, lung, skin, pancreatic, testicular, bladder, uterine, prostate, or adrenal cancer.

In an additional embodiment, the invention provides a method for treating or preventing a cancer in a subject, the method comprising administering to the subject an antibody having the binding specificity of monoclonal antibody 99961, a vaccine comprised of a peptide having an amino acid sequence with at least 95% sequence identity to the ROR-1 binding region of antibody D10 or a ROR-1 binding peptide having an amino acid sequence with at least 95% sequence identity to VATNGKEVVSSTGVLFVKFGPC (SEQ ID NO:25). In one aspect, the cancer is B cell leukemia, lymphoma, CLL, AML, B-ALL, T-ALL, ovarian, colon, lung, skin, pancreatic, testicular, bladder, uterine, prostate, or adrenal cancer.

In an additional embodiment, the invention provides a method for treating or preventing a cancer in a subject, the method comprising administering to the subject an antibody having the binding specificity of monoclonal antibody 99961, a vaccine comprised of a peptide having an amino acid sequence with at least 95% sequence identity to the ROR-1 binding region of antibody D10 or a ROR-1 binding peptide having an amino acid sequence with at least 95% sequence identity to EVVSSTGVLFVKFGPC (SEQ ID NO:26). In one aspect, the cancer is B cell leukemia, lymphoma, CLL, AML, B-ALL, T-ALL, ovarian, colon, lung, skin, pancreatic, testicular, bladder, uterine, prostate, or adrenal cancer.

(G) Left, histograms depicting the in vivo lung photon flux. Right, Representative H&E-stained sections of the lungs. (H) The graph depicts the normalized in vivo lung photon flux. (I) Representative bioluminescence images of tumor-injected mice treated with IgG (top) or D10 (bottom). (J) The histogram depicts the lung-weight-index. (K) Representative H&E-stained sections of the lungs. (L) Photomicrographs depict that when sacrificed at day 35, the lungs of mice treated with D10 had significantly fewer metastatic foci than the lungs of animals given control IgG. Data are shown as means±SEM; *P<0.05, P<0.01, *P<0.001, compared with IgG group.

Figure 6:
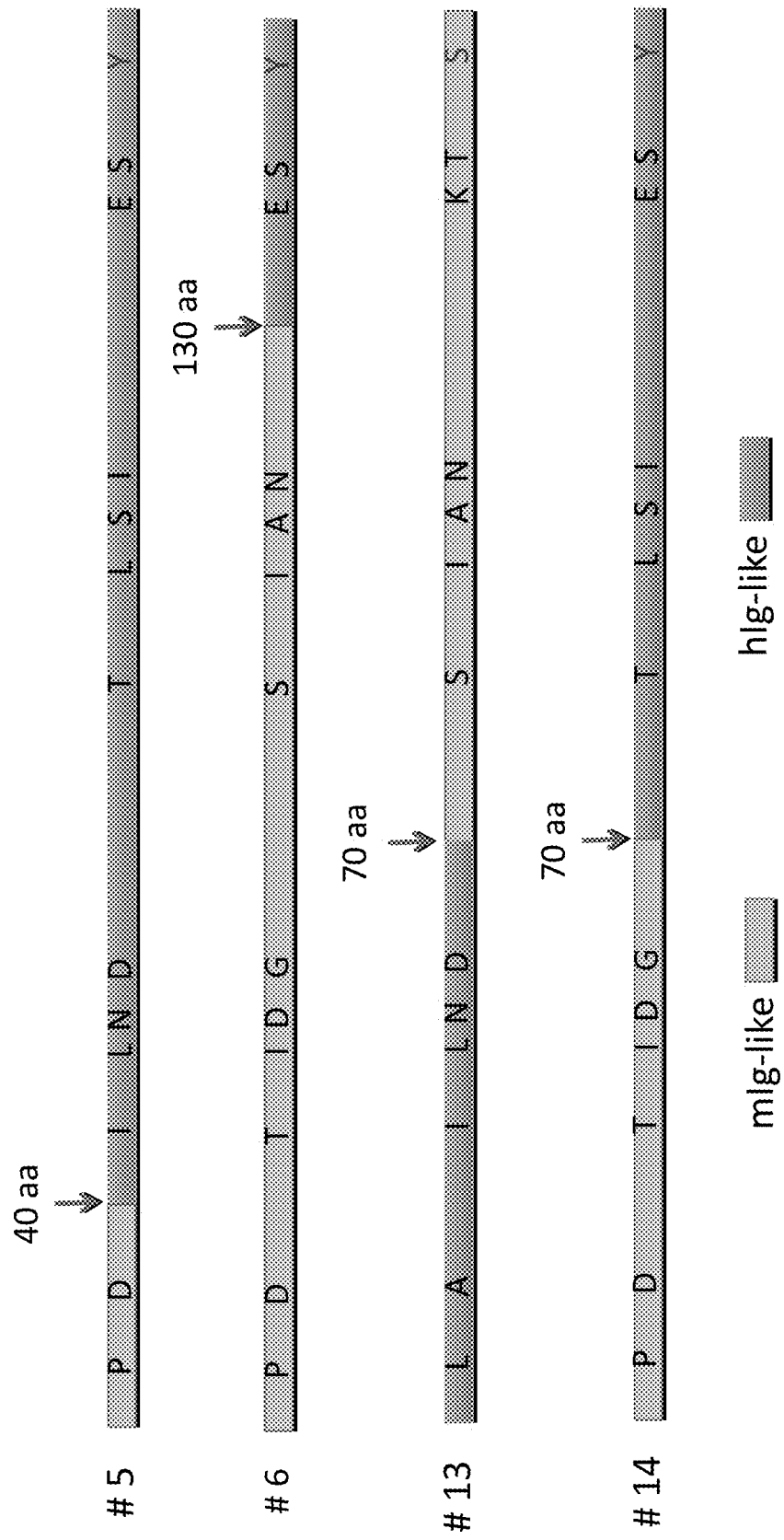

FIG. 6 shows the chimeric constructs used to map the epitope of ROR1 antibody D10. The light portion of the construct is mouse and the darker portion is human.

Figure 7:
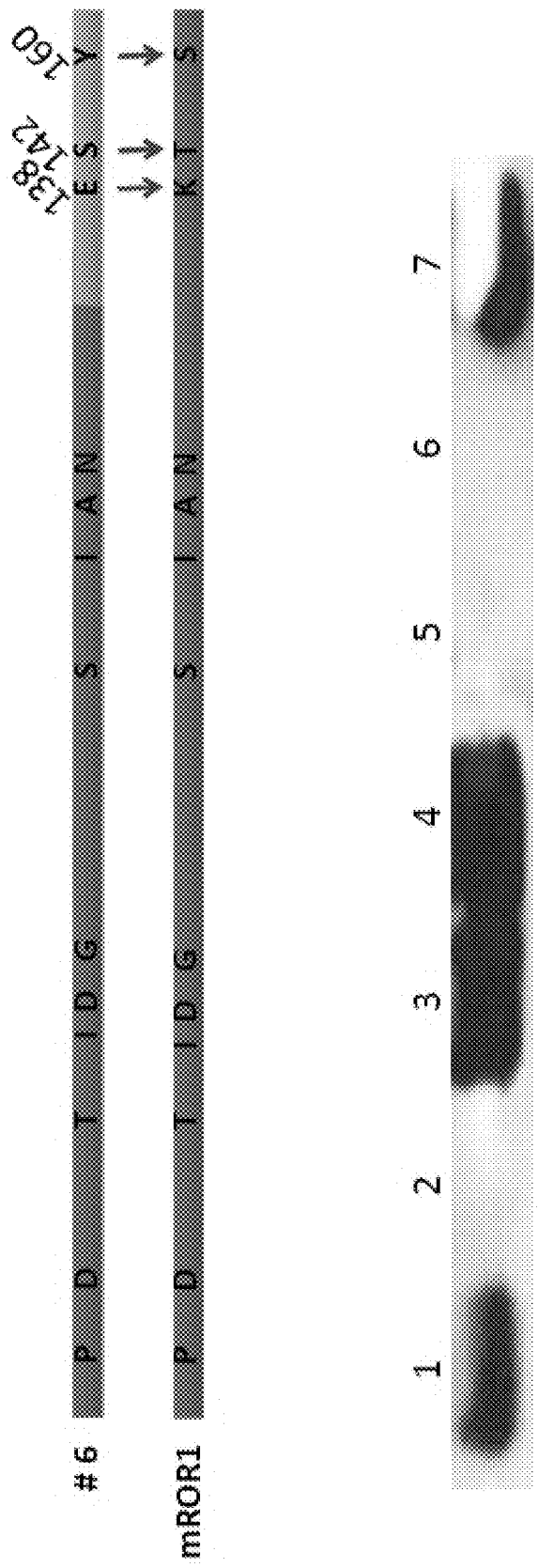

FIG. 7 depicts epitope mapping for the D10 antibody, which does not react with mouse ROR1 protein. The mouse or human ROR1 protein have the different amino acid residues at amino acid positions 138, 142, or 160; the human ROR1 protein has amino acid residues E, S, or Y, at these positions, whereas the mouse ROR1 protein has amino acid residues K, T, or S at amino acid positions 138, 142, or 160, respectively. We generated recombinant human ROR1 proteins having either the mouse or human amino acid residue at these positions only. These recombinant proteins were separated in non-denaturing polyacrylamide gel and then transferred onto nylon, which was probed with the D10 mAb. As can be seen in this figure, D10 reacts with recombinant proteins 1, 3, 4, and 7, but not 2, 5, or 6, which are described in the legend below. Note that substitution of the human amino acid residue E at position 138 of the human ROR1 protein with the mouse amino acid residue T at position 138 abrogates D10 binding.

Figure 8:
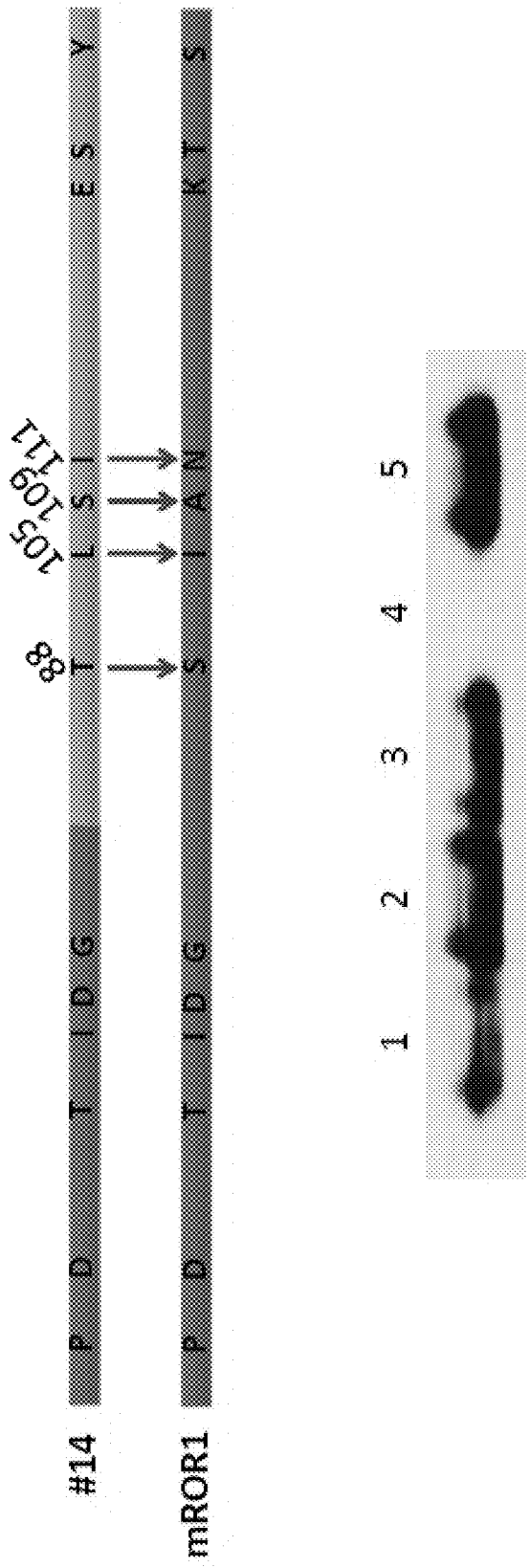

FIG. 8 shows epitope mapping for the anti-human ROR1 antibody 4A5. The mouse or human ROR1 protein have the different amino acid residues at amino acid positions 88, 105, 109, or 111; the human ROR1 protein has amino acid residues T, L, S, or I at these positions, whereas the mouse ROR1 protein has amino acid residues S, I, A, or N at amino acid positions 88, 105, 109, or 111, respectively. We generated recombinant human ROR1 proteins having either the mouse or human amino acid residue at these positions only. These recombinant proteins were separated in non-denaturing polyacrylamide gel and then transferred onto nylon, which was probed with the 4A5 mAb. As can be seen in this figure, 4A5 could bind to recombinant proteins 1, 2, 3, or 5, but not 4. Recombinant protein 4 is the human ROR1 protein but with the mouse amino acid residue N at position 111 instead of the amino acid residue I, which is found in the human ROR1 protein.

Figure 9:
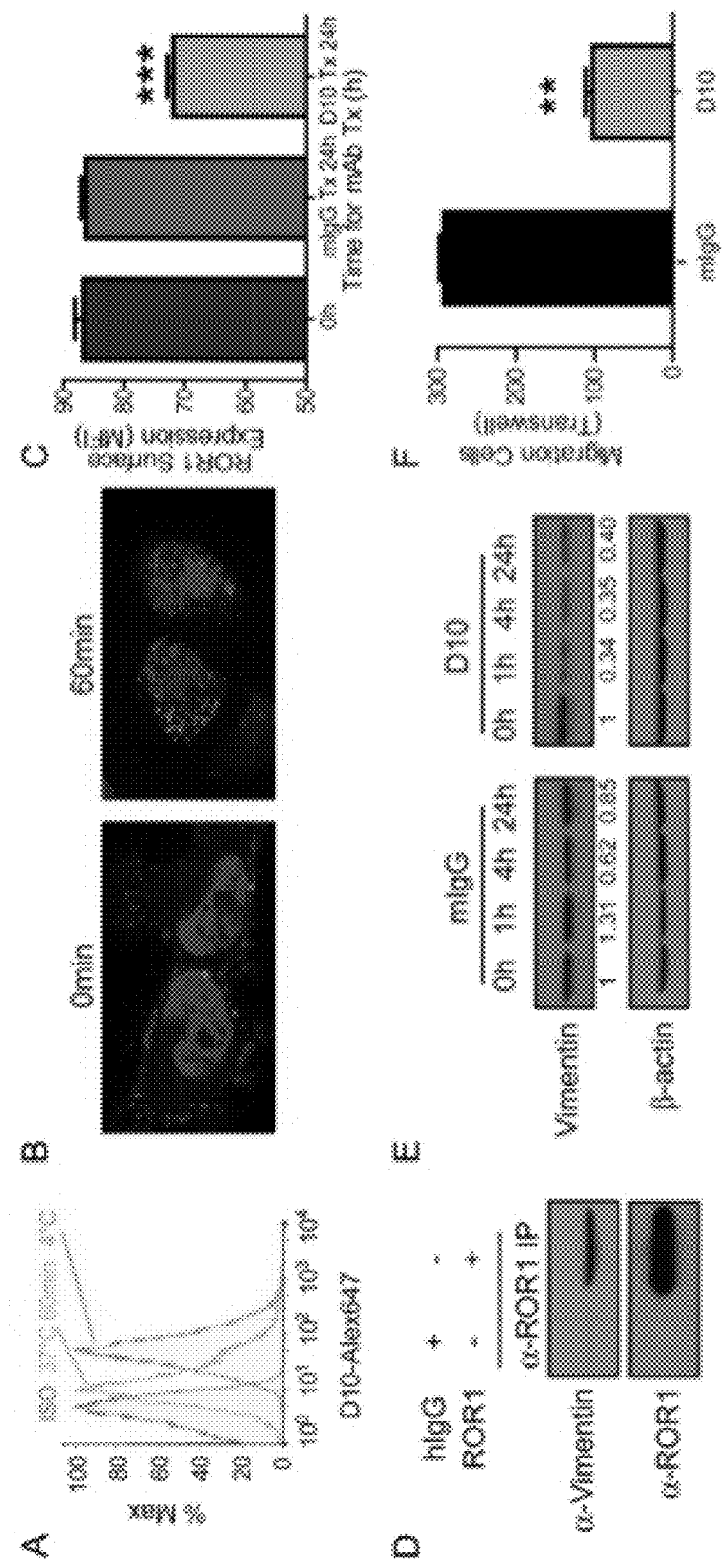
Figure 9:
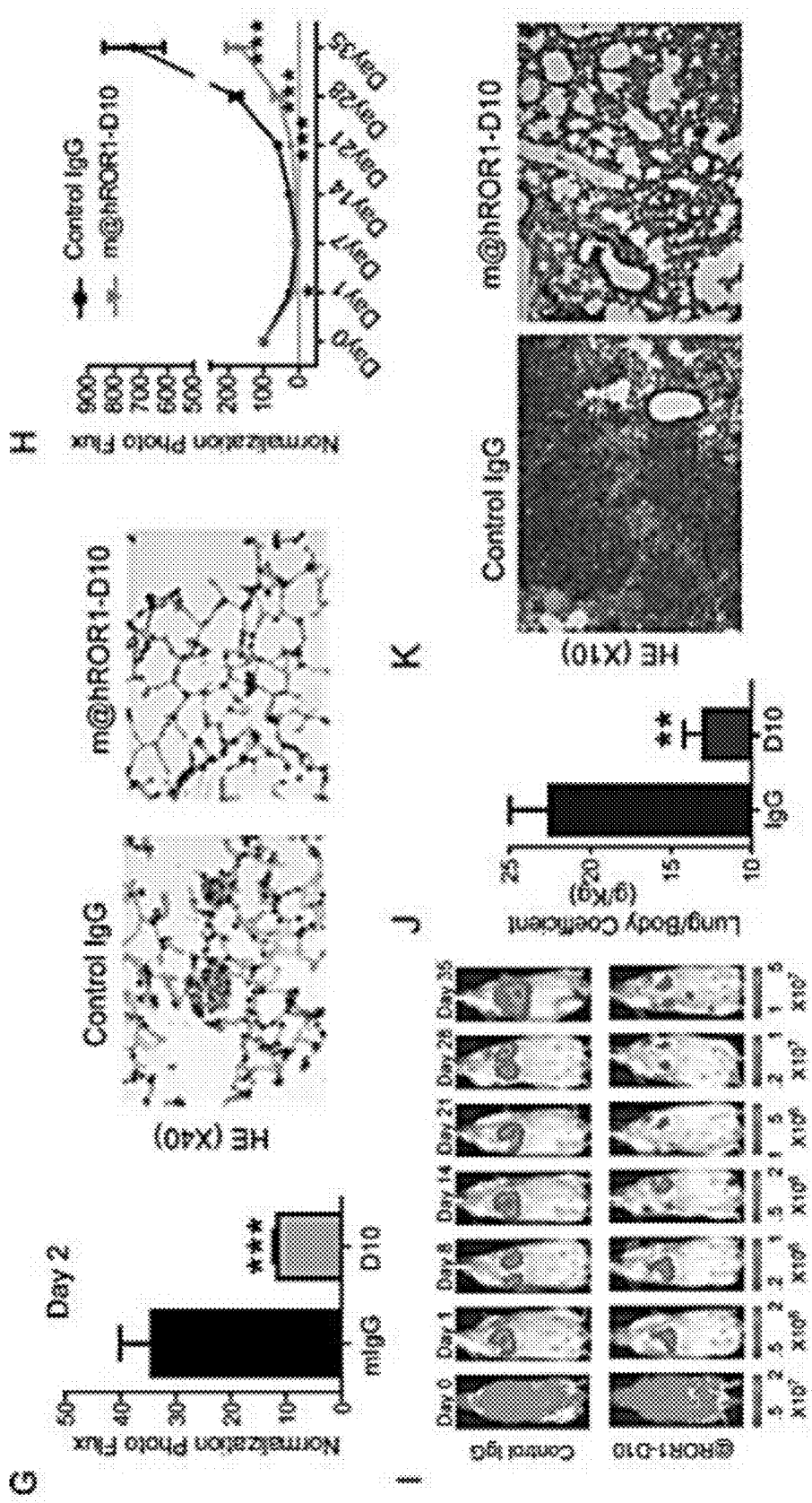

FIG. 9 demonstrates that anti-human ROR1 antibody D10 inhibits metastasis of breast cancer cells. A-B. The D10 monoclonal antibody facilitates ROR1 receptor internalization. C. 24 hours anti-ROR1 antibody D10 treatment decrease ROR1 surface expression in MDA-MB-231 cells. D. ROR1 forms complex with vimentin in breast cancer MDA-MB-231 cells. E. D10 antibody treatment in vitro could decrease vimentin expression. F. Anti-human ROR1 antibodies decrease breast cancer migration in vitro. G. The D10 monoclonal antibody inhibits MDA-MB-231 breast cancer early-stage (day 2) lung metastasis. H. The D10 monoclonal antibody inhibits MDA-MB-231 breast cancer lung metastasis. I. Representative mice injected with 5E5 MDA-MB-231 cells are shown in the dorsal position. J. Anti-human ROR1 antibody treatment reduced the lung weight of MDA-MB-231-bearing mice. K. Representative pulmonary H&E histology from MDA-MB-231-bearing mice after anti-ROR1 antibody treatment. The error bars indicate SEM; *p<0.05, **p<0.01; based on a unpaired two-sided student's t-test.

Figure 10:
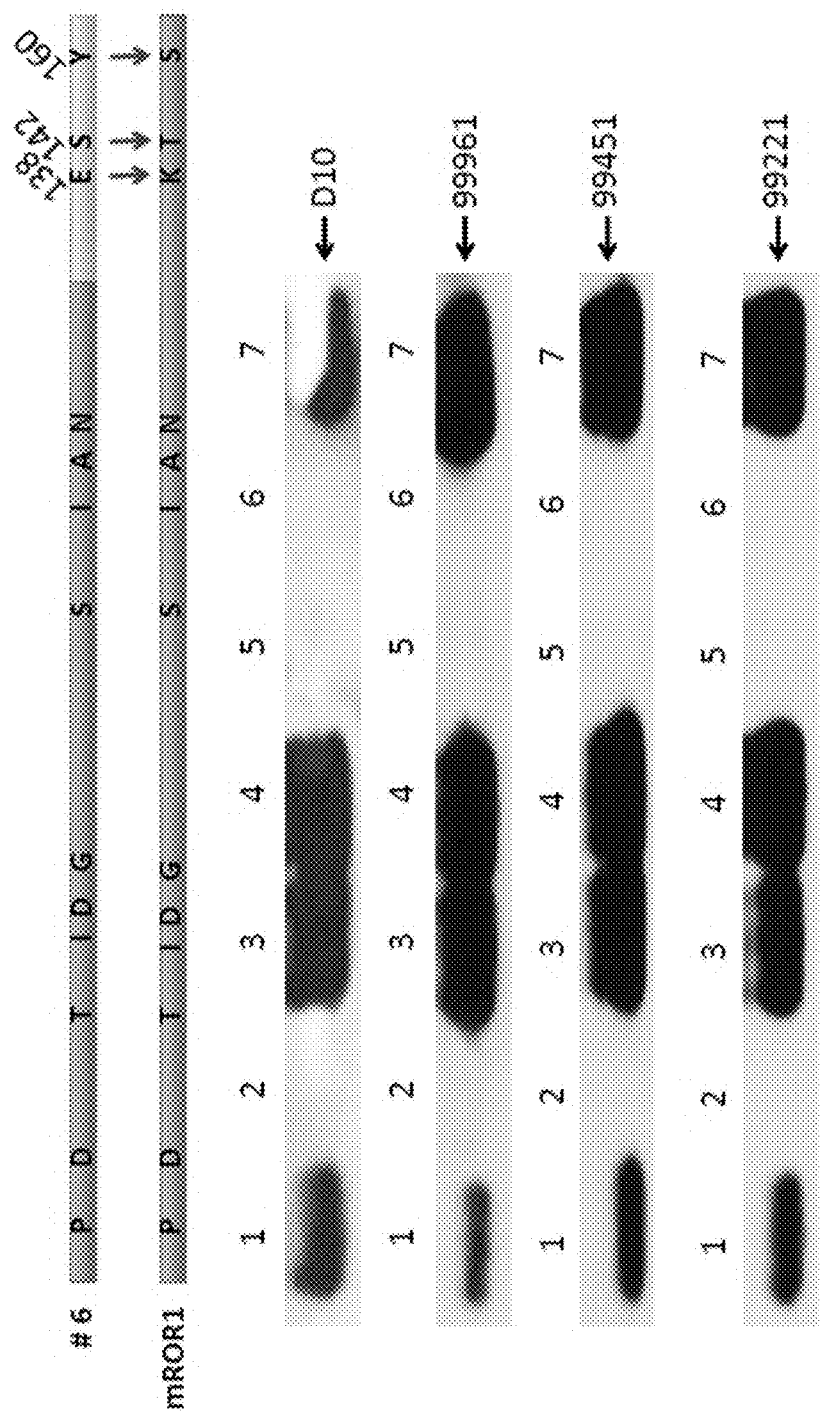

FIG. 10 depicts high affinity antibodies generated against the ROR1 epitope recognized by mAbs D10, 99451, 99961, or 99221. The mouse or human ROR1 protein have the different amino acid residues at amino acid positions 138, 142, or 160; the human ROR1 protein has amino acid residues E, S, or Y, at these positions, whereas the mouse ROR1 protein has amino acid residues K, T, or S at amino acid positions 138, 142, or 160, respectively. We generated recombinant human ROR1 proteins having either the mouse or human amino acid residue at these positions only. These recombinant proteins were separated in non-denaturing polyacrylamide gel and then transferred onto nylon, which was probed with the each of the three mAb, 99451, 99961, or 99221, as indicated on the left margin. As can be seen in this figure, each of these antibodies reacts with recombinant proteins 2, 4, 5, and 8, but not 2, 3, 6, or 7, which are described in the legend below. Note that substitution of the human amino acid residue E at position 138 of the human ROR1 protein with the mouse amino acid residue T at position 138 abrogates the binding of either 99451, 99961, or 99221.

Figure 11:
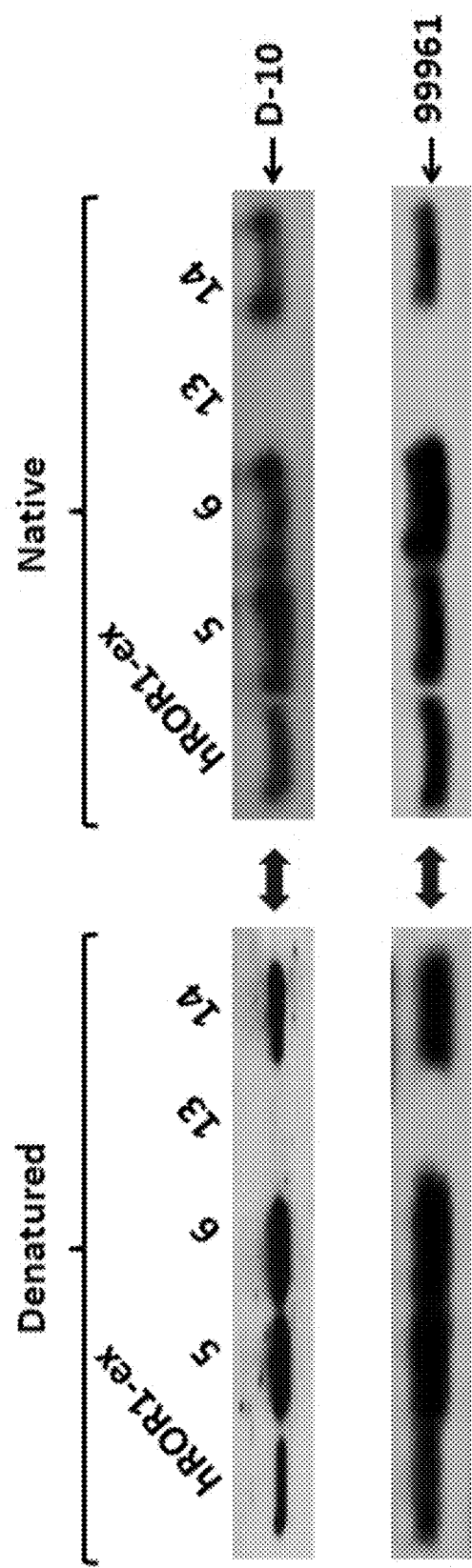

FIG. 11 depicts the binding activity of antibodies D10 or 99961 for wild-type or recombinant ROR1 protein. Vectors encoding the human or chimeric ROR1 protein were transfected into 293 cells. This allowed for production of recombinant human-mouse chimeric ROR1 protein that then could be size separated in a non-denaturing PAGE gel (right) or SDS-PAGE gel (left) for immunoblot analysis with different anti-ROR1 mAb. The results indicate that both D10 and 99961 antibodies bind to the same region, on the C-terminus of Ig-like domain, and that D10 and 99961 can bind to ROR1 under both denatured and native conditions. Note that D10 and 99961 bind to all recombinant proteins except for 13. The #13 chimeric protein is as described in FIG. 6. The full human extracellular domain is provided on the far left lane of either gel.

Figure 12:
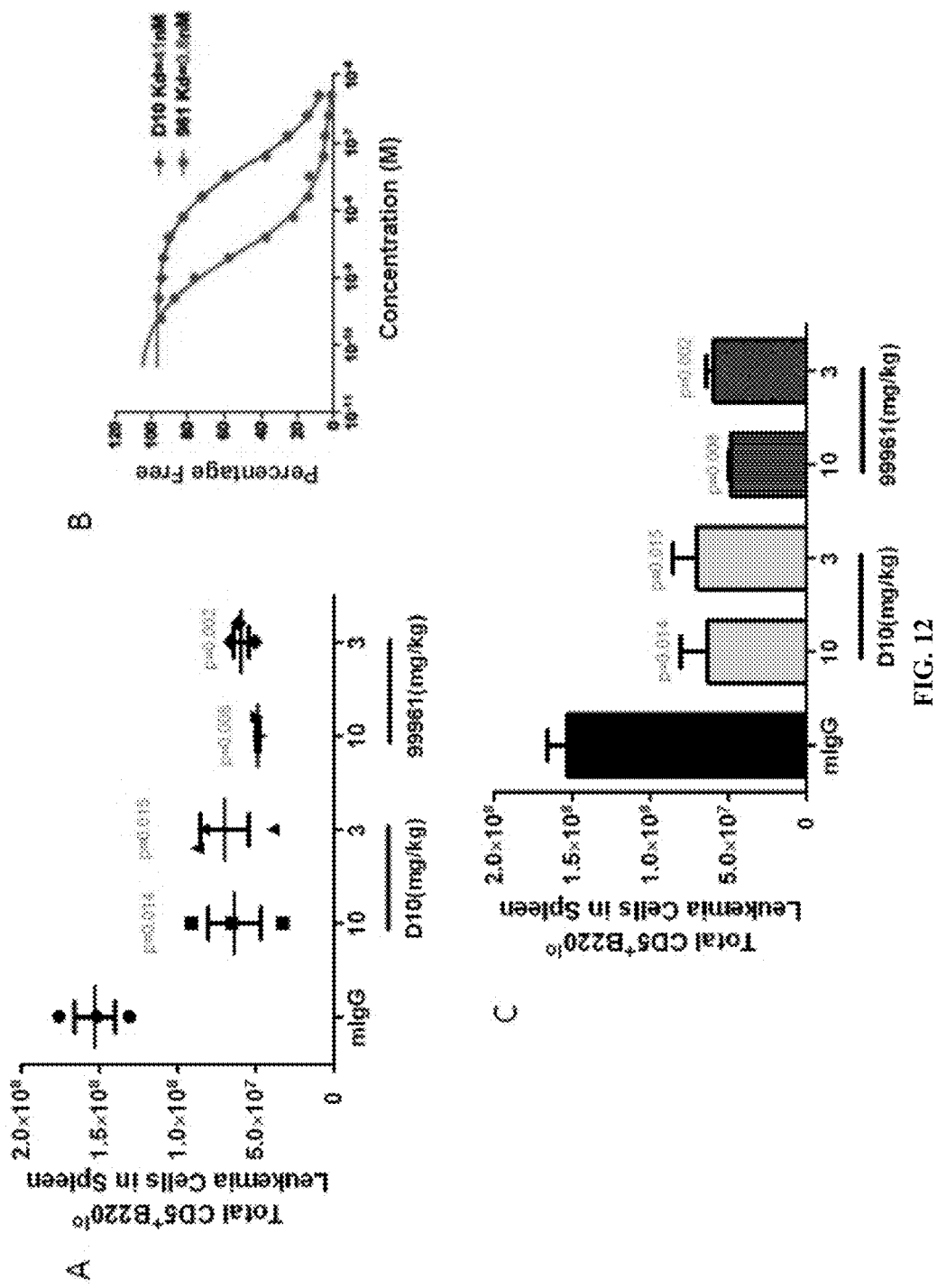

FIG. 12 shows characterization of anti-human ROR1 antibody 99961. A, B. the 99961 antibody was able to block CLL engraftment in transgenic mice. C. the 99961 antibody has a binding affinity approximately 50× greater than the D10 antibody.

Figure 13:
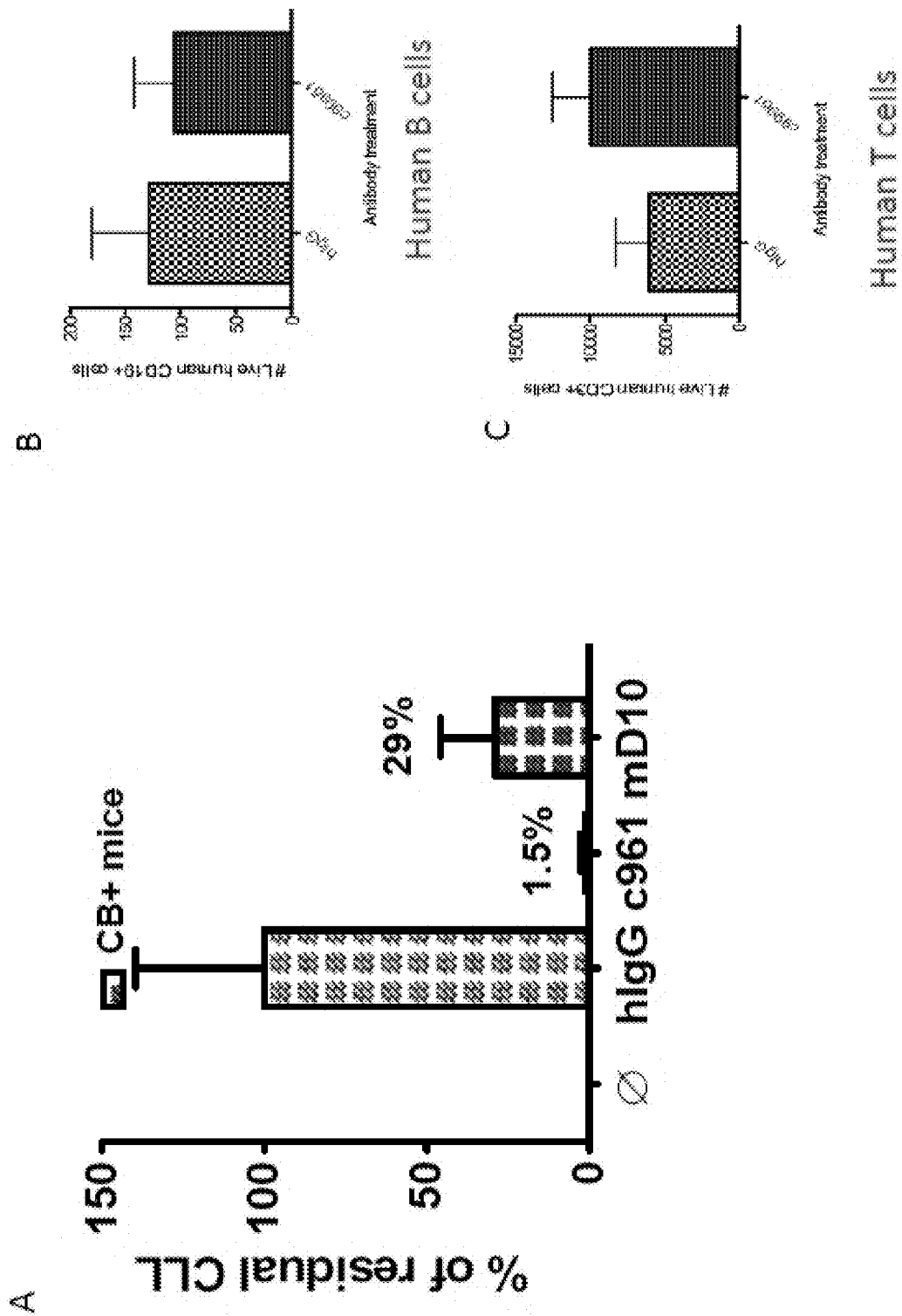

FIG. 13 shows the specific activity of 99961 against CLL cells in human cord blood reconstituted immune deficient mice. A. 99961 antibody eliminates >90% of CLL cells. B, C. 99961 antibody has no effect on normal B or T cell development.

Figure 14:
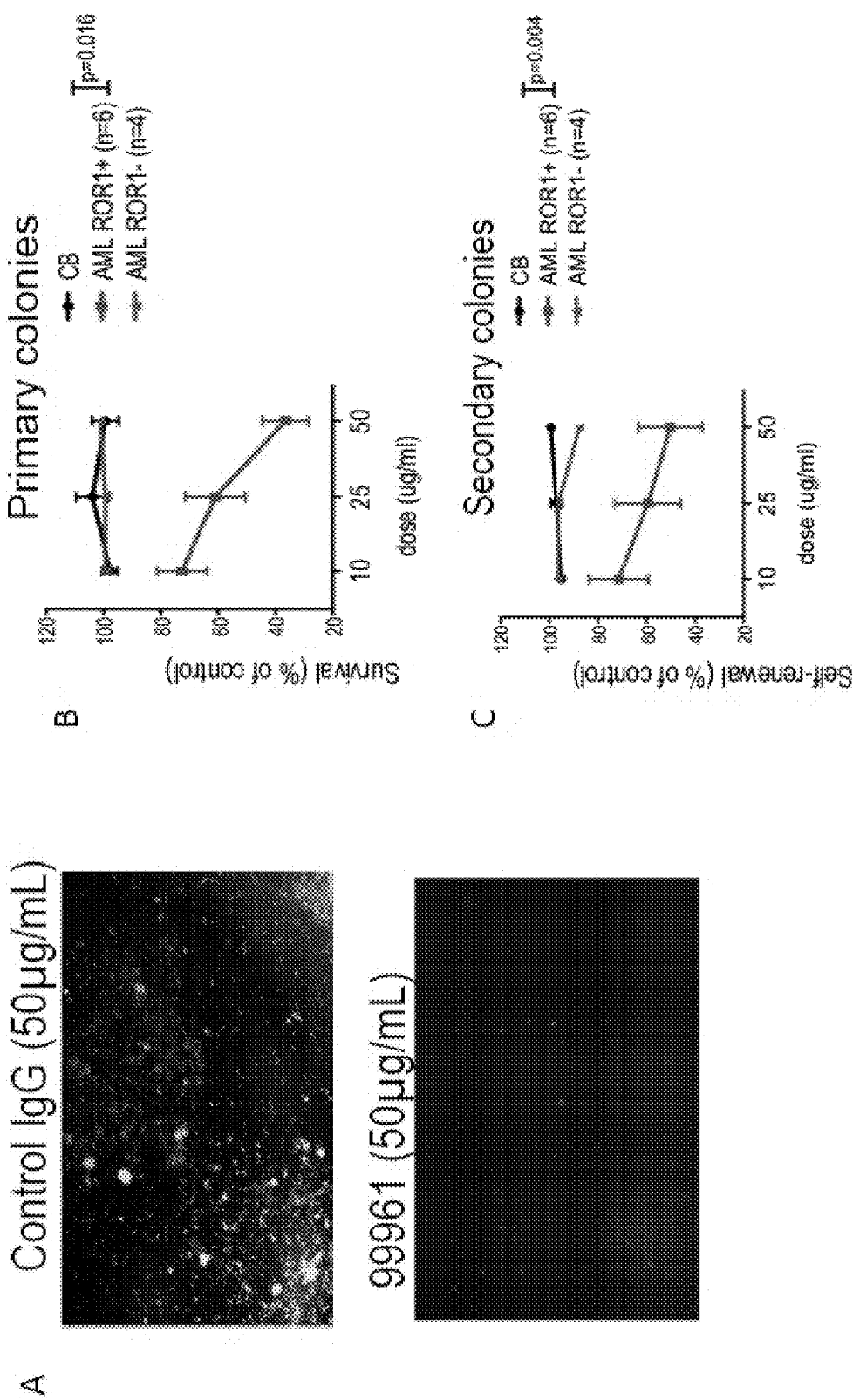

FIG. 14 shows the specific activity of 99961 in ROR+ primary AML. (A) Photomicrograph depicting control IgG (50 µg/mL) (top) and 99961 (50 µg/mL) (bottom). (B) Primary colonies survival (% of control) as a function of dose (µg/mL). (C) Secondary colonies, self-renewal (% of control (as a function of dose (µg/mL).

Figure 15:
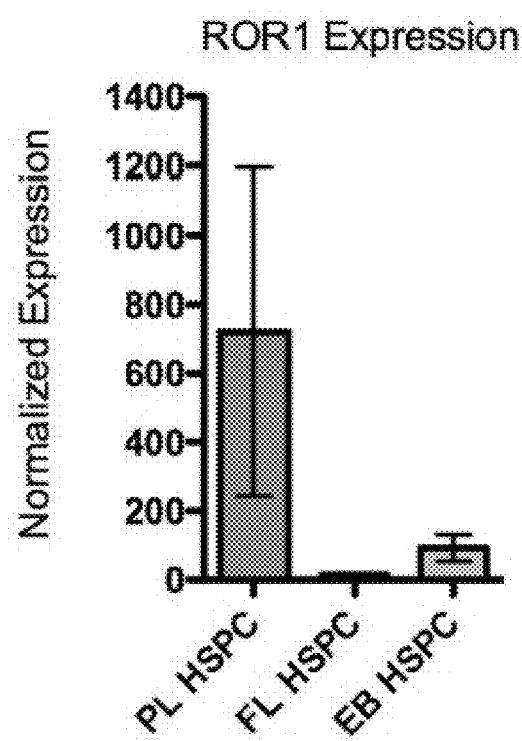

FIG. 15 shows that the epitope recognized by 99961 is not expressed by normal hematopoietic stem or progenitor cells.

Figure 16:
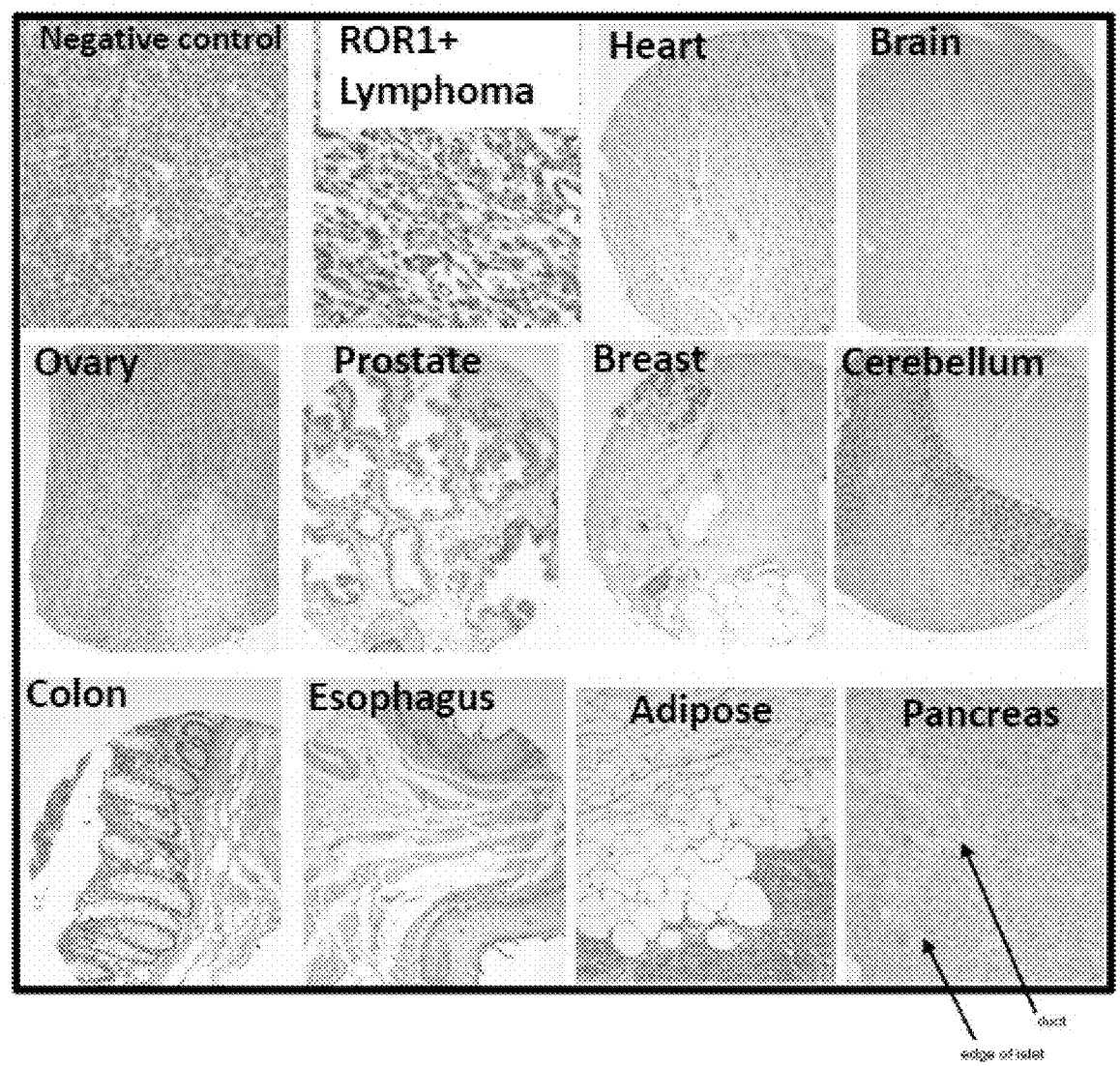

FIG. 16 shows that 99961 does not cross react with normal adult tissue.

Figure 17:
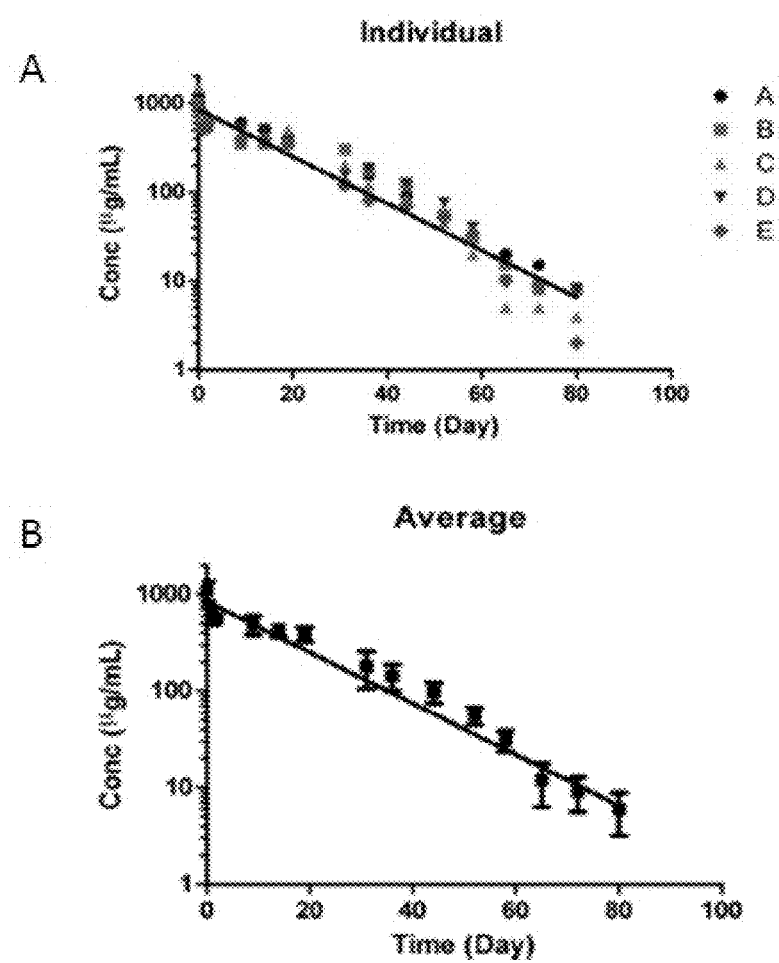

FIG. 17 shows PK studies on 99961 in immune deficient mice. Blood was drawn at different time points and levels of 99961 mAb in plasma were measured by ELISA. (A) Concentration of 99961 mAb in plasma in five individual test subjects as a function of time (days). (B) Average concentration of 99961 mAb in plasma for data set forth in (A).

Figure 18:
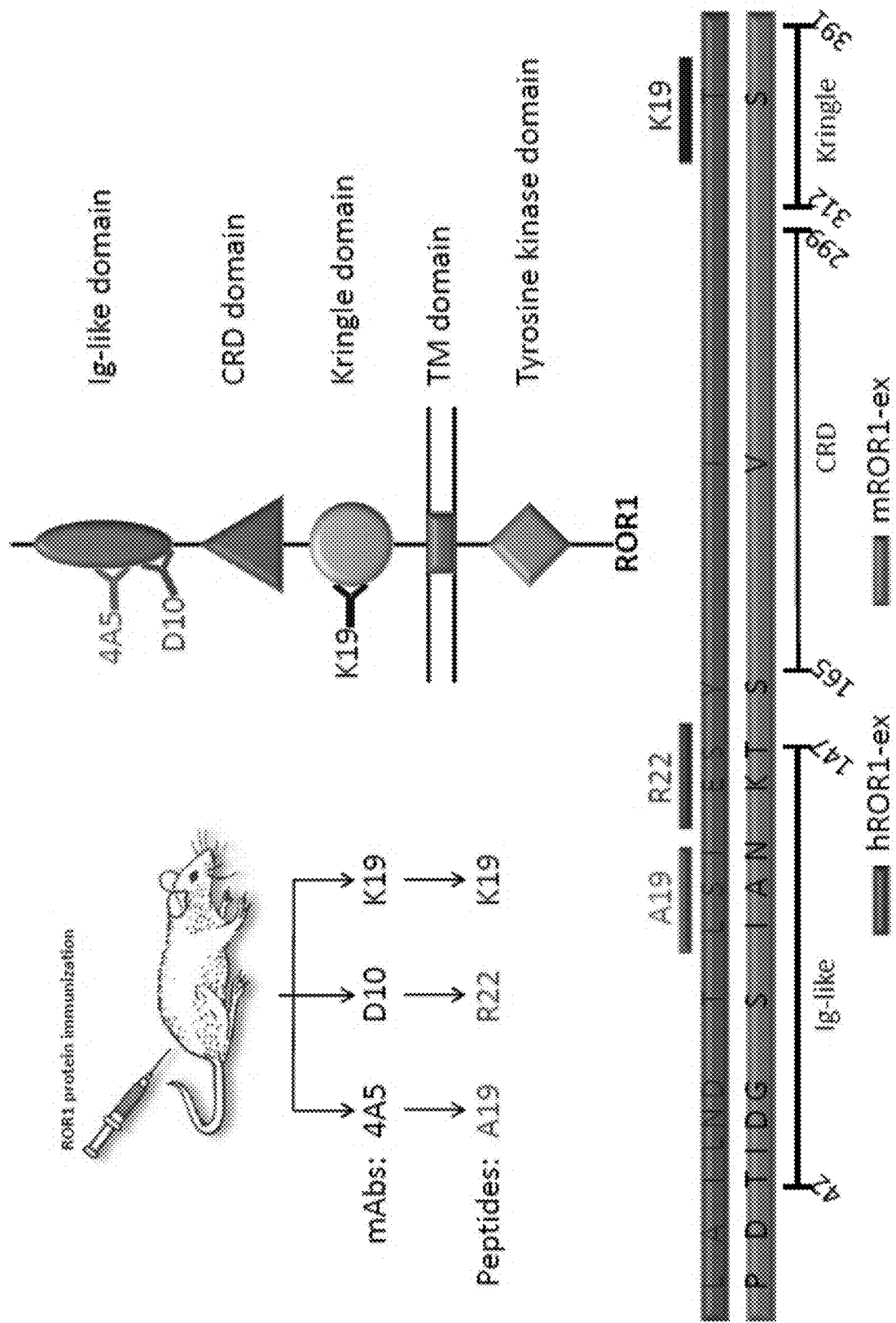

FIG. 18 illustrates design of a ROR1 peptide vaccine. Three different antibody epitopes were used to make peptides A19, R22 and K19. Above the bars that correspond to either the human (top) or mouse (bottom) ROR1, are bars labeled A19, R22, or K19. These bars describe the location of the peptides, A19, R22, or K19 in the ROR1 extracellular domain.

Figure 19:
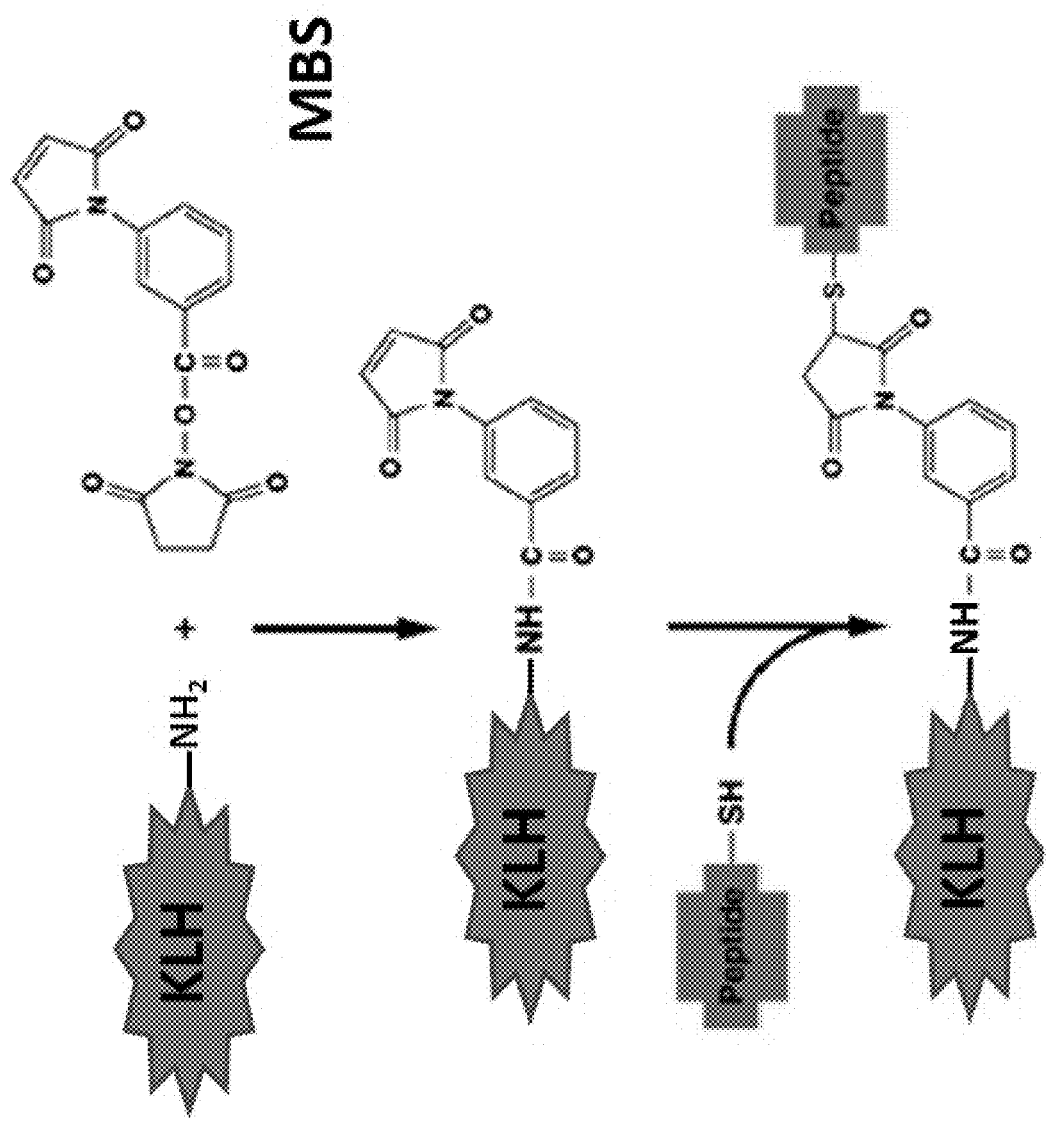

FIG. 19 shows the method used to conjugate KLH to the peptides.

Figure 20:
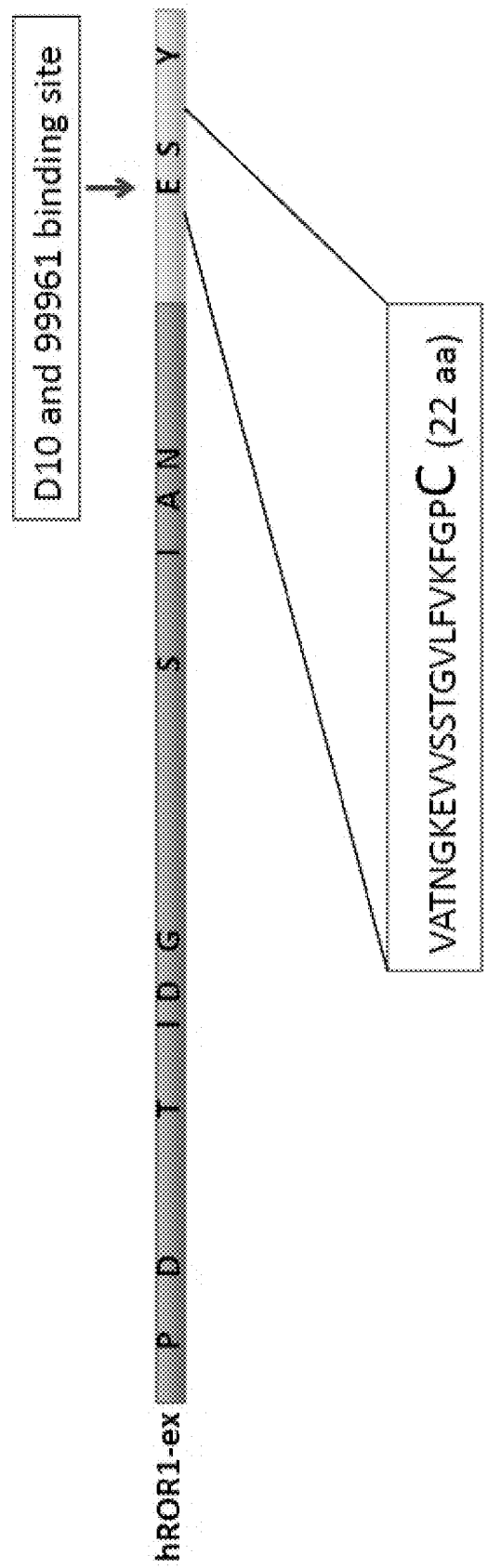

FIG. 20 shows the peptide design of peptide R22. A cysteine was added to the C-terminal of the peptide to be used to conjugate to KLH. Sequence legend:

```
                                    (SEQ ID NO: 25)
VATNGKEVVSSTGVLFVKFGPC
```

Figure 21:
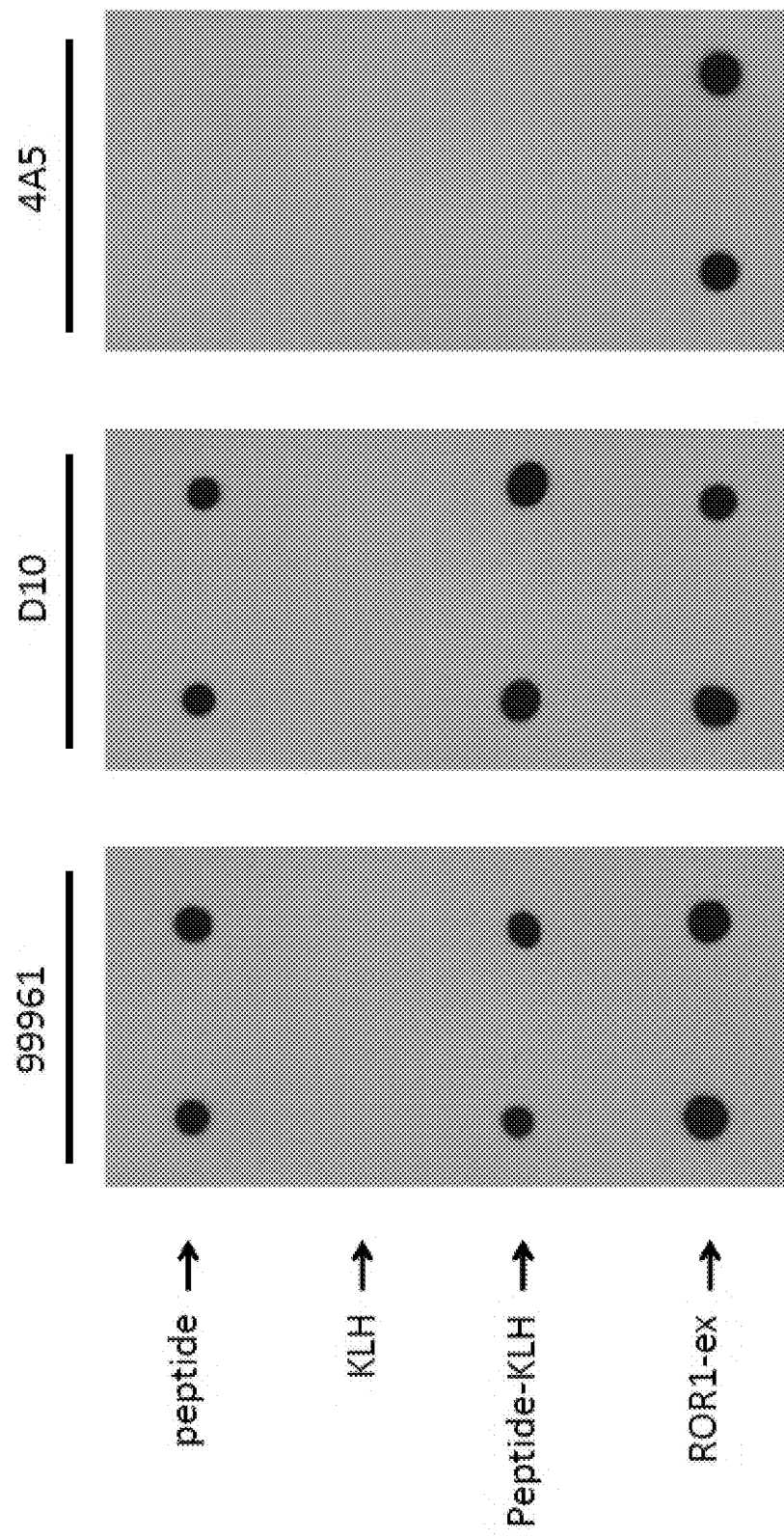

FIG. 21 shows that that D10 and 99961 bind to the R22 peptide while 4A5 does not.

Figure 22:
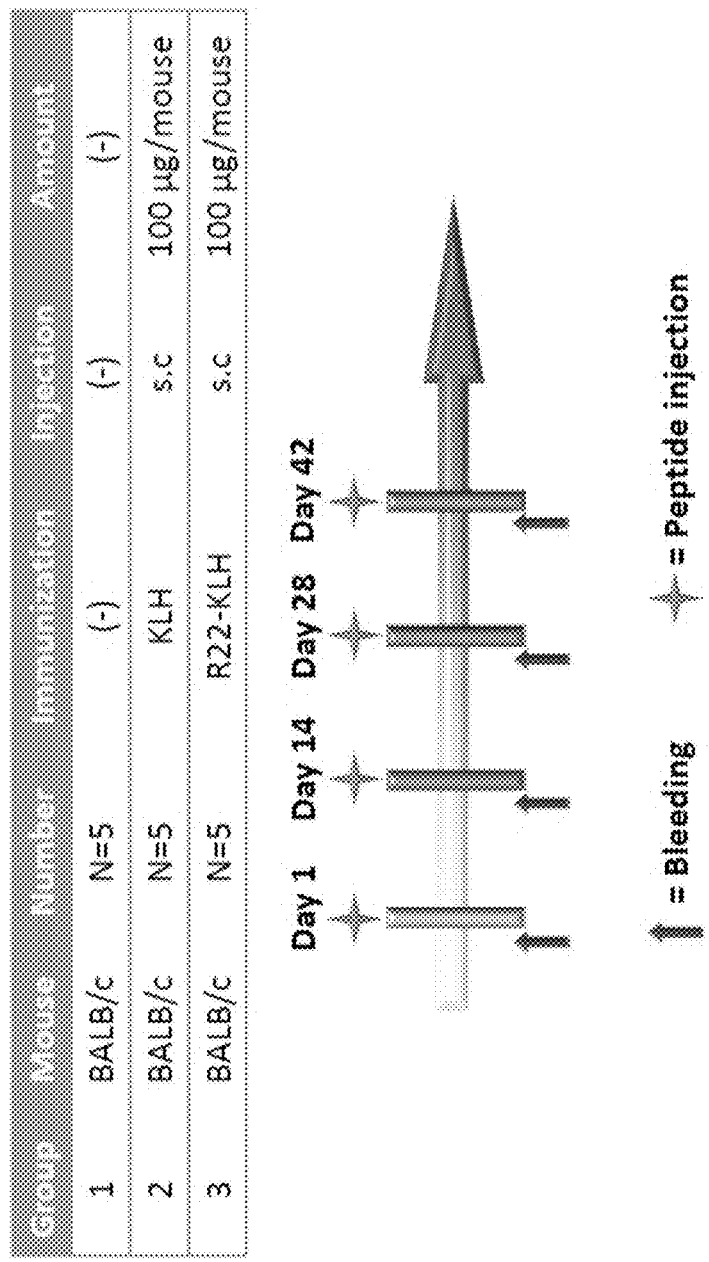

FIG. 22 shows the immunization scheme for R22 immunization of BALB/c mice.

Figure 23:
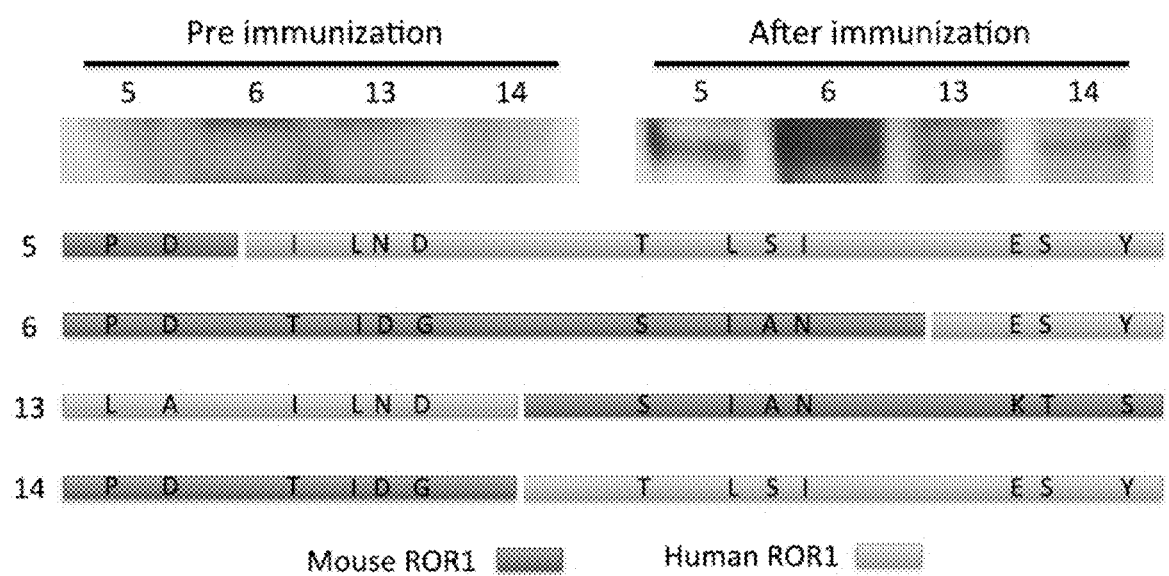

FIG. 23 shows immunoblot analysis of the epitope that the R22 induced ROR1 antibodies bind on ROR1.

Figure 24:
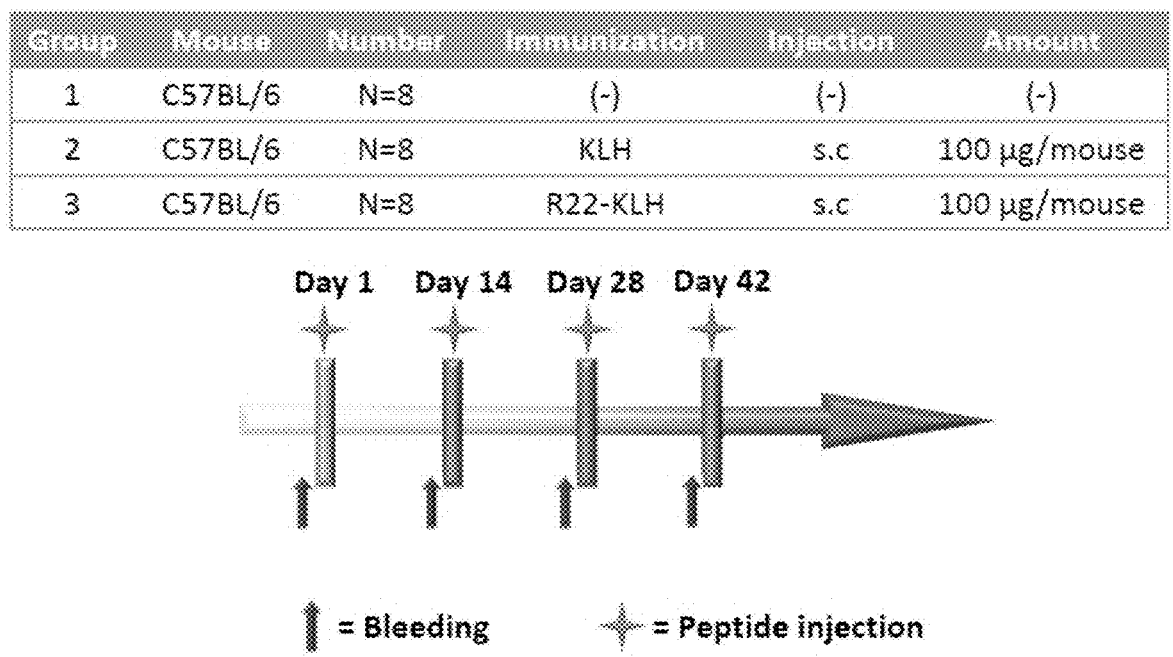

FIG. 24 shows the immunization scheme for R22-KLH in C57BL/6 mice.

Figure 25:
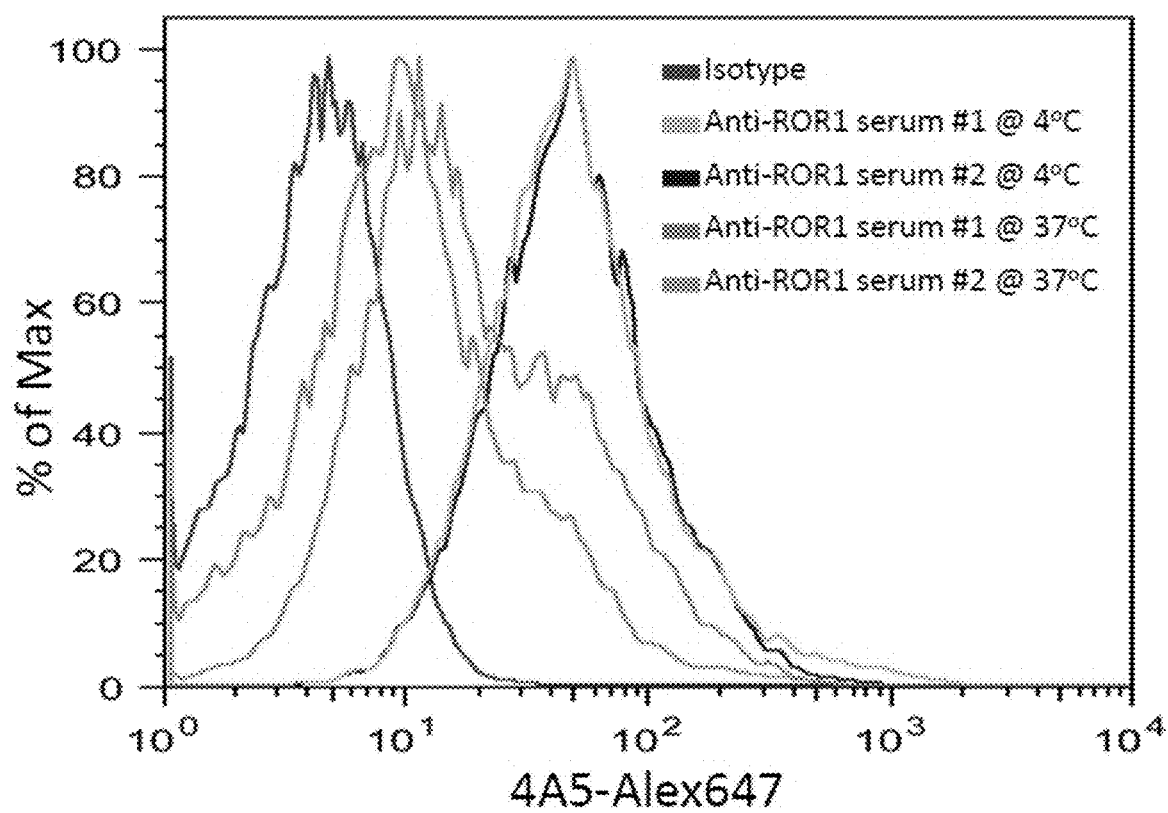

FIG. 25 shows FACS analysis of ROR1-positive MDA-MB-231 breast cancer cells that had been incubated with anti-R22-KLH antisera at 4° C. or 37° C. for 1 h and then counter-stained with isotype-control-Alexa647-labels antibody, or 4A5-Alexa647 conjugate for 30 min on ice prior to FACS analysis of ROR1 expression. The results showed that anti-ROR1 sera from transgenic mice induced ROR1 receptor internalization at 37° C., but not at 4° C.

Figure 26:
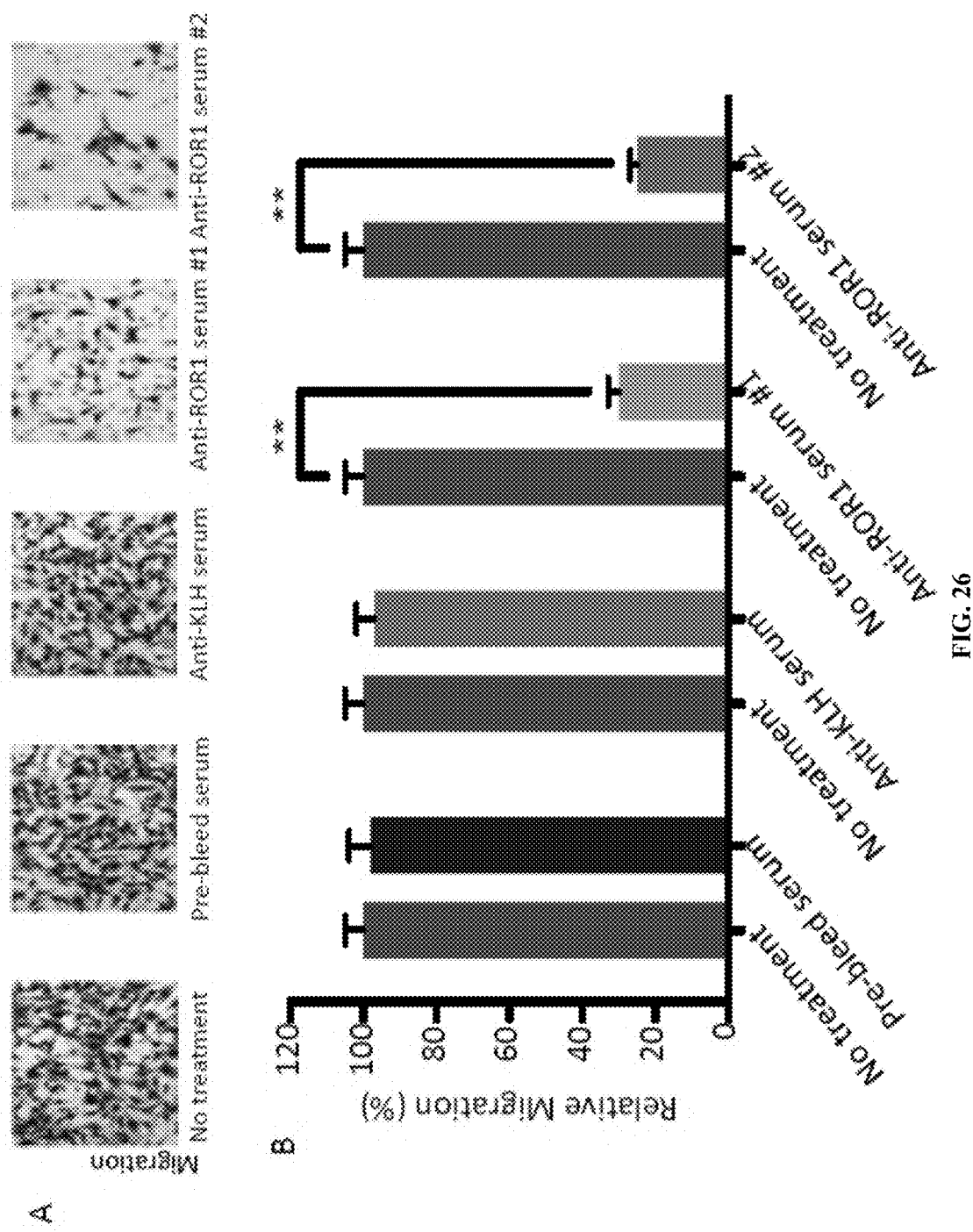

FIG. 26 shows anti-ROR1 sera from transgenic mice immunized with R22-KLH inhibits breast cancer migration in vitro. (A) Migrated cells were observed under 10× magnification after 1 h of anti-sera treatment and then 16 h of incubation at 37° C. Treatment legend (left to right): No treatment, Pre-bleed serum, Anti-KLH serum, Anti-ROR1serum #1, Anti-ROR1 serum #2. (B) Histogram of results of (A). Histogram legend (left to right): No treatment, Pre-bleed-serum; No treatment, Anti-KLH serum; No treatment, Anti-ROR1 serum #1; No treatment, Anti-ROR1 serum #2. Results are means±s.e.m. n=3. **p<0.01.

Figure 27:
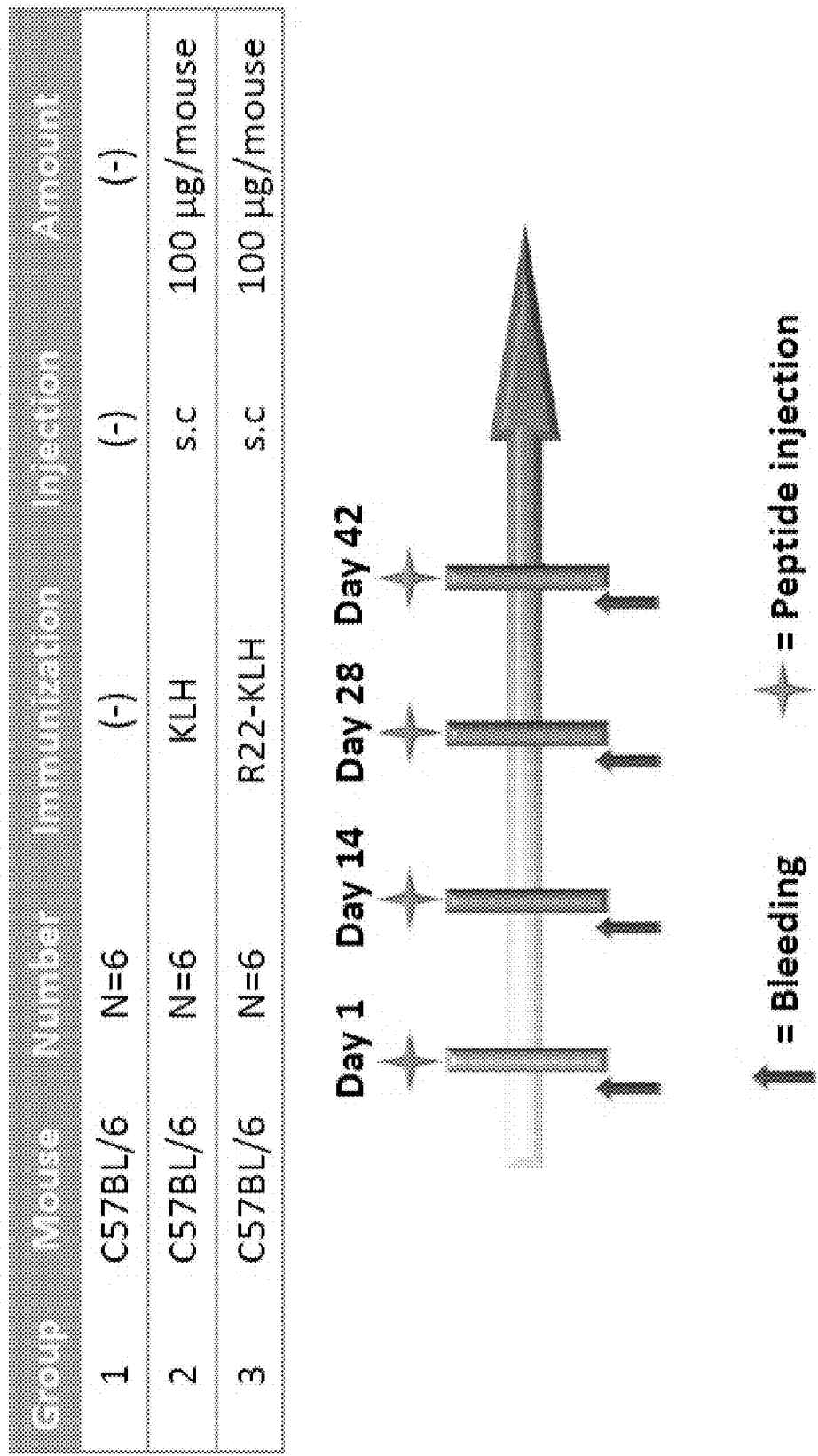

FIG. 27 shows the immunization scheme for R-22-KLH in C57BL/6 mice.

Figure 28:
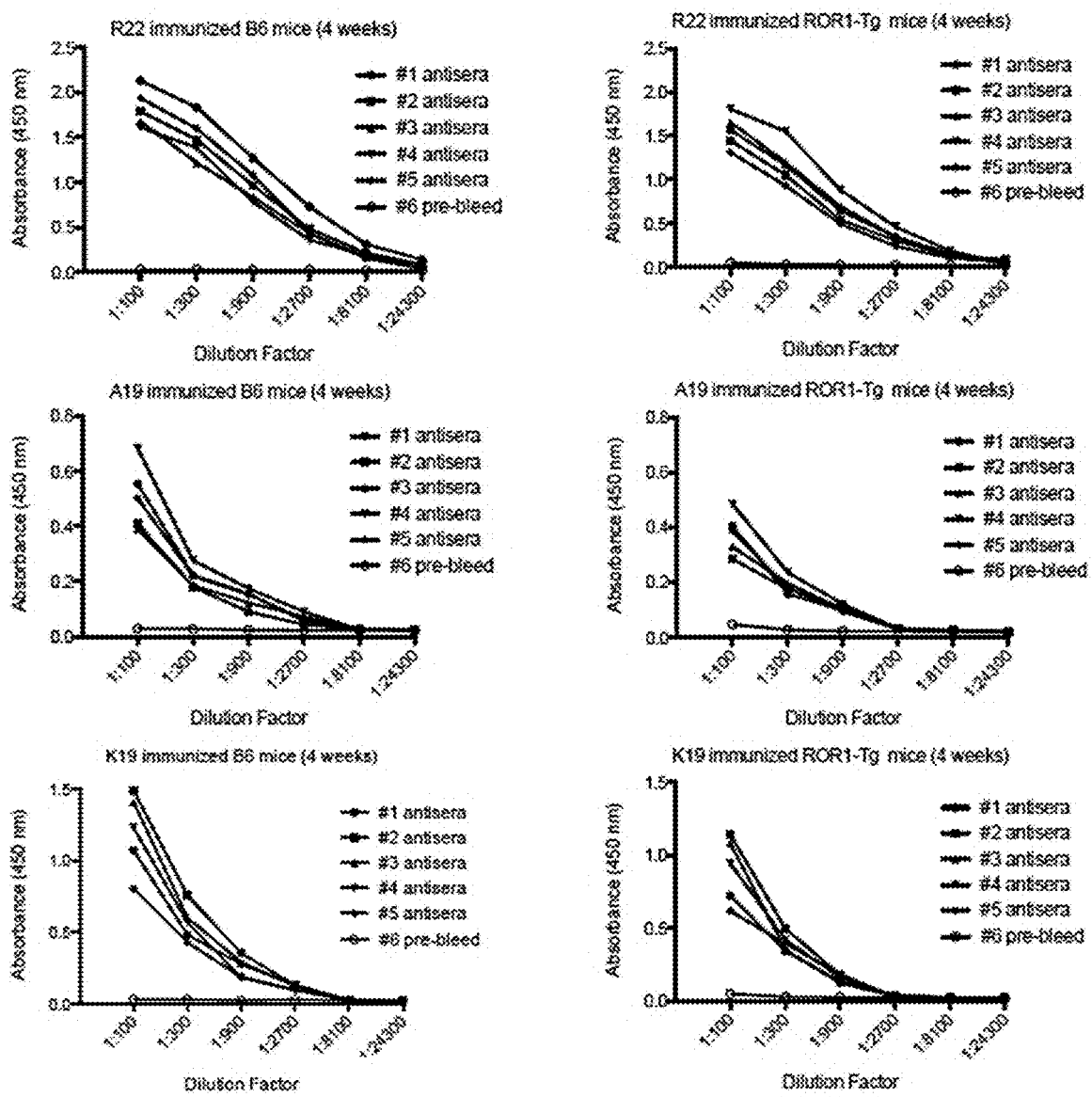

FIG. 28 shows the titration curves of antisera of mice immunized with KLH conjugates of any one of the three peptides described in FIG. 18. Depicted is the antisera binding to polystyrene plates coated with human ROR1 protein as assessed via ELISA.

Figure 29:
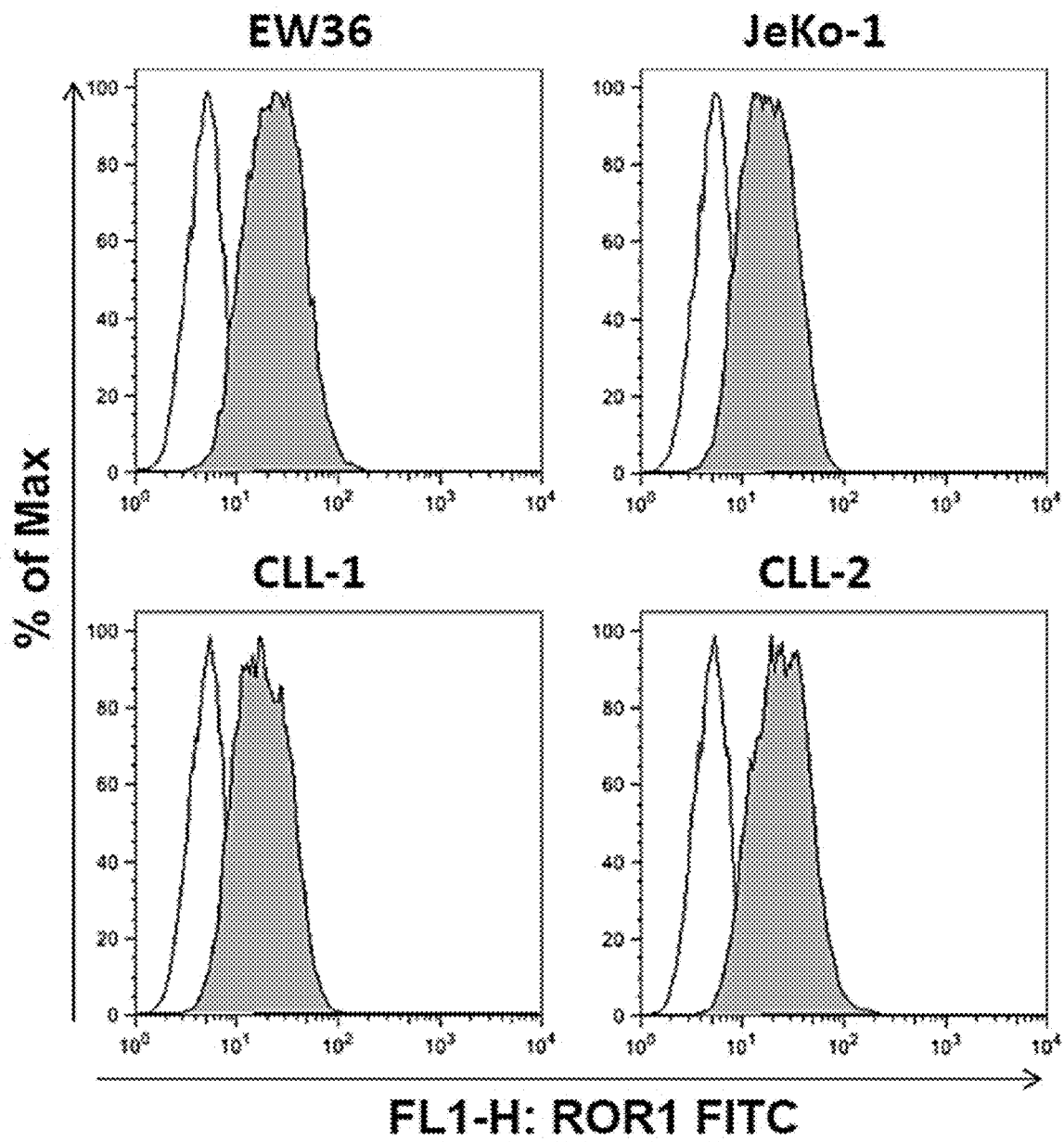

FIG. 29 shows FACS analysis of EW36, JeKo-1, or CLL cells. For this study, a dilution of antisera from mice immunized with R22-KLH was incubated with the cells for 20 minutes at 4 degrees C. The cells then were washed and then labeled with a goat anti-mouse Ig that was conjugated with a fluorochrome for detection by flow cytometry. The open histograms are the cells stained with the goat anti-mouse Ig without first incubating the cells with the R22-KLH antisera. The shaded histograms are the fluorescence of cells that first were incubated with the anti-R22-KLH antisera. The increase in fluorescence of the cells is due to the mouse anti-ROR1 antibodies bound to the surface, which then were detected with the goat anti-mouse Ig. The pre-immunization antisera of these mice or the antisera of mice immunized with KLH did not bind to these cells.

Figure 30:
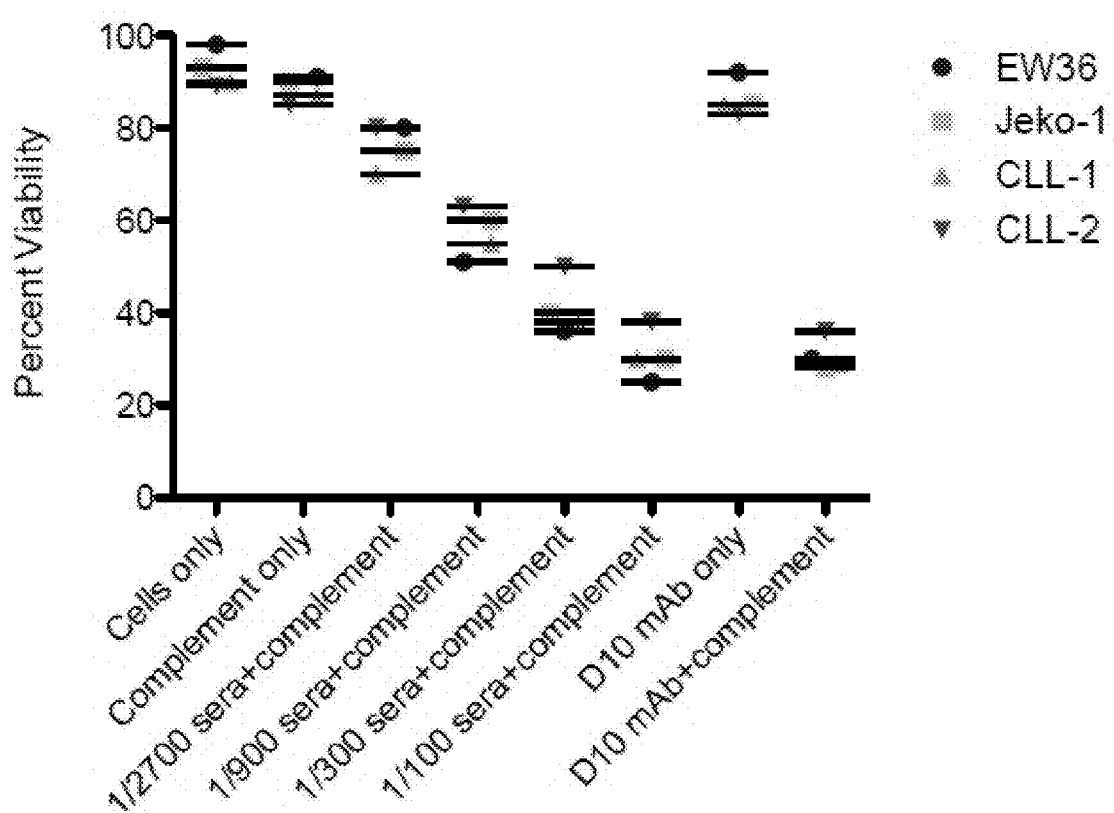

FIG. 30—The cells indicated in the legend were washed and plated at 25 µl with 5×10⁵ cells per well in RPMI/10% FBS in round-bottom 96-well plates (Corning Costar). The diluted antisera (25µl) and 25 µl of a 1:5 dilution of baby rabbit complement were added per well. D10 mAb was used as a positive control. All conditions were performed in triplicate. Plates were incubated for 4 h at 37° C., and cells were immediately quantitated for viability by DiOC6/PI staining and Flow Cytometric Analysis. This study indicates that either D10 or the antisera generated against the R22-KLH peptide could direct complement-mediated lysis of cells bearing human ROR1. Cells that did not bear ROR1 were not killed (not shown).

Figure 31:
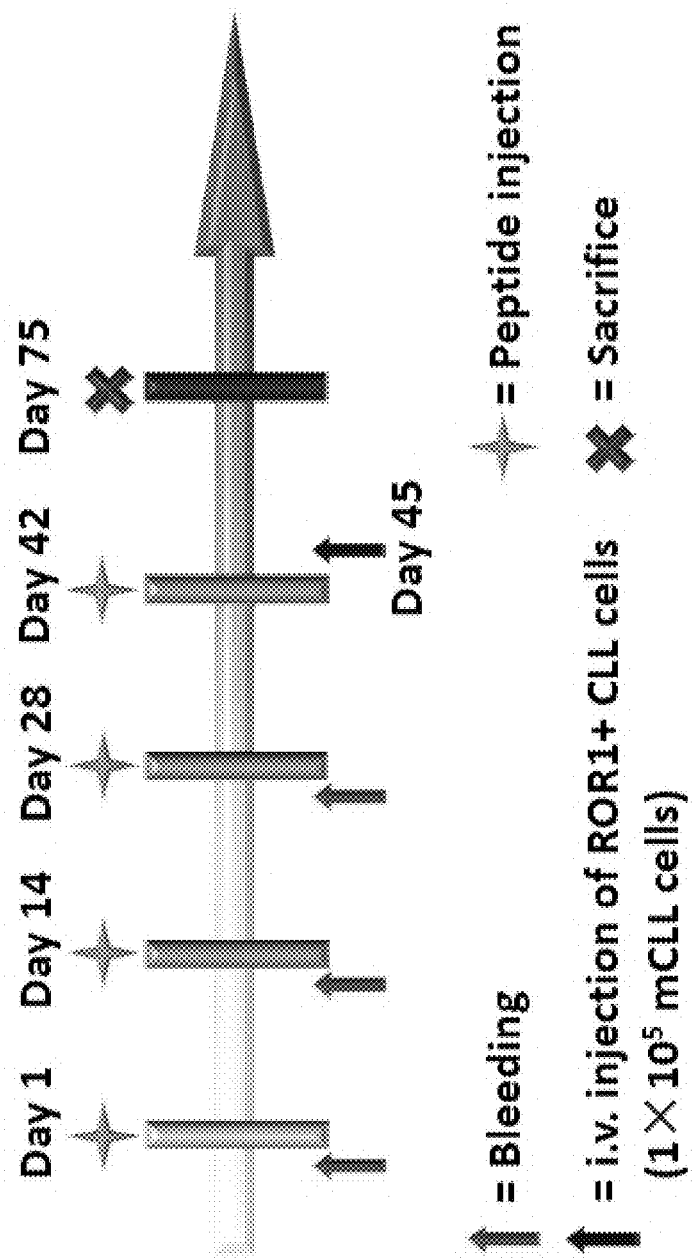

FIG. 31 shows the first R22-KLH immunization scheme for C57BL/6 mice. This peptide was conjugated with Keyhole limpet hemocyanin (KLH) and then used to immunize C57BL/6 mice according to the schema illustrated above. The first injection of KLH or R22-KLH was in complete Freund's adjuvant (CFA). The second and subsequent injections were in incomplete Freund's adjuvant (IFA). The animals were bled on the days marked with the purple arrow. 44 days after the day of the first injection, the C57BL/6 mice were challenged with human-ROR1-expressing CLL that originated in a human ROR1-transgenic C57BL/6 mouse that also was transgenic for the T-cell-leukemia 1 (TCL1 gene), also under the control of a B-cell specific promoter/enhancer (E-Cµ). This leukemia resembles human CLL and expresses human surface ROR1.

Figure 32:
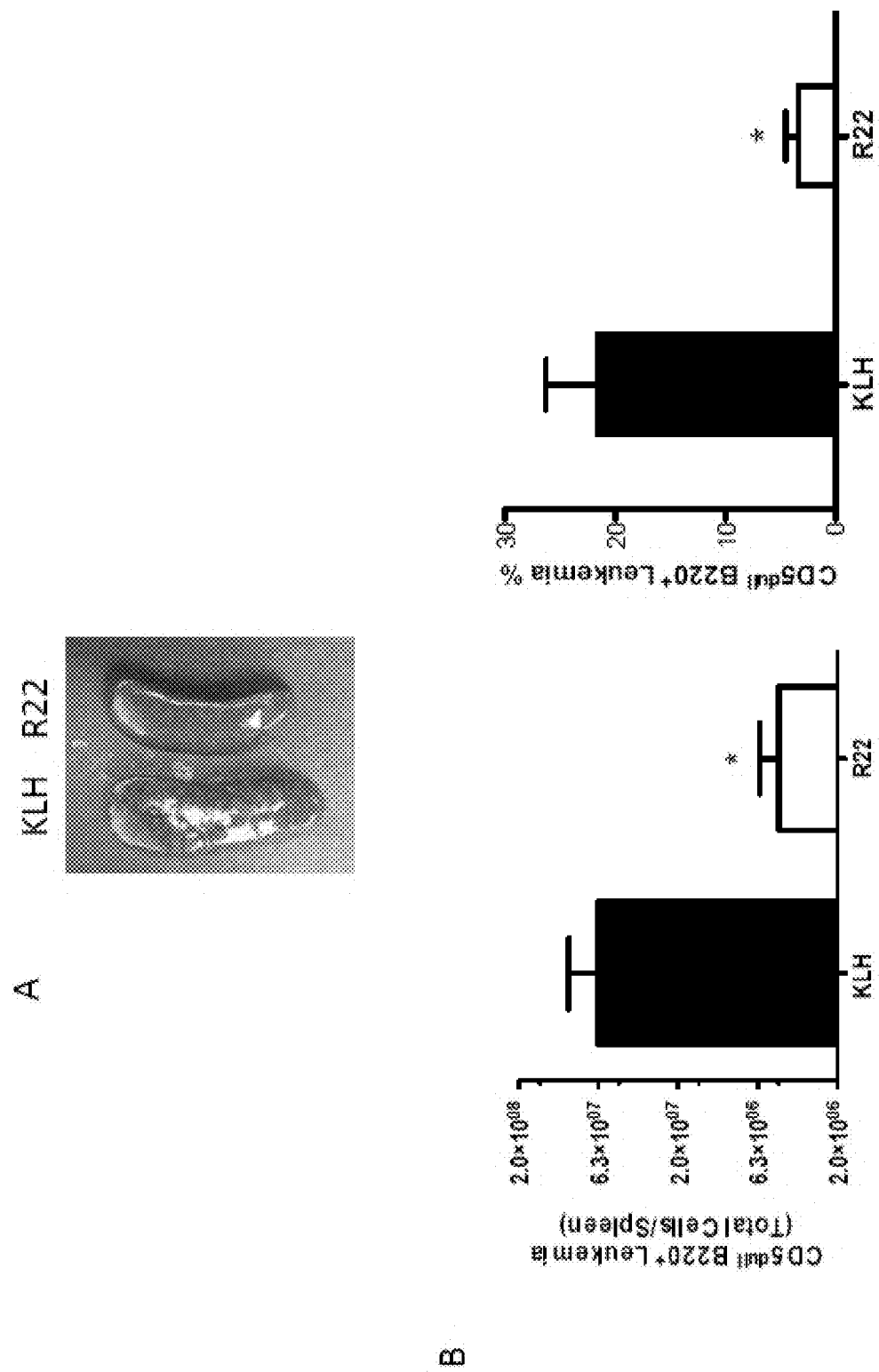

FIG. 32 shows the results of immunization with R22-KLH. A. A representative spleen from mice immunized with KLH versus a mouse immunized with R22-KLH. B. Inhibition of Engraftment of ROR1+ CLL by immunization with ROR1 peptide R22-KLH in C57BL/6 mice.

Figure 33:
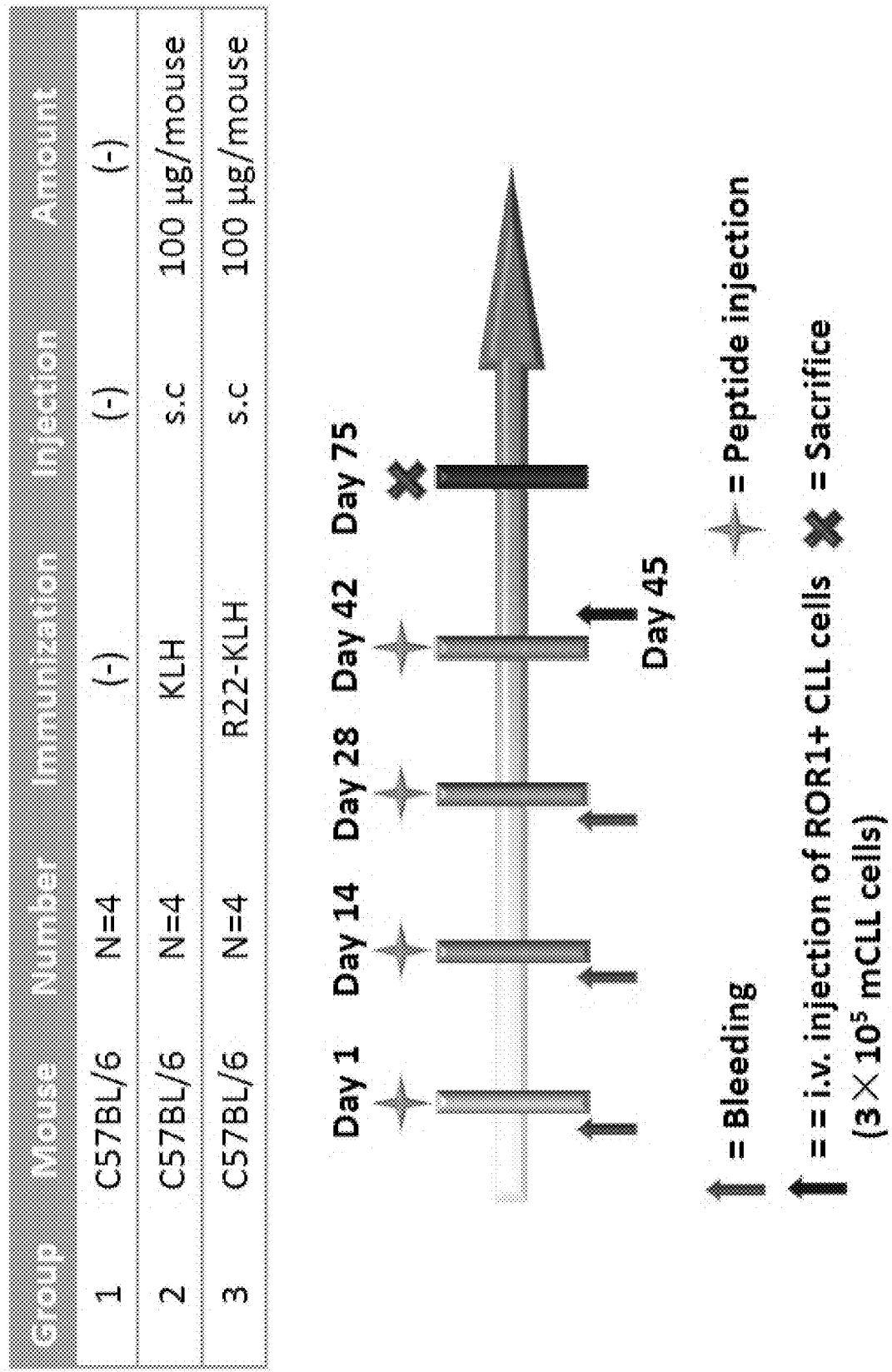

FIG. 33 shows the second immunization scheme for the R22-KLH in C57BL/6 mice.

Figure 34:
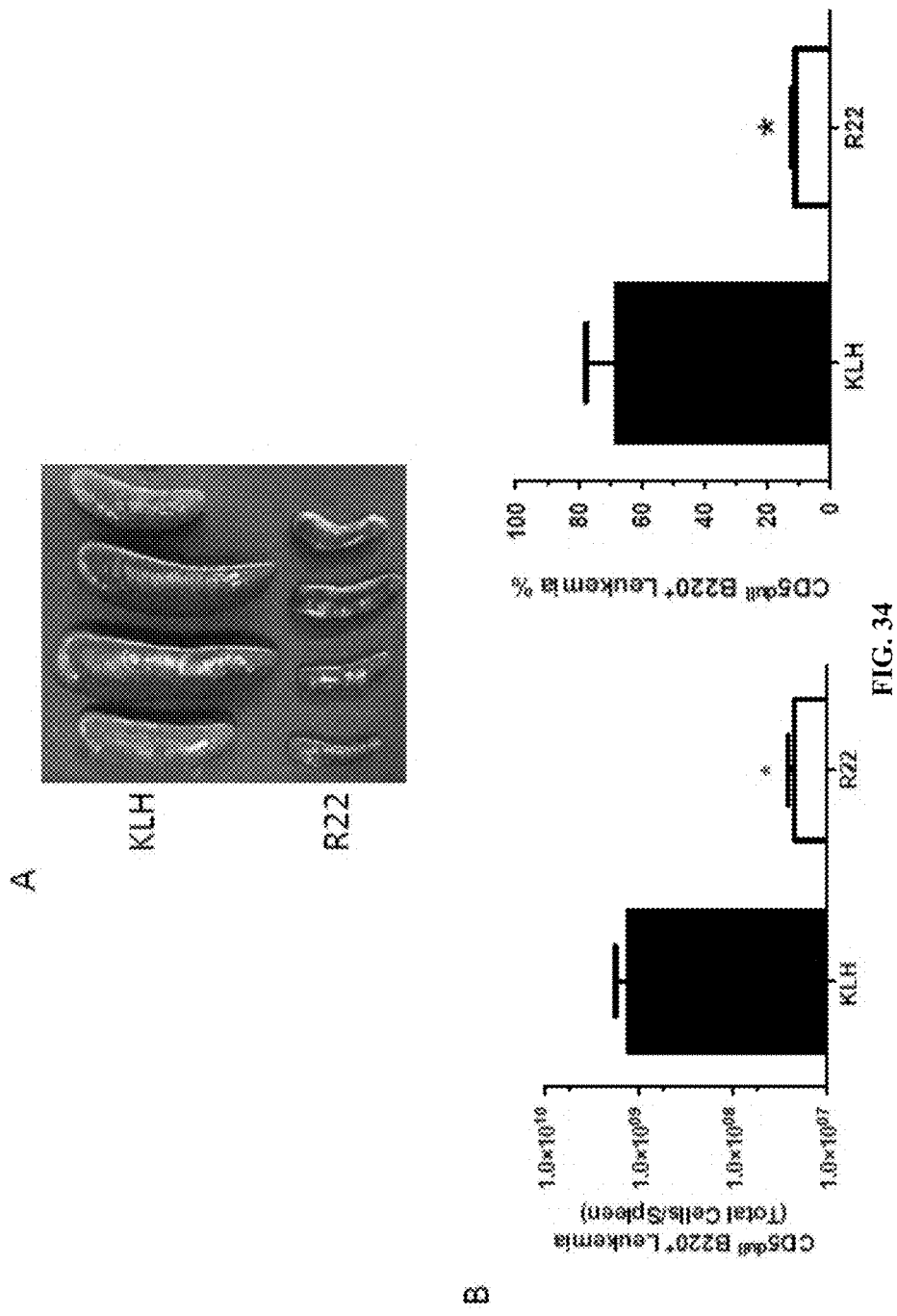

FIG. 34 shows the results of immunization with R22 peptide. A. Spleens from a mouse immunized with KLH and a mouse immunized with R22-KLH. B. Inhibition of Engraftment of ROR1+ CLL following immunization with R22-KLH in C57BL/6 mice.

Figure 35:
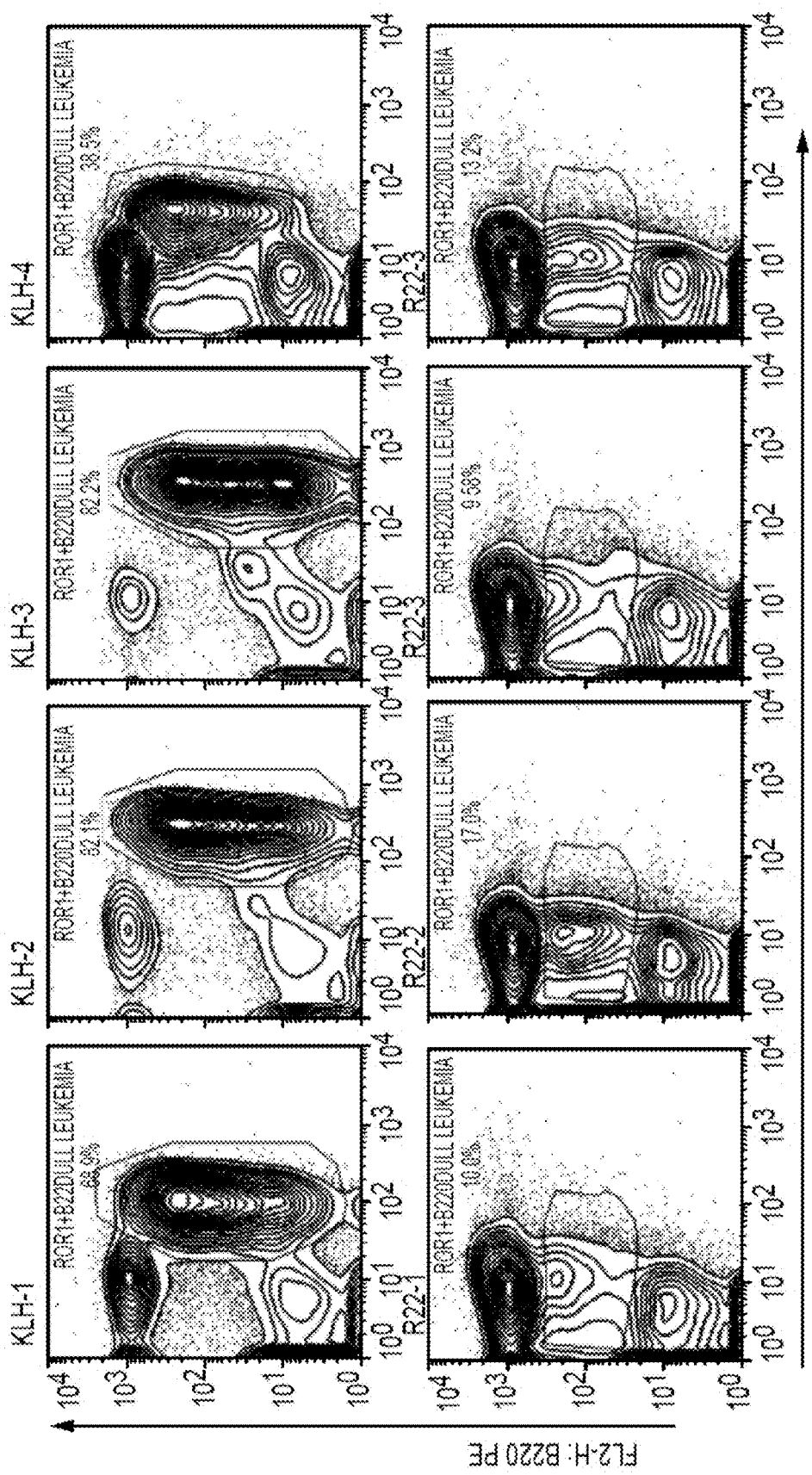

FIG. 35 is FACS analyses of splenocytes from C57BL/6 mice immunized with either KLH (top row) or R22-KLH (bottom row), using flurochrome-conjugated mAb specific for B220 (y-axis) or ROR1 (x-axis). The mAb used to stain the cells binds to a non-crossblocking epitope of ROR1 than the antibodies induced by R22-KLH. The box delineates the area in which the leukemia cells are detected. Note that there are much fewer, if any, leukemia cells in the spleens of mice immunized with the R22-KLH vaccine.

Figure 36:
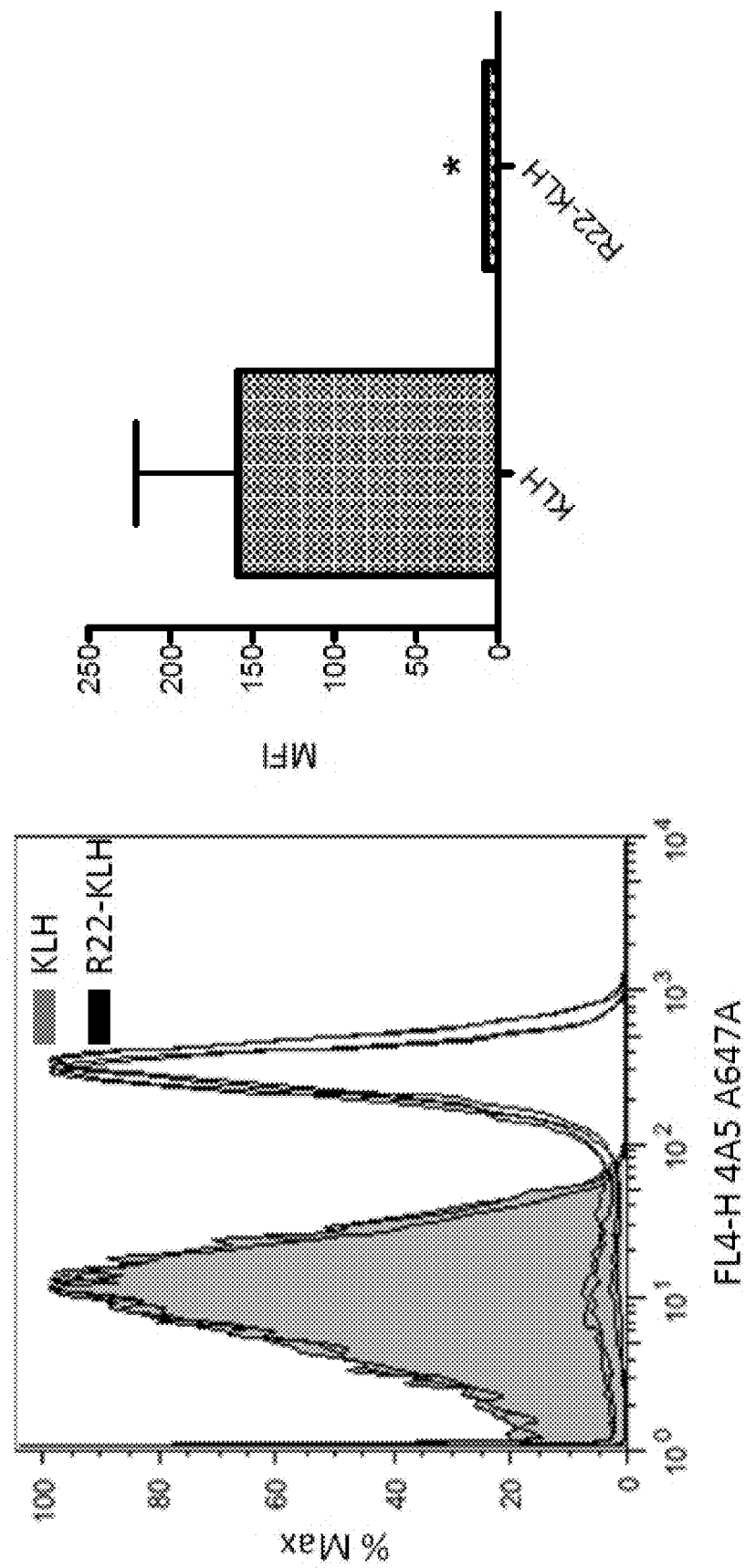

FIG. 36 is FACS analysis of ROR1 on the ROR1+ CLL cells, which indicates that ROR1 was down-modulated after immunization with R22-KLH in C57BL/6 mice.

Figure 37A:
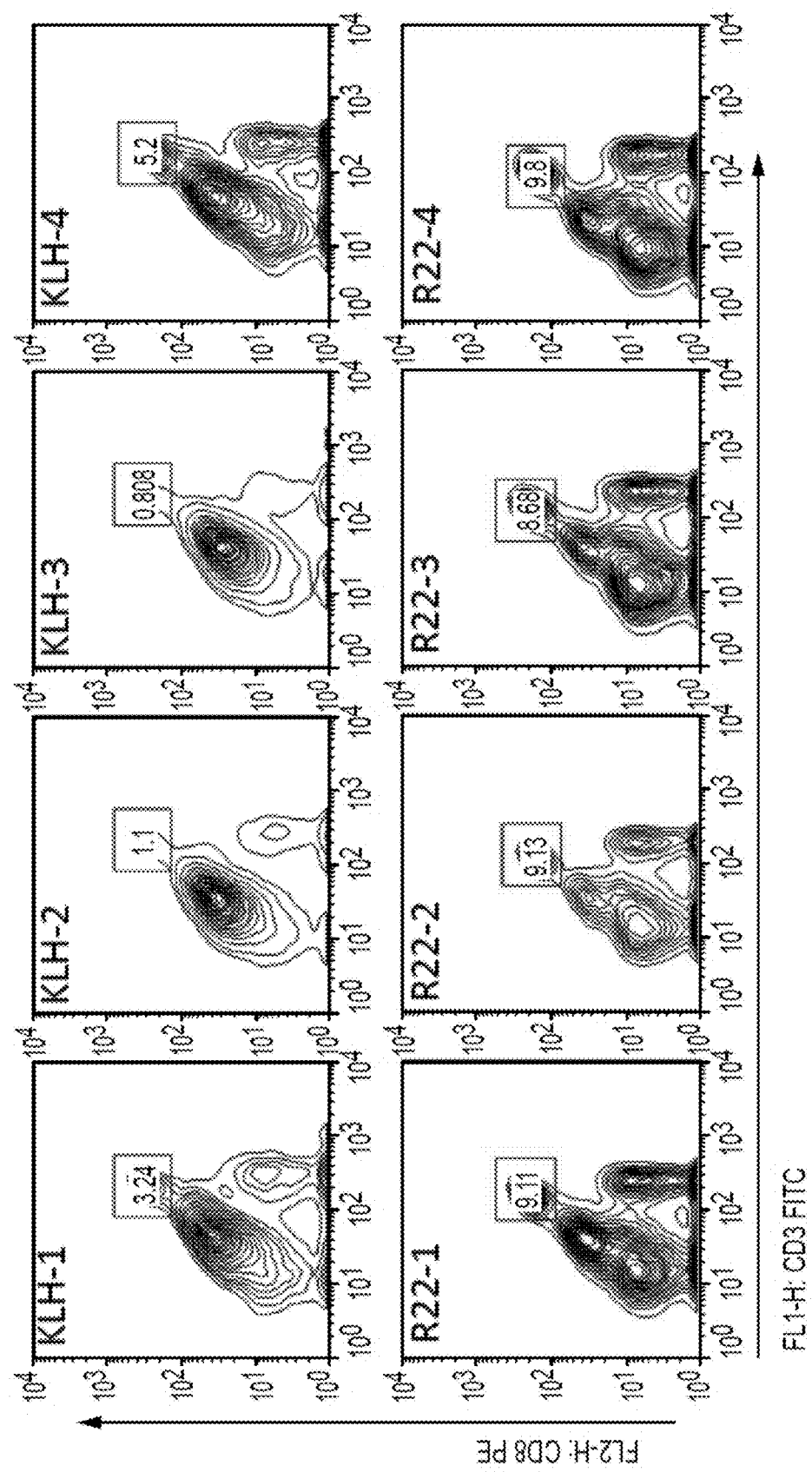
Figure 37B:
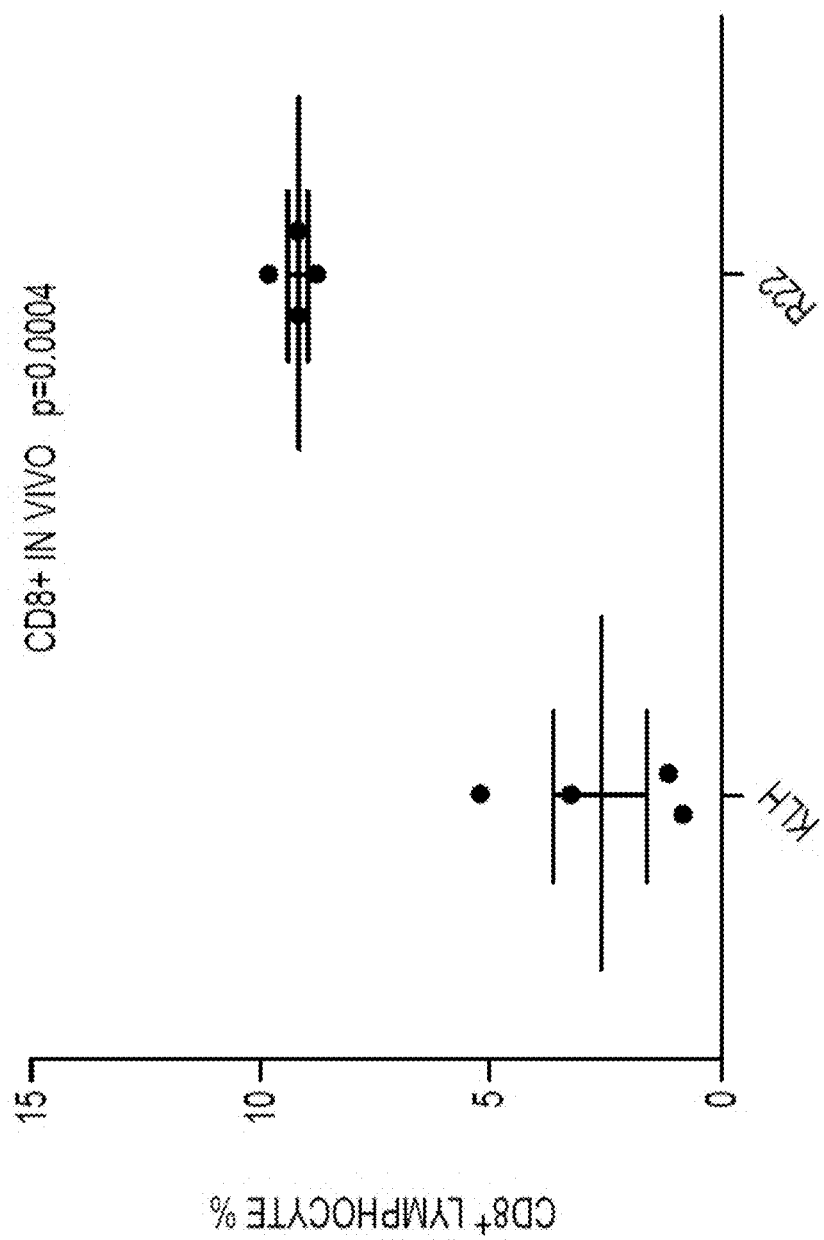

FIGS. 37A and 37B show FACS analysis of CD8+ T cells present in mice that were immunized with KLH or R22-KLH. (A) Immunization with R22 causes an increase in the number of CD8+ T cells, which was absent in mice immunized with KLH. The bottom panel shows the percentage of CD8+ T cells from the spleens of mice first immunized 75 days earlier with either KLH, or R22-KLH. (B) Histogram depicting CD8⁺ lymphocyte % for KLH (left bin) and R22-KLH (right bin).

Figure 38:
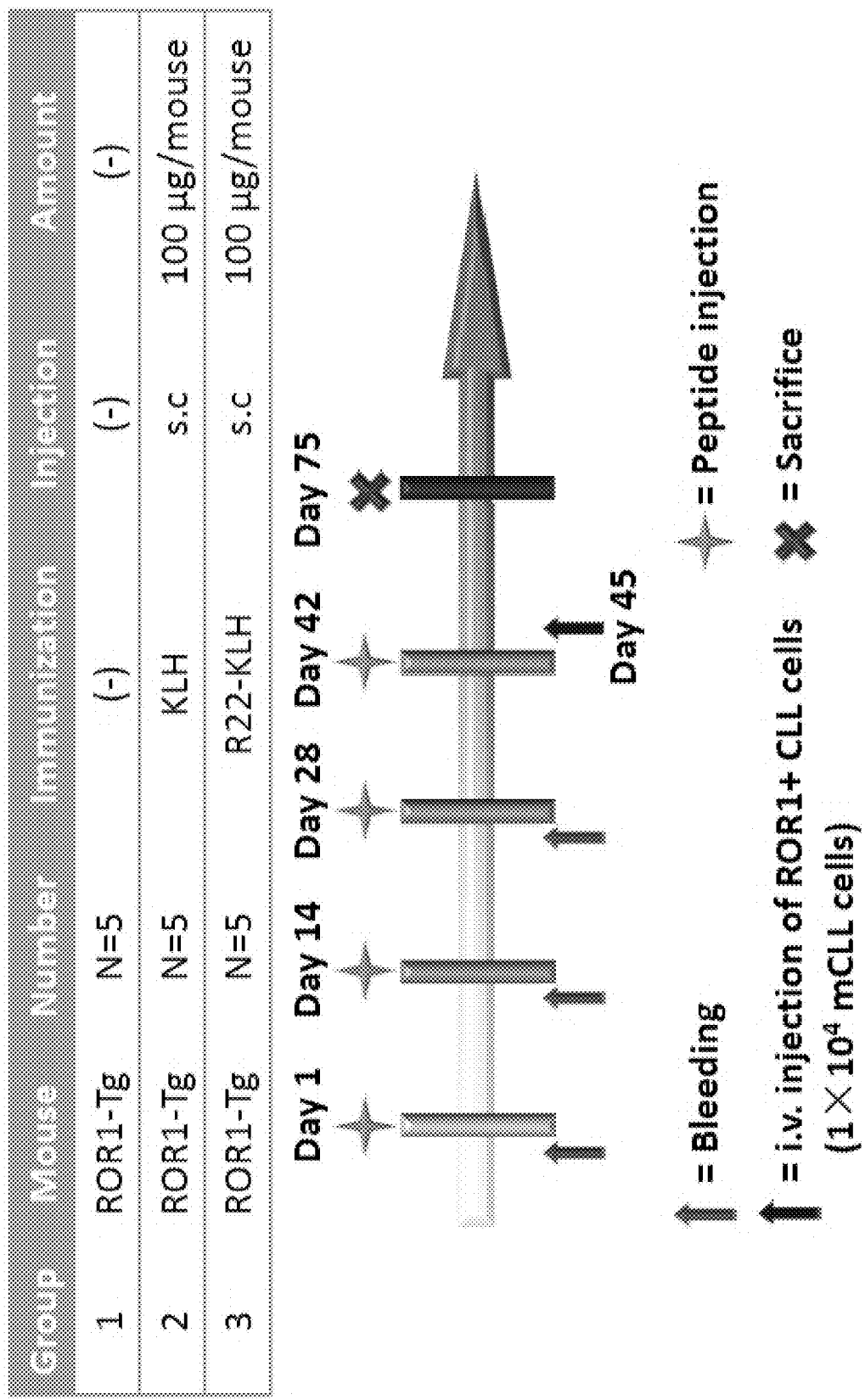

FIG. 38 shows the immunization scheme for R22-KLH immunization of ROR1 transgenic mice.

Figure 39A:
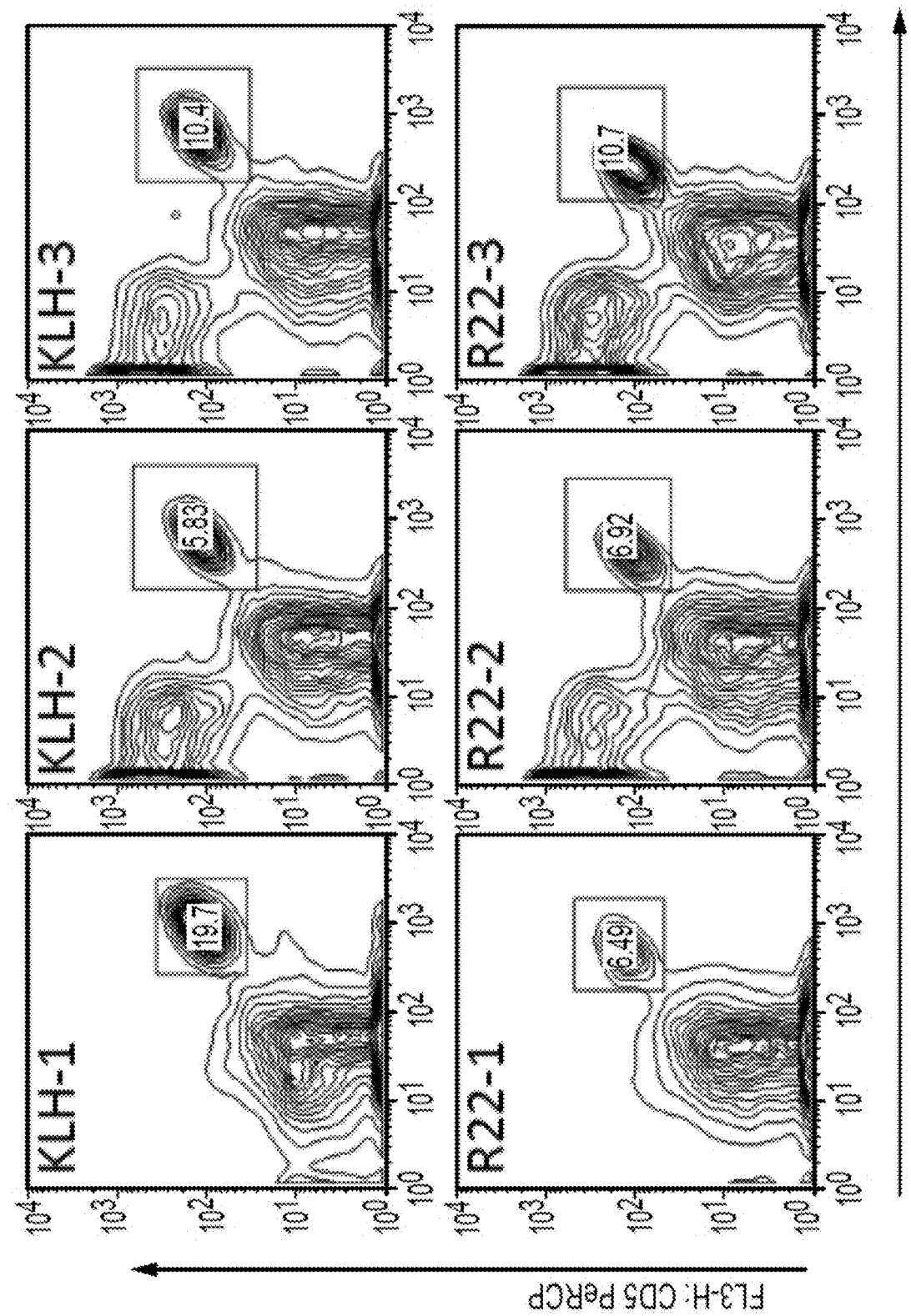
Figure 39B:
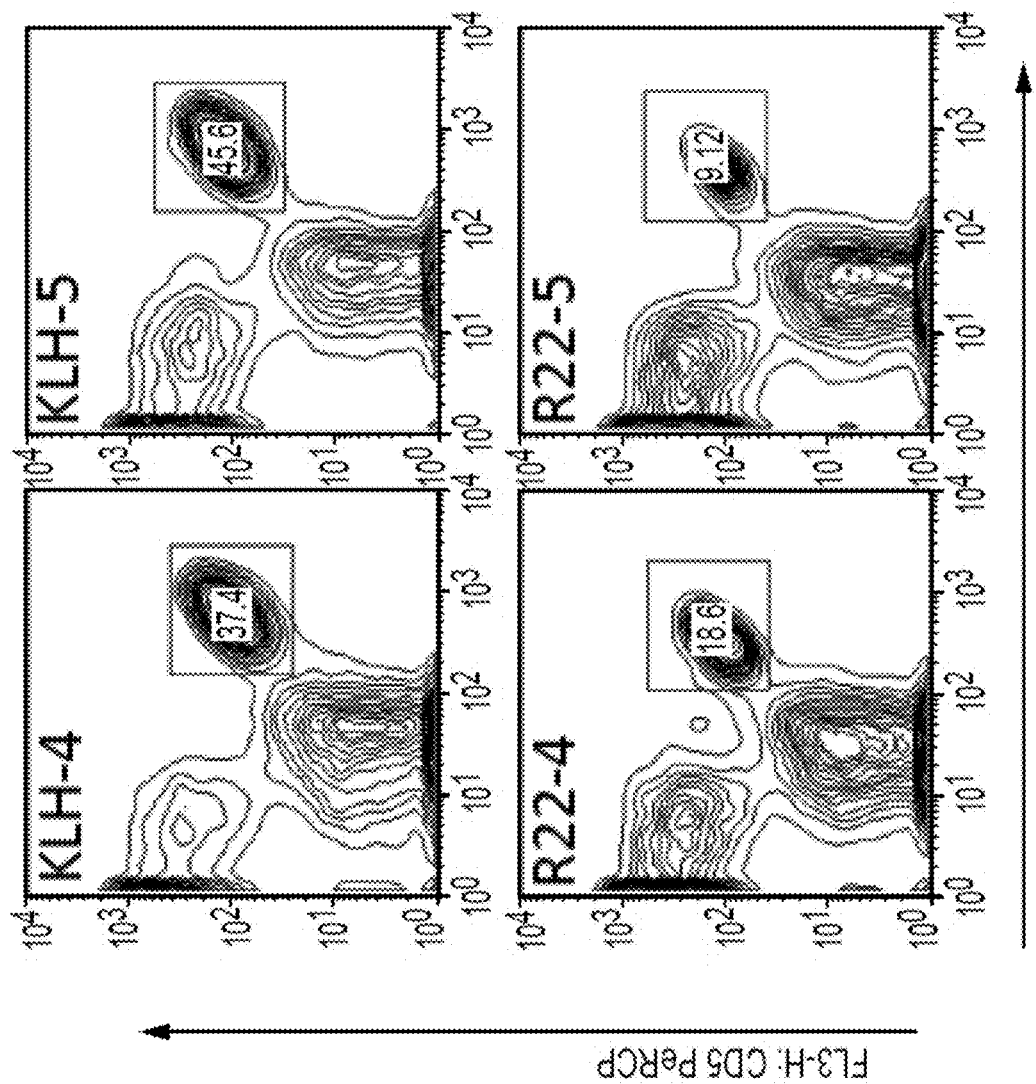

FIGS. 39A and 39B show FACS analysis of the inhibition of ROR+ CLL engraftment by immunization with ROR1 peptide R22 in ROR1-Tg mice.

Figure 40:
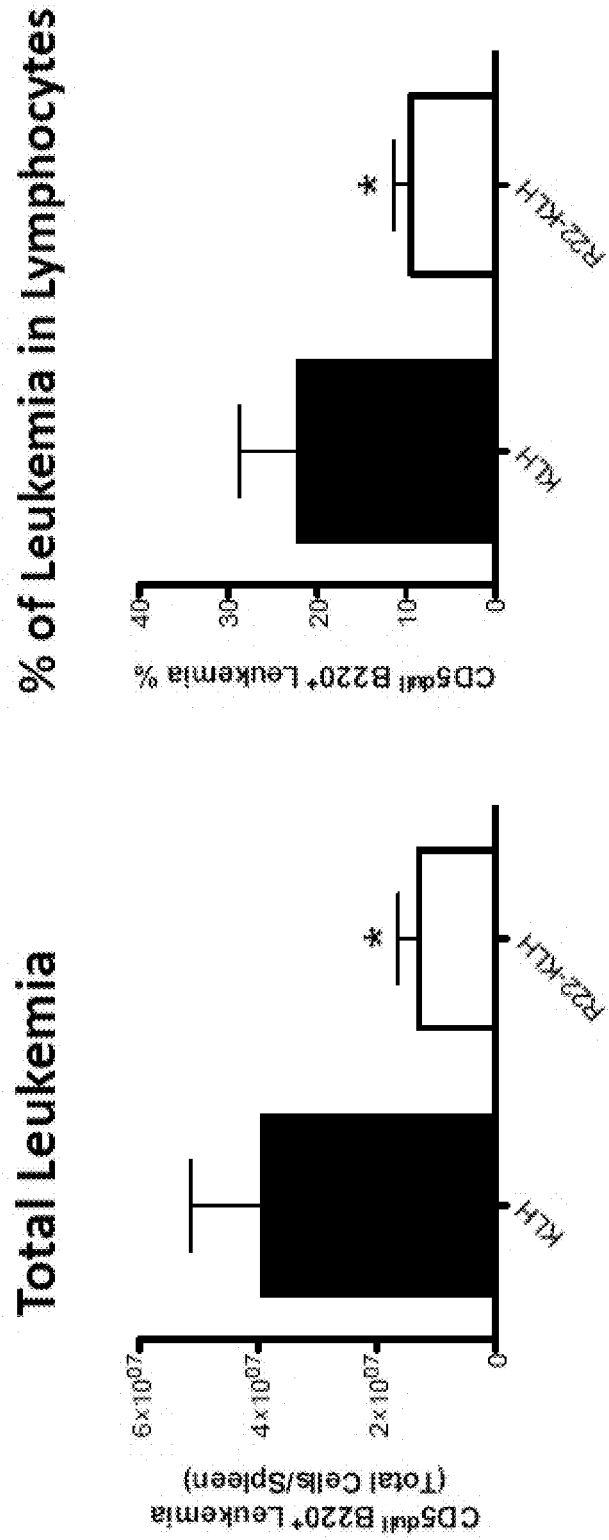

FIG. 40 shows the results of immunization with R22-KLH in ROR1 transgenic mice. ROR1+ CLL was inhibited following immunization with R22-KLH in ROR1 transgenic mice.

Figure 41:
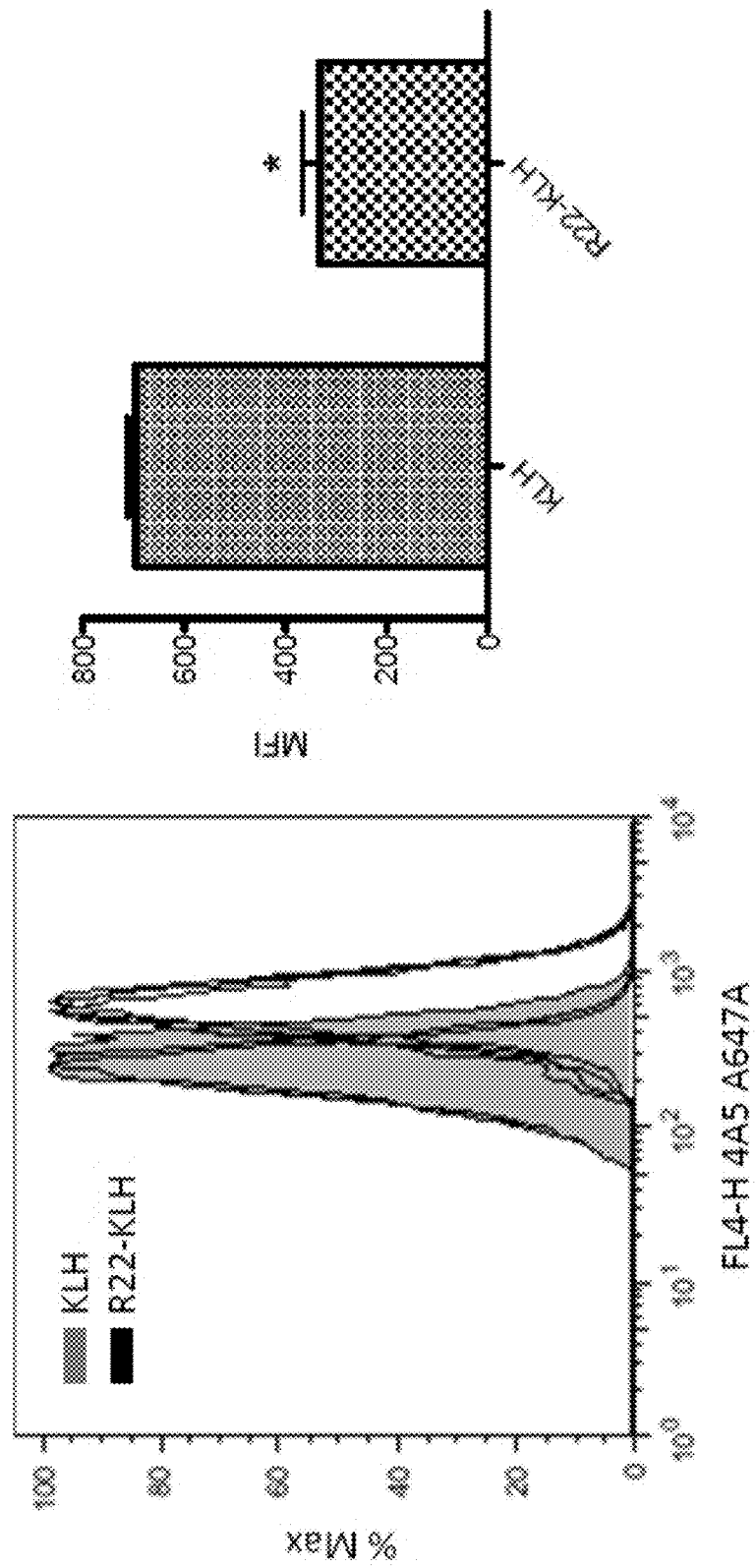

FIG. 41 is FACS analysis of ROR1 on the ROR1+ CLL cells, which indicates that ROR1 was down-modulated after immunization with R22-KLH in ROR1 transgenic mice.

Figure 42A:
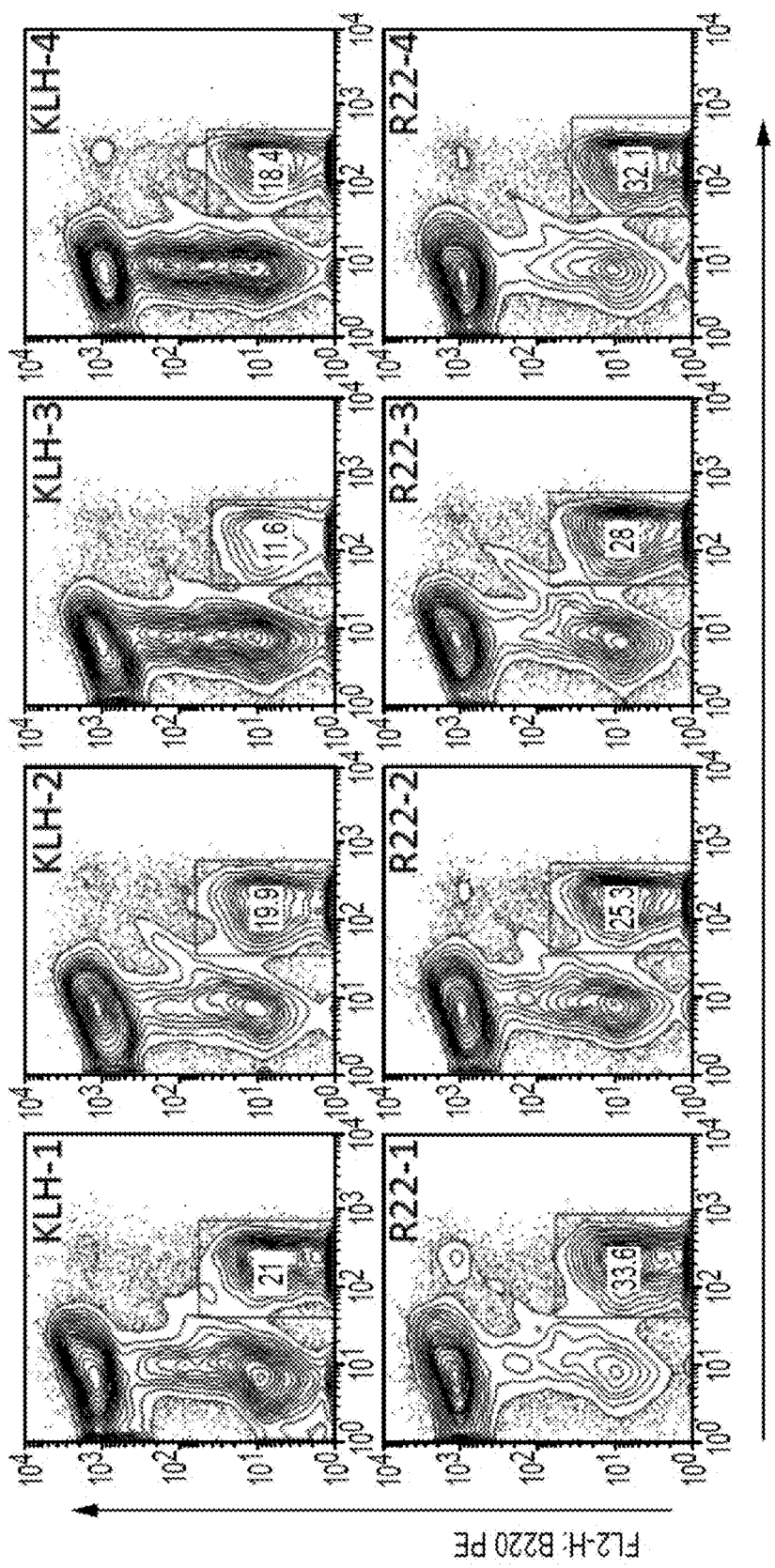
Figure 42B:
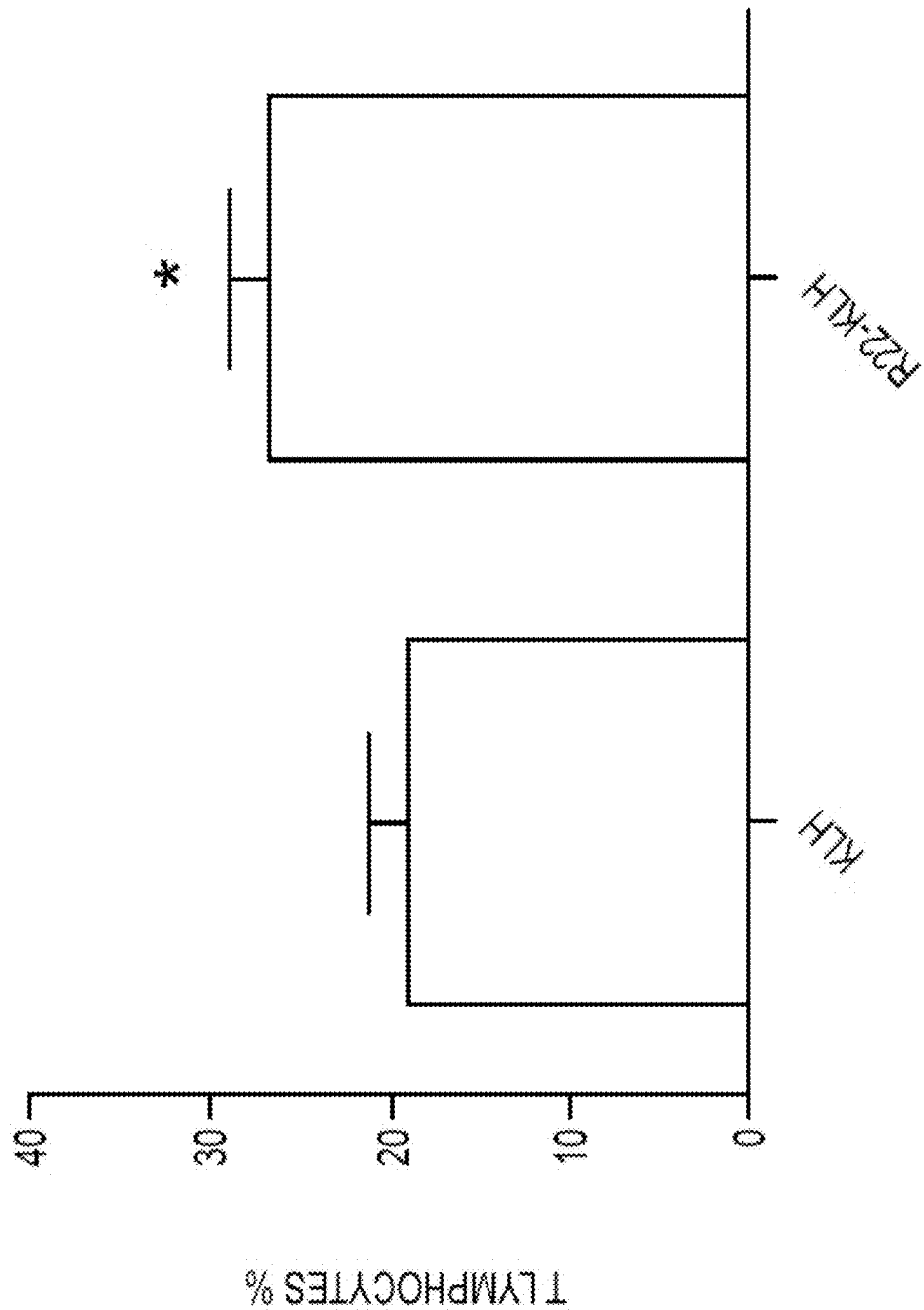

FIGS. 42A and 42B show FACS analysis of CD3+T lymphocytes present in ROR1-Tg mice that were immunized with KLH or R22-KLH. (A) Figure shows that immunization with R22-KLH caused an proliferation of T lymphocytes. (B) Figure shows the percentage of CD3+T lymphocytes harvested from the spleens of mice on day 75.

Figure 43A:
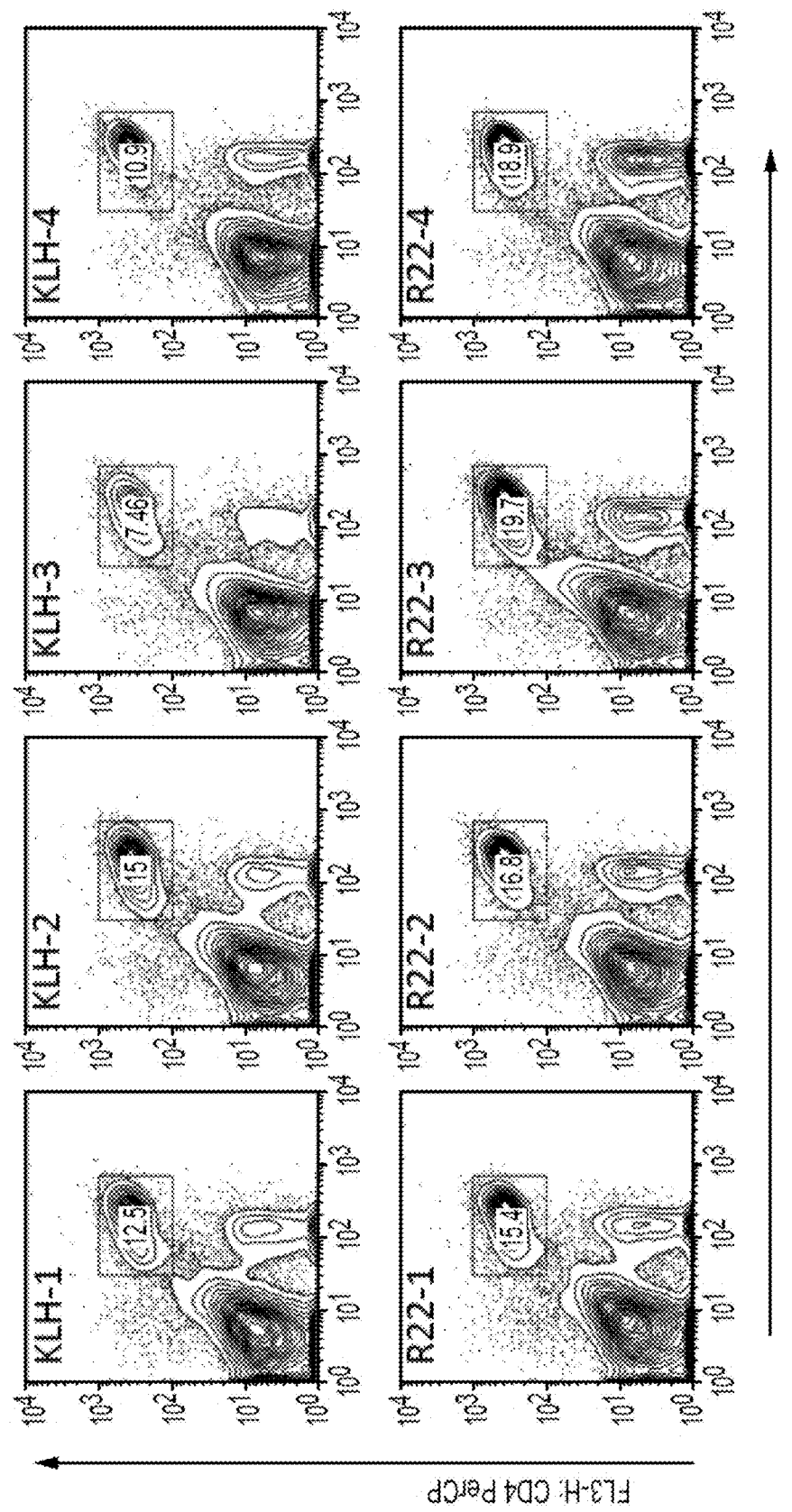
Figure 43B:
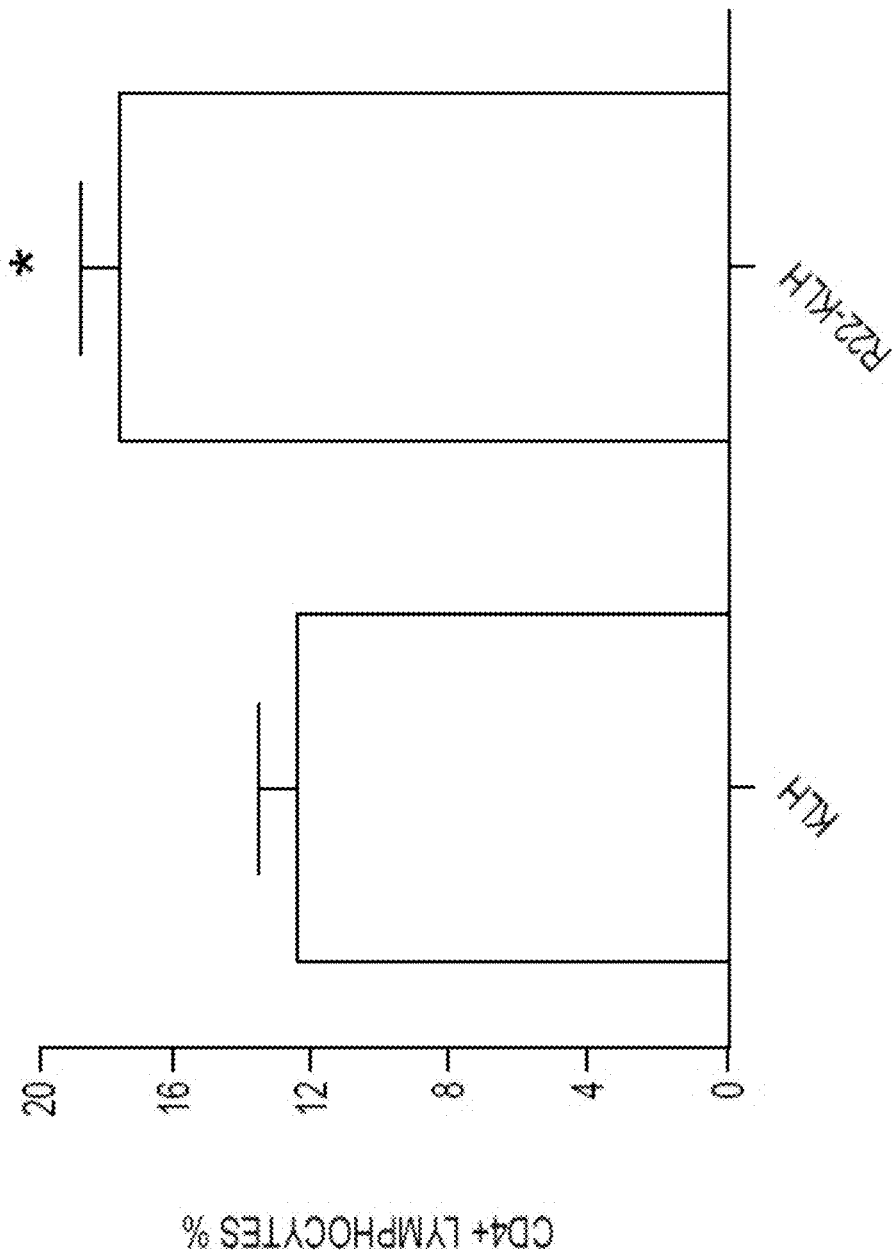

FIGS. 43A and 43B show FACS analysis of CD4+ T cell present in mice that were immunized with KLH or R22-KLH. Panel A shows that immunization with R22-KLH causes an increase in the number of CD4+ T cells, which not detected in mice immunized with KLH. Panel B. Shows the percentage of CD4+ T cells harvested from the spleens of mice on day 75.

Figure 44A:
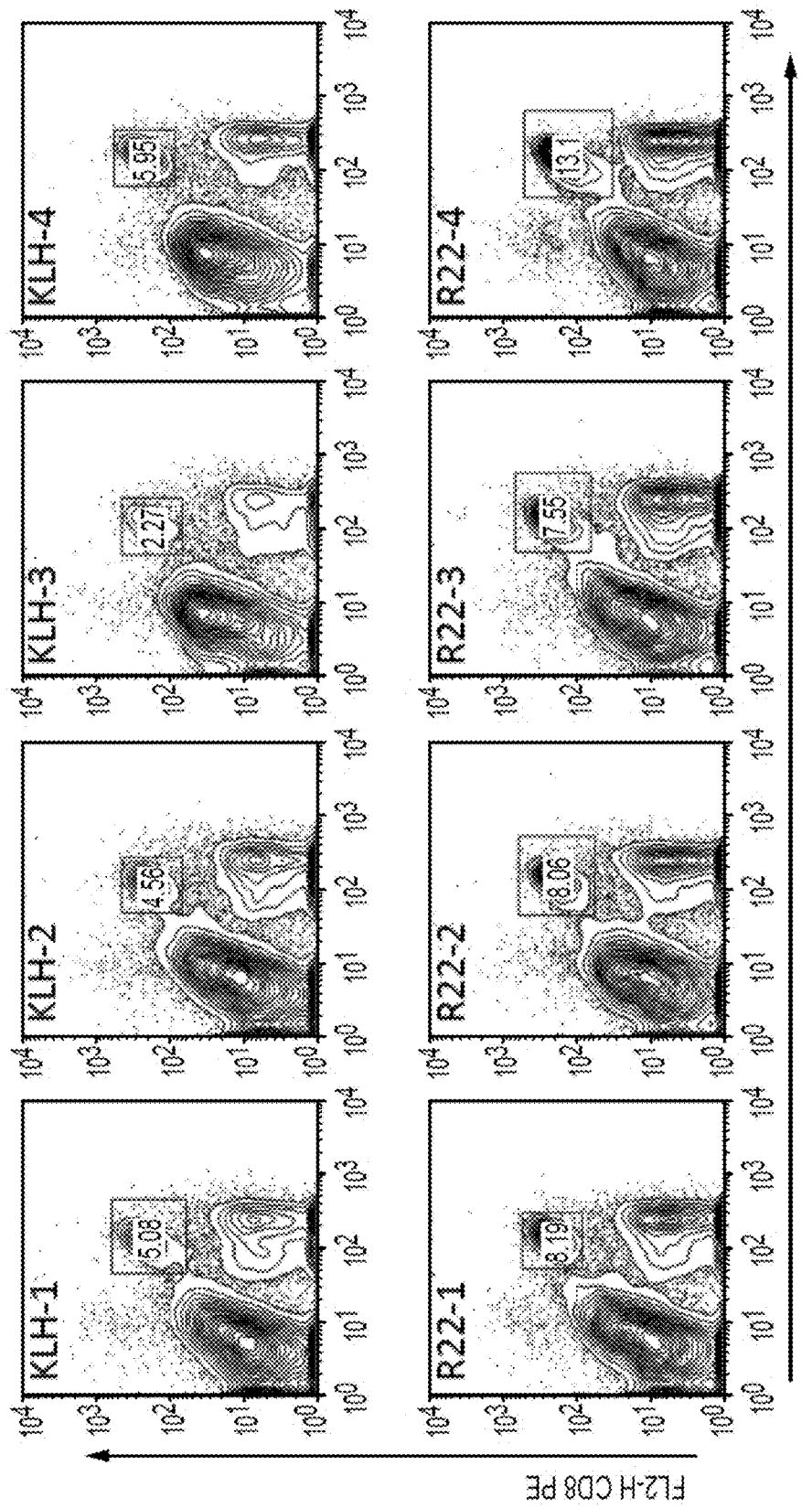
Figure 44B:
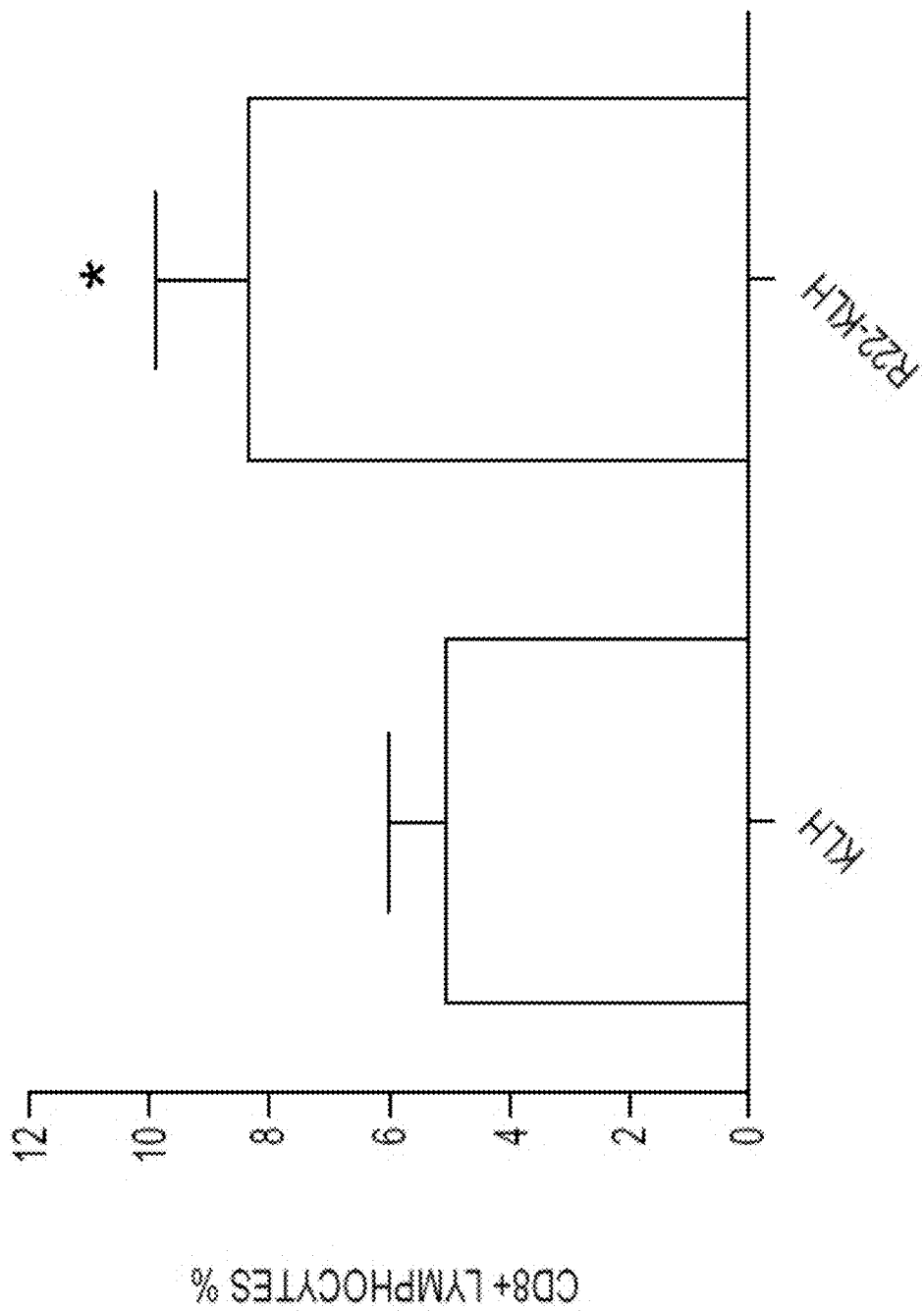

FIGS. 44A and 44B show FACS analysis of CD8+ T cell present in mice that were immunized with KLH or R22-KLH. Panel A shows that immunization with R22-KLH causes an increase in the number of CD8+ T cells, which not detected in mice immunized with KLH. Panel B. Shows the percentage of CD8+ T cells harvested from the spleens of mice on day 75.

Figure 45:
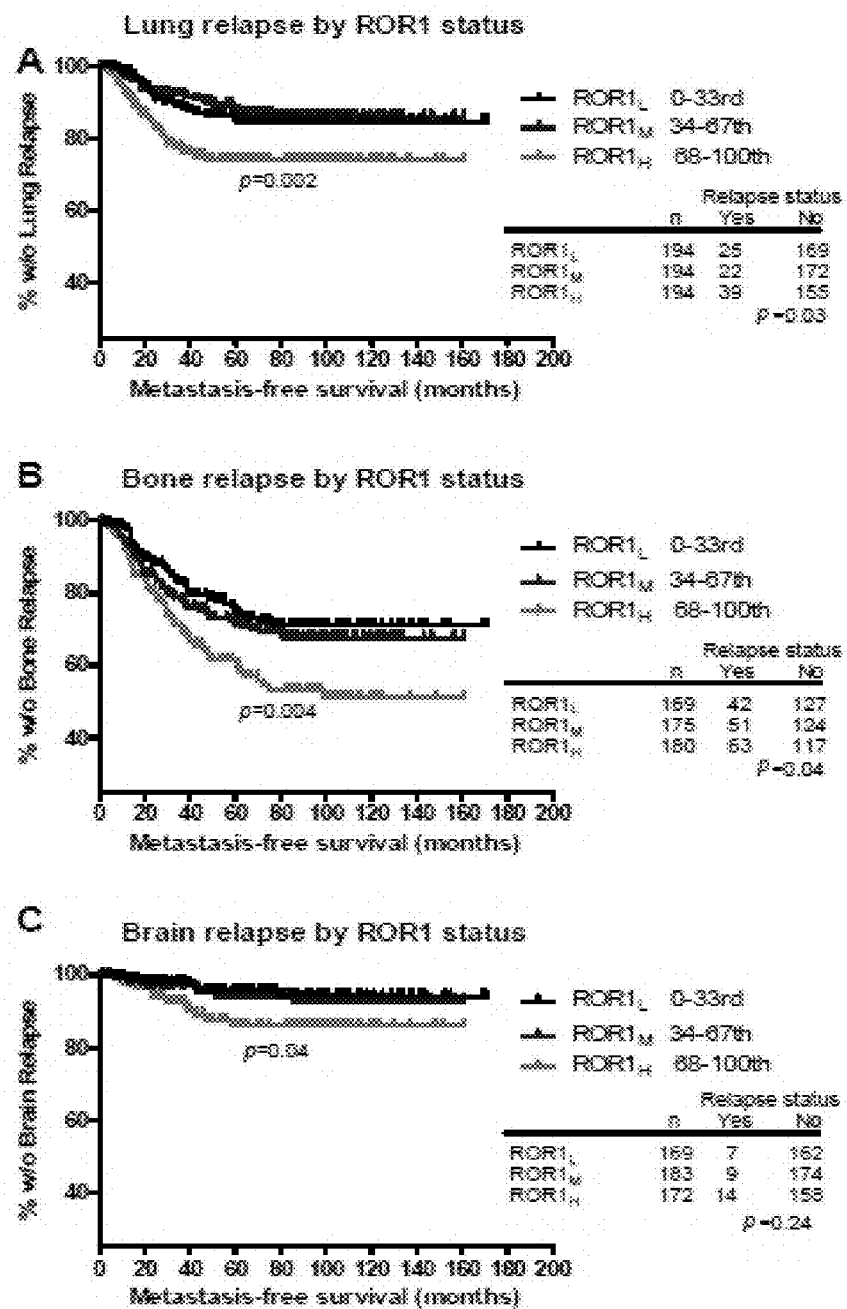

FIG. 45 shows high-level expression of ROR1 in breast cancer is associated with shorter lung, bone and brain metastasis-free survival. The graph was derived from published data available through the PubMed GEO database (GSE2603, GSE5327, GSE2034, and GSE12276). Kaplan-Meier curves depict the prognostic impact of ROR1 expression on (A) lung metastasis-free survival, (B) bone metastasis-free survival, or (C) brain metastasis-free survival. For each analysis, 582 cases were segregated into tertiles with group designated ROR1H representing the one-third of the patients who had tumors with the highest levels of ROR1 mRNA, and the group designated ROR1L representing the one-third of patients who had cancers with the lowest levels of ROR1 mRNA. The one-third of patients who had tumors with intermediate expression of ROR1 mRNA was designated as ROR1M. Metastasis-free survival was determined by Kaplan-Meier analyses, and statistical differences were determined by log-rank test. The number of patients in each category, the total metastatic events, and the corresponding P values (chi-square test) are shown in the embedded tables.

Figure 46:
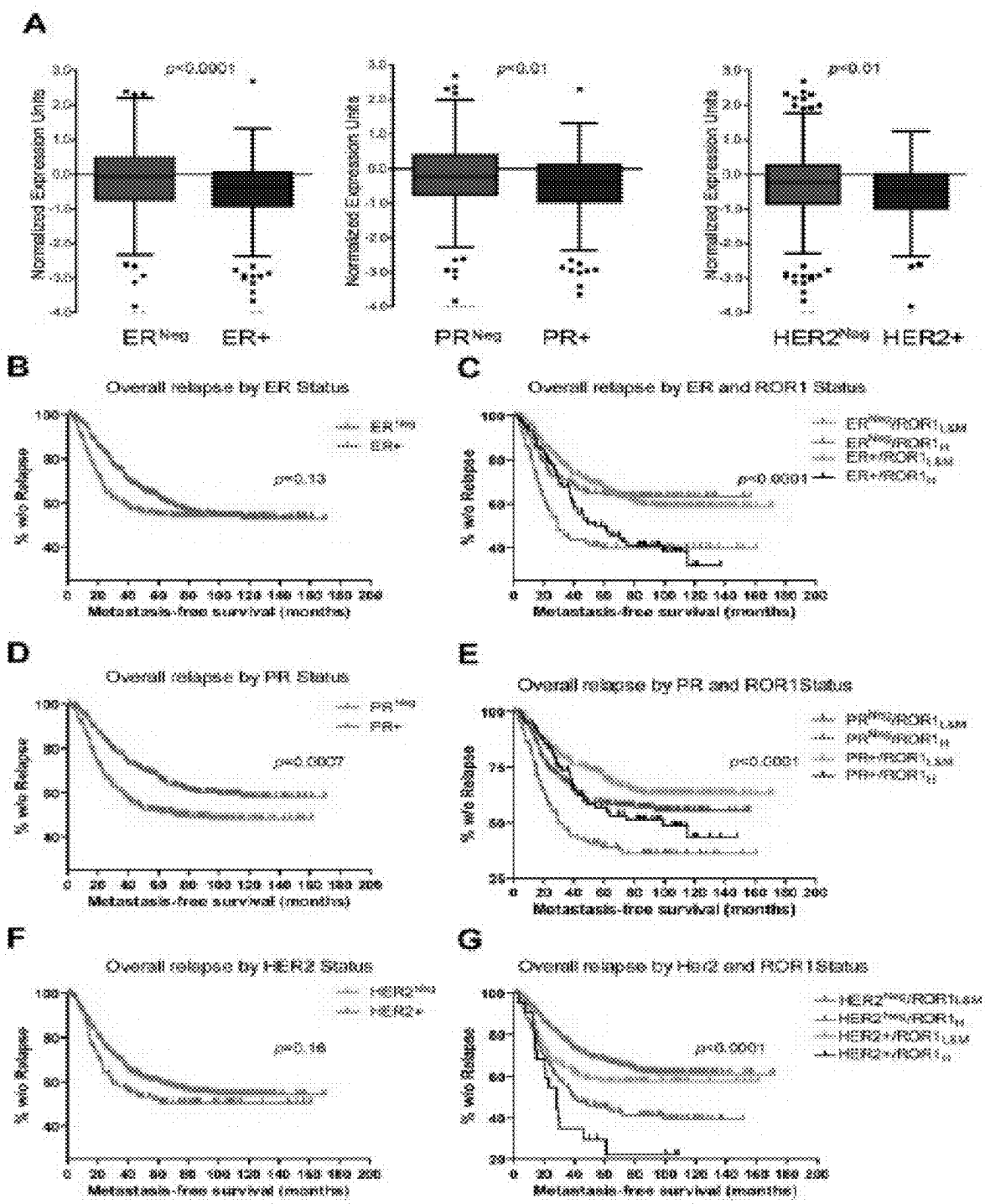

FIG. 46 shows high-level expression of ROR1 in breast cancer is associated with shorter metastasis-free survival, and independent from their ER, PR and HER2 status. Cohort of 582 patients with breast adenocarcinoma were included in the survival analysis. (A) Comparison of the levels of ROR1 mRNA expression of the malignant cells of ERNeg (n=242) and ER+(n=325) breast cancer patients (left panel), PRNeg (n=274) and PR+(n=271) breast cancer patients (center panel), and HER2Neg (n=404) and HER2+(n=106) breast cancer patients (right panel). Results are means±SEM The p value was determined by Student's t-test. (B) Prognostic impact of ER status on overall-metastasis-free survival (P=0.13 by log-rank test). (C) Prognostic impact of ER status and ROR1 mRNA expression on overall-metastasis-free survival (P<0.0001 by log-rank test). (D) PR status on overall-metastasis-free survival (P=0.0007 by log-rank test). (E) Prognostic impact of PR status and ROR1 mRNA expression on overall metastasis-free survival (P<0.0001 by log-rank test). (F) HER2 status on overall-metastasis-free survival (P=0.16 by log-rank test). (G) Prognostic impact of HER2 status and ROR1 mRNA expression on overall metastasis-free survival (P<0.0001 by log-rank test).

Figure 47:
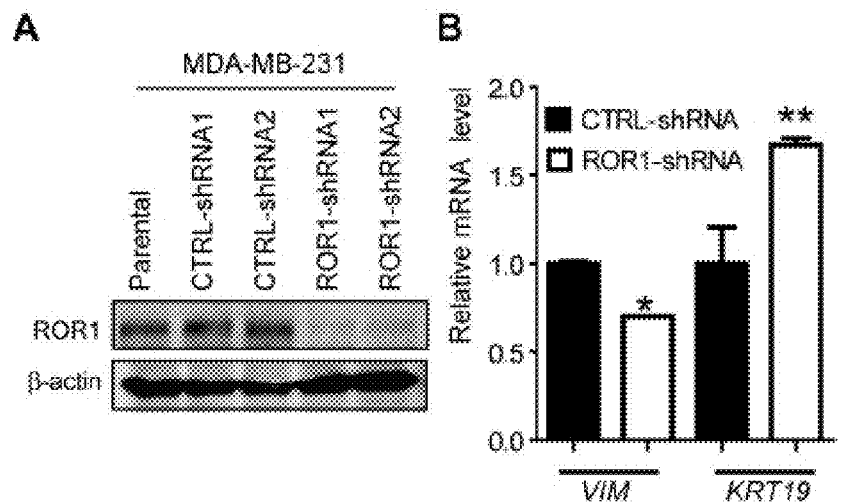

FIG. 47 shows expression of ROR1 by breast cancer cell lines is associated with features of EMT. (A) Immunoblots of lysates from MDA-MB-231 transfected with CTRL-shRNA or ROR1-shRNA were probed with antibodies specific for ROR1 (top) or β-actin (bottom) as indicated on the left. (B) Mean amount of VIM and KRT19 (±SEM), as detected via qRT-PCR on triplicate samples. Data are shown as means±SEM; *P<0.05, **P<0.01, compared with CTRL-shRNA group.

Figure 48:
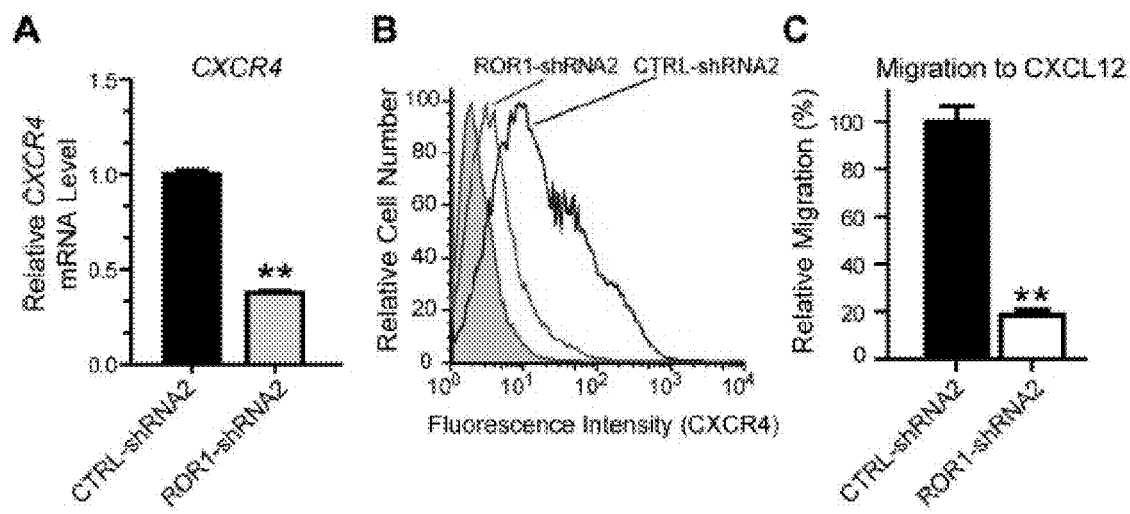

FIG. 48 shows silencing ROR1 reduces expression of CXCR4. (A) Histograms indicating the amount of CXCR4 mRNA detected via qRT-PCR in triplicate samples of MDA-MB-231 transfected with either CTRL-shRNA2 or ROR1-shRNA2, as indicated at the bottom of each histogram. (B) Representative flow cytometry fluorescence histograms of ROR1-shRNA2 (open histogram with green line) or CTRL-shRNA2 (open histogram with blue line) transduced MDA-MB-231 cells stained with anti-CXCR4-APC mAb or isotype-control mAb (shaded histograms), respectively. (C) Cells were seeded into the top chambers of trans-wells without BD Matrigel™ to examine for chemotaxis to CXCL12, which added to a final concentration of 200 ng/ml to the bottom chambers. The cells that migrated after six-hours at 37° C. were enumerated under 10× magnification. The histograms each provides the numbers of migrated cells in each of three chambers seeded with MDA-MB-231 cells transfected either with CNTL-shRNA or ROR1-shRNA, as indicated at the bottom of the histogram. Results are representative of 3 independent experiments. Data are shown as means±SEM; *P<0.05, P<0.01, *P<0.001, compared with CTRL-shRNA group.

Figure 49:
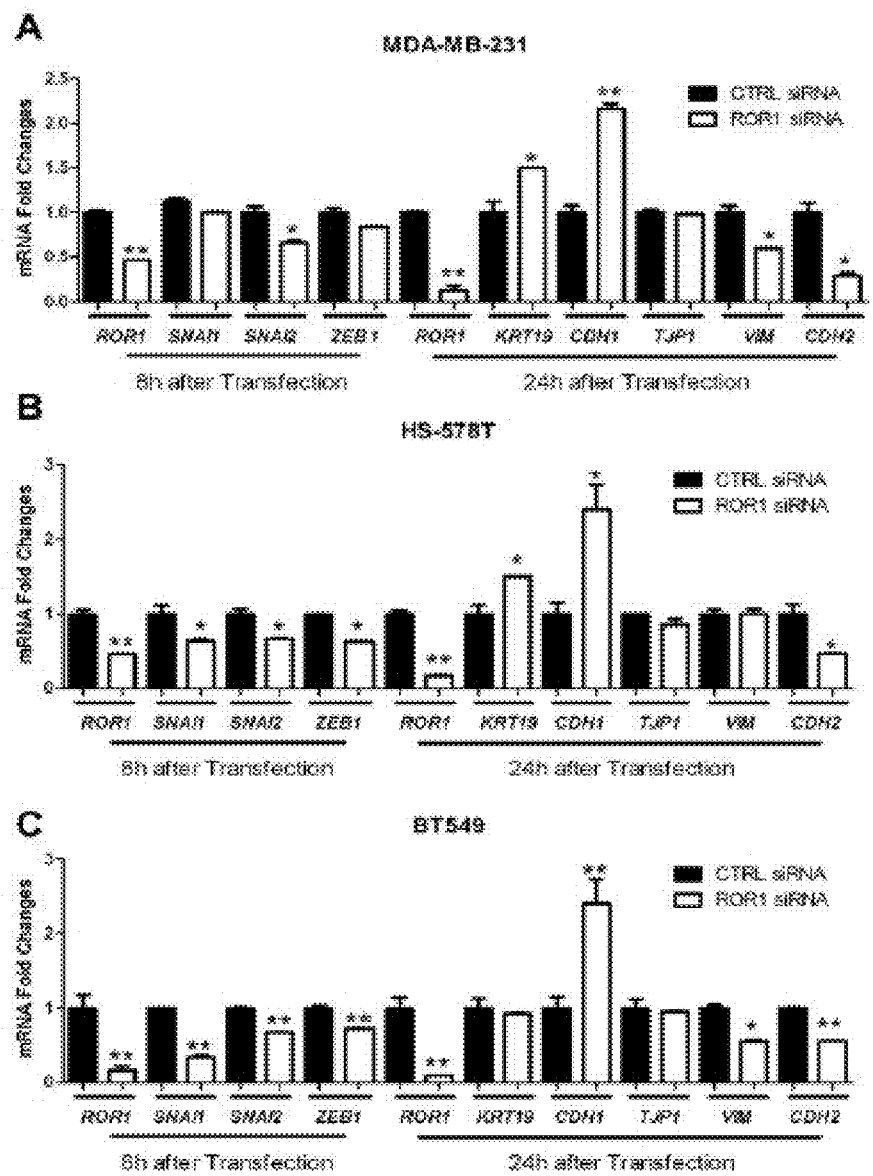

FIG. 49 shows silencing ROR1 regulates EMT genes expression. Histograms indicating the relative mRNA amount of variety genes, as indicated at the bottom of each histogram, detected via qRT-PCR in triplicate samples of MDA-MB-231(A), HS578T(B), and BT549(C) transfected with either CTRL-siRNA or ROR1-siRNA. Results are representative of 2 independent experiments. Data are shown as means±SEM; *P<0.05, **P<0.01, compared with CTRL-siRNA group.

Figure 50:
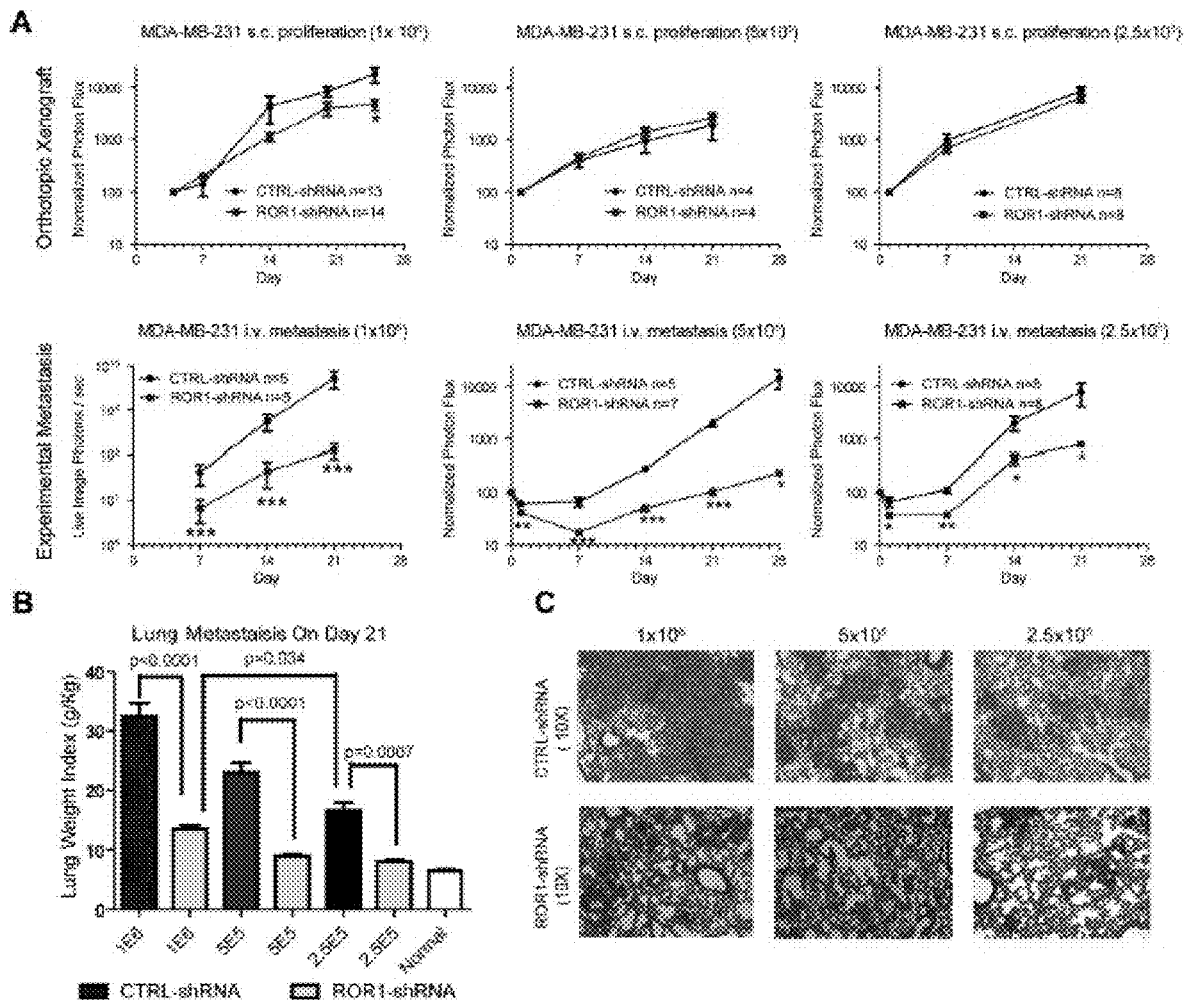

FIG. 50 shows silencing ROR1 effects modest late-growth inhibition of orthotopic xenografts at the site of injection but strong inhibition of experimental pulmonary metastases. (A) RAG−/−γc−/− mice were given subcutaneous (s.c.) or intravenous (i.v.) injections of CTRL-shRNA-transfected or ROR1-shRNA-transfected MDA-MB-231. The bioluminescence photon flux of the primary tumor in the injected mammary fat pad or of the lung of each mouse was normalized against the photon flux detected for the first measurement following the injection of tumor (100 represents 100% of the photon flux detected on the day of the initial measurement) (top panels). The top three graphs depict the normalized bioluminescence photo flux of the mammary fat pads of mice given s.c. injections of 1×10⁶ (left), 5×10⁵ (center), or 2.5×10⁵ (right) indicated cells. The bottom graphs provide normalized bioluminescence photo flux of the lung of mice given i.v. injections of 1×10⁶ (left), 5×10⁵ (center), or 2.5×10⁵ (right) indicated cells. (note: the bottom left graph depicts the actual mean bioluminescence photon flux of the lungs of mice given i.v. injections of 1×10⁶ indicated cells. (B) The histograms depict the lung-weight-index for mice of each group on d21 (n=5-8) i.v. injected with CTRL-shRNA-transfected (black) or ROR1-shRNA-transfected MDA-MB-231 (grey) or no cells (white). The P values were determined by One-way ANOVA. (C) H&E-stained sections of the lung representative of mice from each group on d21. Data are shown as means ±SEM *P<0.05, P<0.01, *P<0.001, compared with CTRL-shRNA group.

Figure 51:
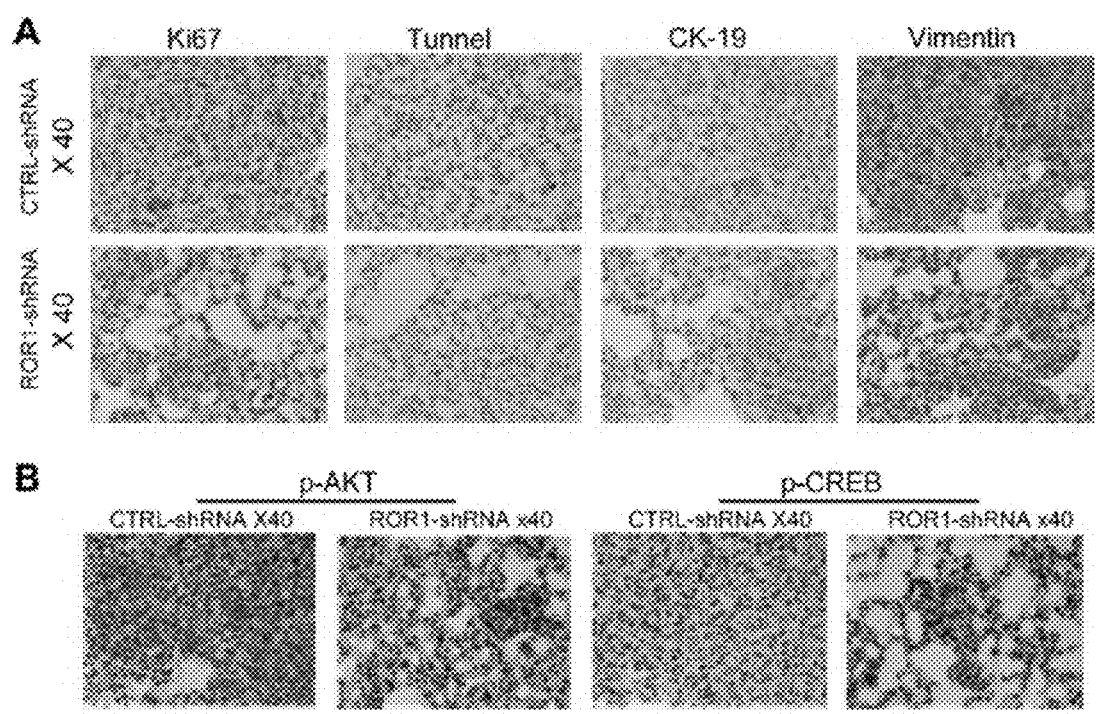

FIG. 51 shows immunohistochemistry of experimental metastatic foci. RAG−/−γc−/− mice were given intravenous (i.v.) injections of 5×10⁵ CTRL-shRNA-transfected MDA-MB-231 (top panels) or ROR1-shRNA-transfected MDA-MB-231 (bottom panels). (A) Sections of lung were prepared from animals euthanized on day 21. The lungs of mice injected with ROR1-shRNA-transfected cells had few metastatic foci, which were identified for immunohistochemistry analysis. The sections were stained with mAbs specific for Ki67+, CK-19, or vimentin, or terminal deoxynucleotidyl transferase dUTP nick end labeling (Tunnel). (40× magnification). (B) Sections of lung as in (a) were stained with mAb specific for phospho-AKT (left panel) or phospho-CREB (right panel) (40× magnification).

Figure 52:
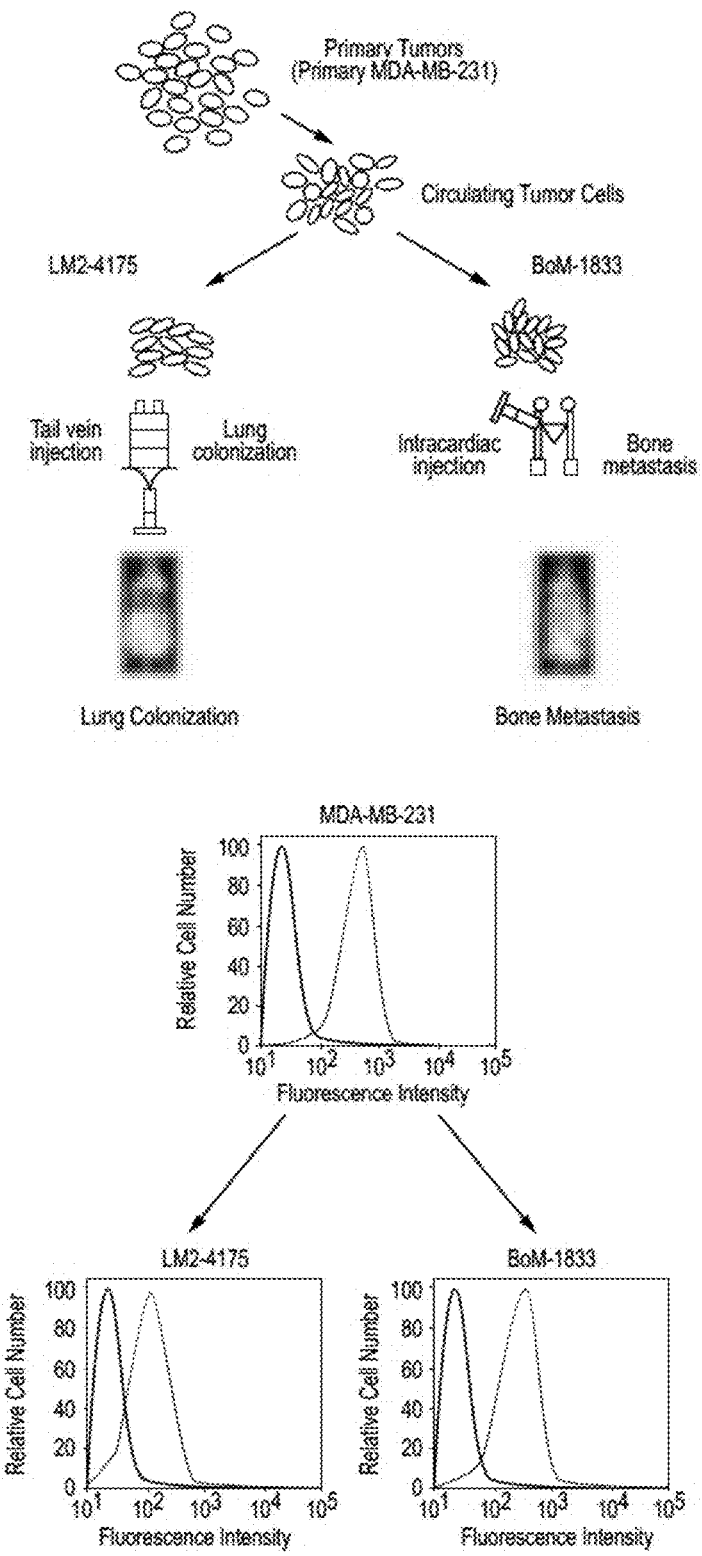
Figure 52:
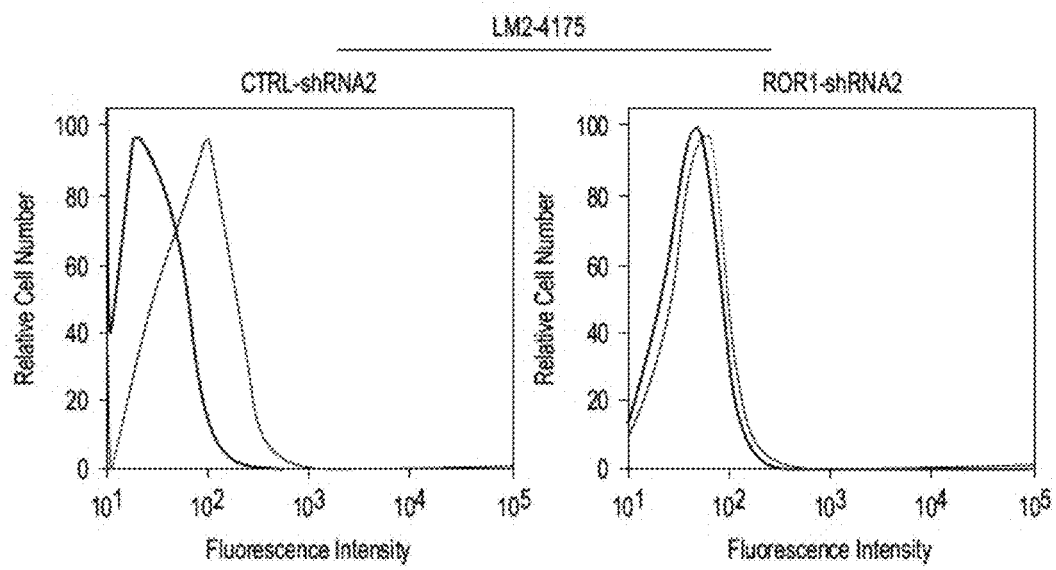
Figure 52:
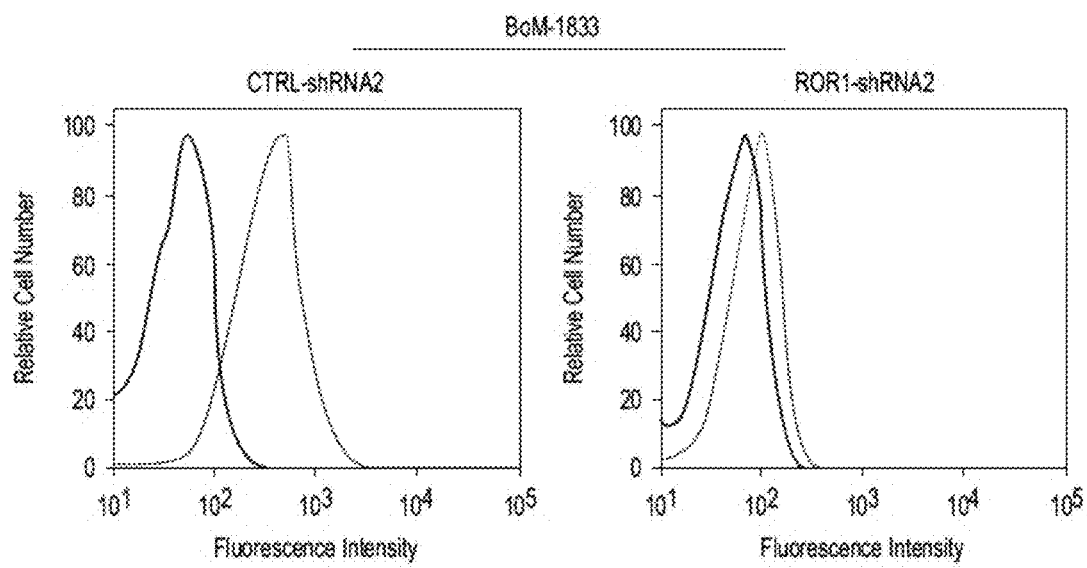
Figure 52:
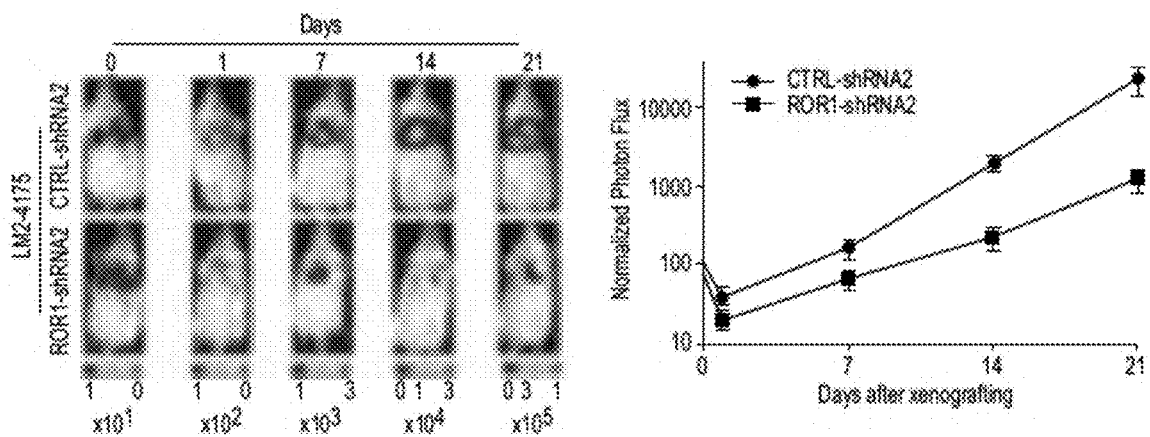
Figure 52:
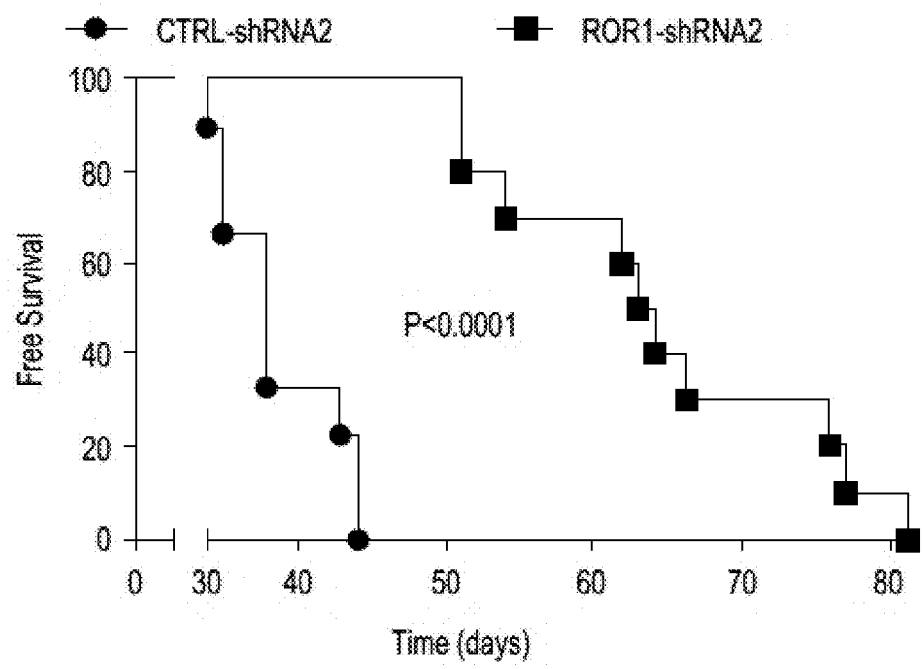
Figure 52:
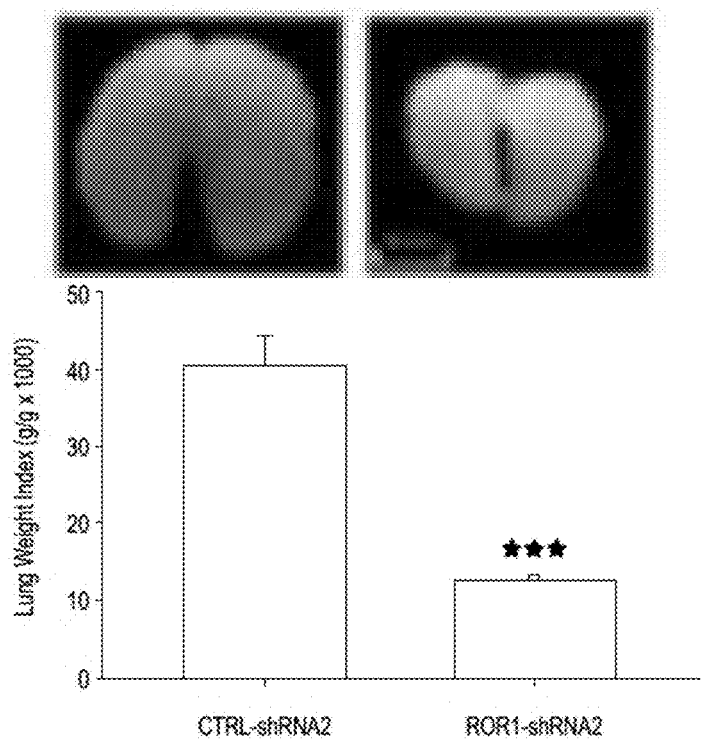
Figure 52:
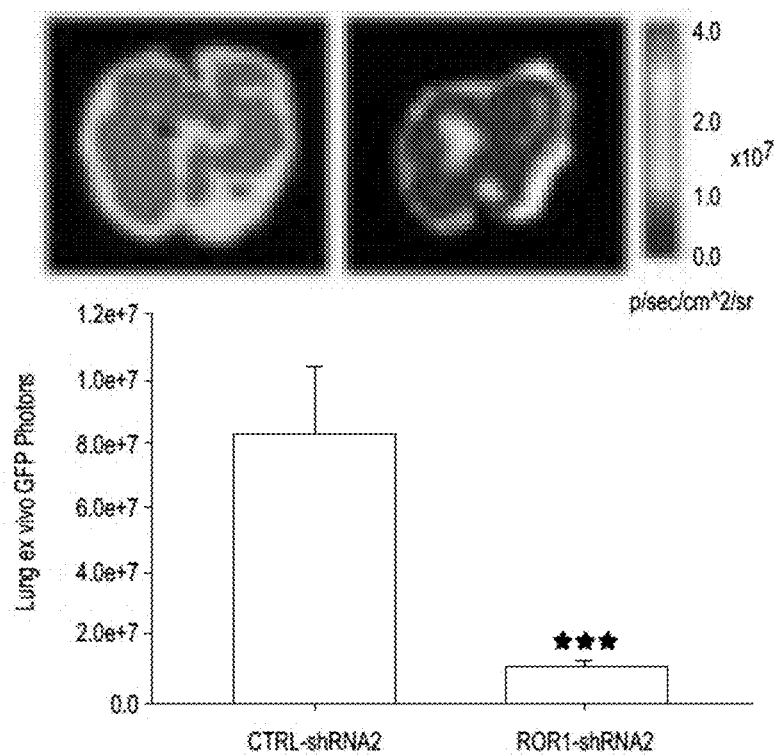
Figure 52:
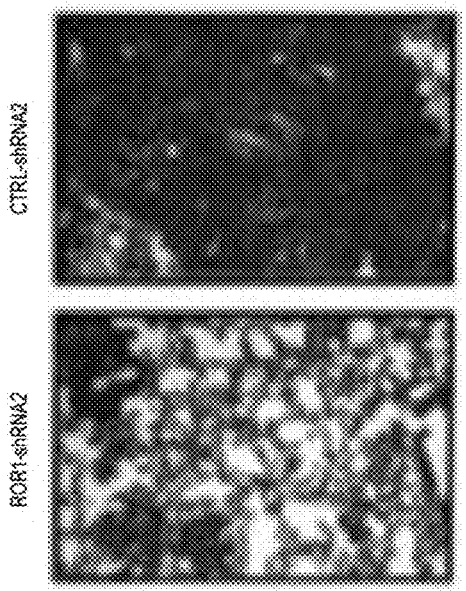
Figure 52:
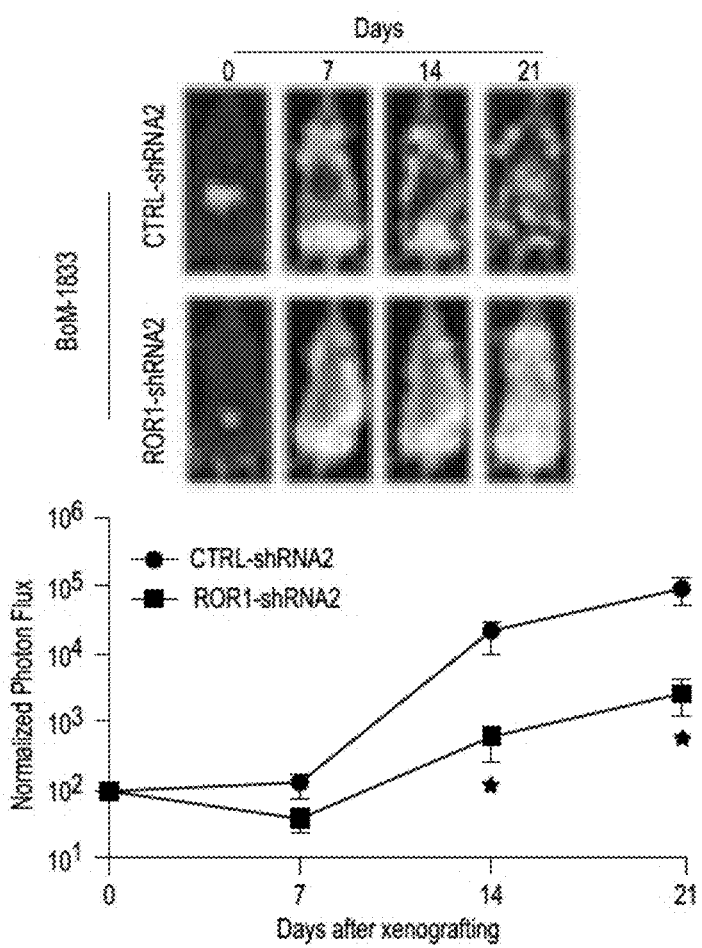
Figure 52:
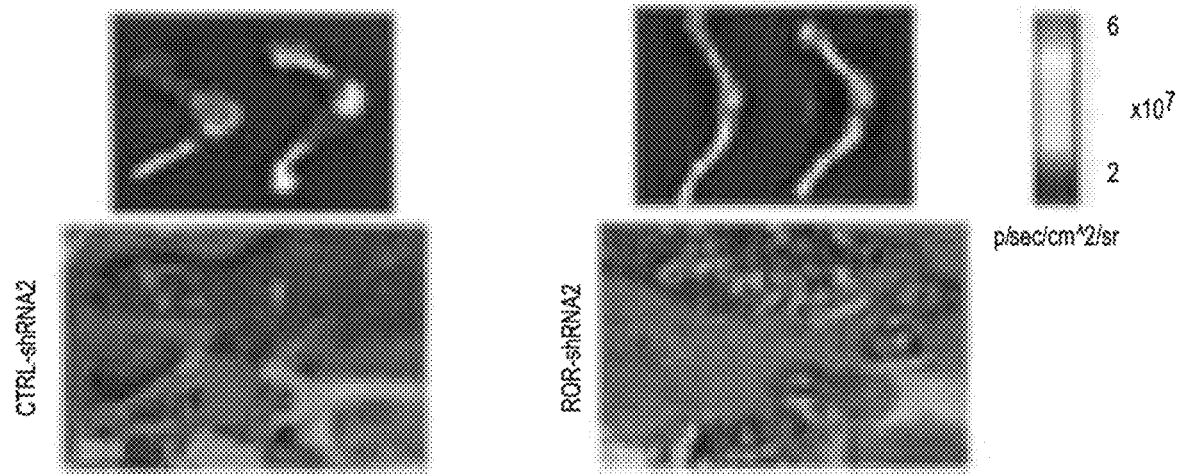
Figure 52:
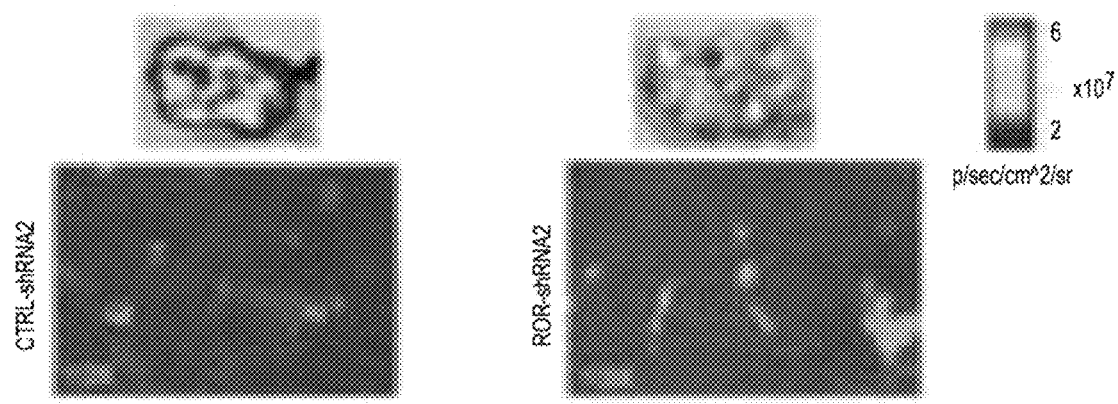

FIG. 52 shows silencing ROR1 reduces pulmonary metastasis and bone metastasis of MDA-MB-231 derived cell lines LM2-4175 and BoM-1833 in vivo. (A) Schematic diagram showing that LM2-4175 cells preferentially metastasize to lung and BoM-1833 cells preferentially metastasize to bone. Flow cytometry analyses showing the ROR1 expression in LM2-4175 and BoM-1833. Mouse cartoons are modified from reference (Cancer Cell, 2009; 1; 67-78) (B-C) Flow cytometry analyses showing the ROR1 silencing efficiency in LM2-4175 and BoM-1833, using ROR1-shRNA2. (D) Mice were each given an i.v. injection of 2×10⁵ CTRL-shRNA-transfected or ROR1-shRNA-transfected LM2-4175 cells. Left, representative bioluminescence images of each group; Right, normalized in vivo lung photon flux of each group. (E) Kaplan-Meier survival curves of mice injected i.v. with 2×10⁵ indicated LM2-4175 cells (P<0.0001 by log-rank test). (F) The lung-weight-index of each group on d21 (bottom). Representative photos of the lungs of each group (top). (G) The ex vivo lung GFP photon flux of each group on d21 (bottom). Representative photos of the bones of each group (top). (H) Representative H&E-stained histological sections of the lung on d21. (I) Mice were each given an i.c. injected of 1×10⁵ CTRL-shRNA-transfected or ROR1-shRNA-transfected BoM-1833 cells. Top, representative bioluminescence images of each group; Bottom, normalized in vivo bone photon flux of each group. (J) Representative bone ex vivo photon flux and H&E-stained histological sections of the bone on d21. (K) Representative liver ex vivo photon flux and H&E-stained histological sections of the liver on d21. Data are shown as means±SEM; *P<0.05, P<0.01, *P<0.001, compared with CTRL-shRNA group.

Figure 53:
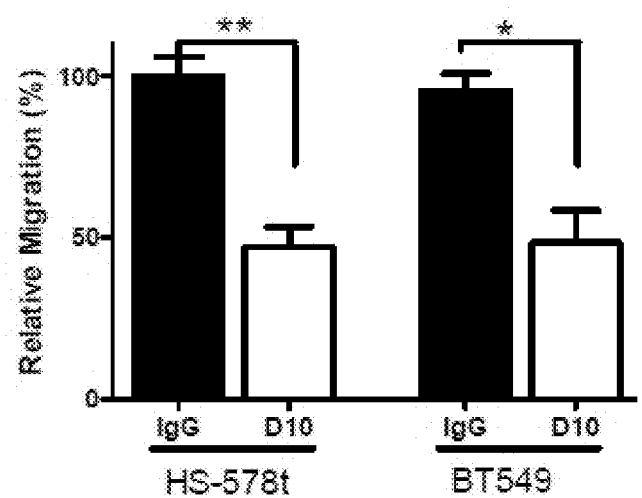

FIG. 53 shows silencing ROR1 inhibits migration of HS-578T and BT549 in vitro. Data are shown as the means±SEM *P<0.05, P<0.01, *P<0.001, compared with cells treated with control IgG.

DETAILED DESCRIPTION OF THE INVENTION

The present invention relates to the seminal discovery of compositions and methods of inhibiting metastasis using anti-ROR1 antibodies or antigen binding fragments thereof, ROR1 antibody immunoconjugates, ROR1 peptide vaccines or ROR1 binding peptides.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

ROR1

Applicants have previously discovered expression of full-length ROR1 in numerous cancer cell lines and samples, but not other tissues, including blood or splenic lymphocytes of non-leukemic patients or normal adult donors, and also generated mouse anti-sera against full-length human ROR1. Fukuda et al., Blood: ASH Annual Meeting Abstracts 2004 104, Abstract 772 (2004) (incorporated herein by reference in its entirety). The polypeptide and coding sequences for ROR1 have been reported elsewhere and are also incorporated herein by this reference (see, e.g., Accession Nos. NP 005003.1 and NM 005012.1). Cancer cells that express the Wnt5a protein, such as CLL cells, not only bind ROR1 but have a survival advantage conferred as a consequence. The invention therefore provides means to utilize the specificity of ROR-1 expression in cancer cells to treat or prevent cancer.

It has been shown that ROR1 expression enhances resistance to apoptosis and promotes cancer cell growth. As shown in the examples, expression of ROR1 associates with the epithelial-mesenchymal transition (EMT), which occurs during embryogenesis and cancer metastasis. High-level expression of ROR1 associates with enhanced rates of relapse and metastasis in patients with breast adenocarcinoma. Silencing ROR1 in metastasis-prone breast-cancer cell-lines attenuated expression of EMT-associated proteins (e.g. Vimentin, Snail-1/2, and ZEB), enhanced expression of epithelial cytokeratins and tight-junction proteins (e.g. CK-19 and ZO-1), and impaired their migration/invasion capacity and metastatic potential. Treatment of MDA-MB-231 with D10, a mAb specific for ROR1, down-modulate vimentin (which associates with ROR1) to inhibit cancer-cell migration. Administration of D10 to immune-deficient mice engrafted with MDA-MB-231 significantly inhibits tumor metastasis.

Antibodies

Certain embodiments comprise immunopeptides directed against the human ROR1 protein. The immunoglobulin peptides, or antibodies, described herein are shown to bind to the ROR1 protein. The ROR1 binding activity is specific; the observed binding of antibody to ROR1 is not substantially blocked by non-specific reagents. These ROR1 specific antibodies can be used to differentiate between ROR1 cells and normal cells. The ROR1 specific antibodies can also be used in immunotherapy against a ROR1 cancer, to determine the response after therapy for a ROR-1 cancer and to inhibit metastasis. Such immunopeptides can be raised in a variety of means known to the art As used herein, the term antibody encompasses all types of antibodies and antibody fragments, e.g., polyclonal, monoclonal, and those produced by the phage display methodology. Particularly preferred antibodies of the invention are antibodies that have a relatively high degree of affinity for ROR1. In certain embodiments, the antibodies exhibit an affinity for ROR1 of about $Kd<10^{-8}$ M.

Substantially purified generally refers to a composition which is essentially free of other cellular components with which the antibodies are associated in a non-purified, e.g., native state or environment. Purified antibody is generally in a homogeneous state, although it can be in either in a dry state or in an aqueous solution. Purity and homogeneity are typically determined using analytical chemistry techniques such as polyacrylamide gel electrophoresis or high performance liquid chromatography.

Substantially purified ROR-1-specific antibody will usually comprise more than 80% of all macromolecular species present in a preparation prior to admixture or formulation of the antibody with a pharmaceutical carrier, excipient, adjuvant, buffer, absorption enhancing agent, stabilizer, preservative, adjuvant or other co-ingredient. More typically, the antibody is purified to represent greater than 90% of all proteins present in a purified preparation. In specific embodiments, the antibody is purified to greater than 95% purity or may be essentially homogeneous wherein other macromolecular species are not detectable by conventional techniques.

Immunoglobulin peptides include, for example, polyclonal antibodies, monoclonal antibodies, and antibody fragments. The following describes generation of immunoglobulin peptides, specifically ROR1 antibodies, via methods that can be used by those skilled in the art to make other suitable immunoglobulin peptides having similar affinity and specificity which are functionally equivalent to those used in the examples.

Polyclonal Antibodies

Polyclonal antibodies may be readily generated by one of ordinary skill in the art from a variety of warm-blooded animals such as horses, cows, various fowl, rabbits, mice, or rats. Briefly, ROR1 antigen is utilized to immunize the animal through intraperitoneal, intramuscular, intraocular, or subcutaneous injections, with an adjuvant such as Freund's complete or incomplete adjuvant. Following several booster immunizations, samples of serum are collected and tested for reactivity to ROR1. Particularly preferred polyclonal antisera will give a signal on one of these assays that is at least three times greater than background. Once the titer of the animal has reached a plateau in terms of its reactivity to ROR1, larger quantities of antisera may be readily obtained either by weekly bleedings, or by exsanguinating the animal.

Monoclonal Antibodies

Monoclonal antibody (mAb) technology can be used to obtain mAbs to ROR1. Briefly, hybridomas are produced using spleen cells from mice immunized with human ROR1 antigens. The spleen cells of each immunized mouse are fused with mouse myeloma Sp 2/0 cells, for example using the polyethylene glycol fusion method of Galfre, G. and Milstein, C., Methods Enzymol., 73:3-46 (1981). Growth of hybridomas, selection in HAT medium, cloning and screening of clones against antigens are carried out using standard methodology (Galfre, G. and Milstein, C., Methods Enzymol., 73:3-46 (1981)).

HAT-selected clones are injected into mice to produce large quantities of mAb in ascites as described by Galfre, G. and Milstein, C., Methods Enzymol., 73:3-46 (1981), which can be purified using protein A column chromatography (BioRad, Hercules, Calif.). mAbs are selected on the basis of their (a) specificity for ROR-1, (b) high binding affinity, (c) isotype, and (d) stability.

mAbs can be screened or tested for ROR1 specificity using any of a variety of standard techniques, including Western Blotting (Koren, E. et al., Biochim. Biophys. Acta 876:91-100 (1986)) and enzyme-linked immunosorbent assay (ELISA) (Koren, E. et al., Biochim. Biophys. Acta 876:91-100 (1986)).

Humanized Antibodies

Humanized forms of mouse antibodies can be generated by linking the CDR regions of non-human antibodies to human constant regions by recombinant DNA techniques (see, e.g., Queen et al., Proc. Natl. Acad. Sci. USA 86:10029-10033, 1989 and WO 90/07861, each incorporated by reference). Human antibodies can be obtained using phage-display methods (see, e.g., Dower et al., WO 91/17271; McCafferty et al., WO 92/01047). In these methods, libraries of phage are produced in which members display different antibodies on their outer surfaces. Antibodies are usually displayed as Fv or Fab fragments. Phage displaying antibodies with a desired specificity may be selected by affinity enrichment.

Antibody Fragments

It may be desirable to produce and use functional fragments of a mAb for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains.

In addition, within the variable regions of the light and heavy chains there are hypervariable regions that contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Fab and F(ab')$_2$ fragments of mAbs that bind ROR-1 can be used in place of whole mAbs. Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

Recombinant DNA methods have been developed which permit the production and selection of recombinant immunoglobulin peptides which are single chain antigen-binding polypeptides known as single chain Fv fragments (ScFvs or ScFv antibodies). Further, ScFvs can be dimerized to produce a diabody. ScFvs bind a specific epitope of interest and can be produced using any of a variety of recombinant bacterial phage-based methods, for example as described in Lowman et al. (1991) Biochemistry, 30, 10832-10838; Clackson et al. (1991) Nature 352, 624-628; and Cwirla et al. (1990) Proc. Natl. Acad. Sci. USA 87, 6378-6382. These methods are usually based on producing genetically altered filamentous phage, such as recombinant M13 or fd phages, which display on the surface of the phage particle a recombinant fusion protein containing the antigen-binding ScFv antibody as the amino terminal region of the fusion protein and the minor phage coat protein g3p as the carboxy terminal region of the fusion protein. Such recombinant phages can be readily grown and isolated using well-known phage methods. Furthermore, the intact phage particles can usually be screened directly for the presence (display) of an antigen-binding ScFv on their surface without the necessity of isolating the ScFv away from the phage particle.

To produce an ScFv, standard reverse transcriptase protocols are used to first produce cDNA from mRNA isolated from a hybridoma that produces a mAb for targeting the ROR1 antigen. The cDNA molecules encoding the variable regions of the heavy and light chains of the mAb can then be amplified by standard polymerase chain reaction (PCR) methodology using a set of primers for mouse immunoglobulin heavy and light variable regions (Clackson (1991) Nature, 352, 624-628). The amplified cDNAs encoding mAb heavy and light chain variable regions are then linked together with a linker oligonucleotide in order to generate a recombinant ScFv DNA molecule. The ScFv DNA is ligated into a filamentous phage plasmid designed to fuse the amplified cDNA sequences into the 5' region of the phage gene encoding the minor coat protein called g3p. *Escherichia coli* bacterial cells are than transformed with the recombinant phage plasmids, and filamentous phage grown and harvested. The desired recombinant phages display antigen-binding domains fused to the amino terminal region of the minor coat protein. Such "display phages" can then be passed over immobilized antigen, for example, using the method known as "panning", see Parmley and Smith (1989) Adv. Exp. Med. Biol. 251, 215-218; Cwirla et al. (1990) Proc. Natl. Acad. Sci. USA 87, 6378-6382, to adsorb those phage particles containing ScFv antibody proteins that are capable of binding antigen. The antigen-binding phage particles can then be amplified by standard phage infection methods, and the amplified recombinant phage population again selected for antigen-binding ability. Such successive rounds of selection for antigen-binding ability, followed by amplification, select for enhanced antigen-binding ability in the ScFvs displayed on recombinant phages. Selection for increased antigen-binding affinity may be made by adjusting the conditions under which binding takes place to require a tighter binding activity.

Another method to select for enhanced antigen-binding activity is to alter nucleotide sequences within the cDNA encoding the binding domain of the ScFv and subject recombinant phage populations to successive rounds of selection for antigen-binding activity and amplification (see Lowman et al. (1991) Biochemistry 30, 10832-10838; and Cwirla et al. (1990) Proc. Natl. Acad. Sci. USA 87, 6378-6382).

Once an ScFv is selected, the recombinant ROR1 antibody can be produced in a free form using an appropriate vector in conjunction with *E. coli* strain HB2151. These bacteria actually secrete ScFv in a soluble form, free of phage components (Hoogenboom et al. (1991) Nucl. Acids Res. 19, 4133-4137). The purification of soluble ScFv from the HB2151 bacteria culture medium can be accomplished by affinity chromatography using antigen molecules immobilized on a solid support such as AFFIGEL™ (BioRad, Hercules, Calif.).

Other developments in the recombinant antibody technology demonstrate possibilities for further improvements such as increased avidity of binding by polymerization of ScFvs into dimers and tetramers (see Holliger et al. (1993) Proc. Natl. Acad. Sci. USA 90, 6444-6448).

Because ScFvs are even smaller molecules than Fab or F(ab')$_2$ fragments, they can be used to attain even higher densities of antigen binding sites per unit of surface area when immobilized on a solid support material than possible using whole antibodies, F(ab')$_2$, or Fab fragments. Furthermore, recombinant antibody technology offers a more stable genetic source of antibodies, as compared with hybridomas. Recombinant antibodies can also be produced more quickly and economically using standard bacterial phage production methods.

Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab').sub.2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to ROR1 antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Examples of scFv to human ROR1 include SEQ ID NO:21, SEQ ID NO:22, SEQ ID NO:23 and SEQ ID NO:24.

Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

Recombinant Antibody Production

To produce antibodies described herein recombinantly, nucleic acids encoding light and heavy chain variable regions, optionally linked to constant regions, are inserted into expression vectors. The light and heavy chains can be cloned in the same or different expression vectors. For example, the heavy and light chains of SEQ ID NOs: 1-5 can be used according to the present invention. The teachings of U.S. Pat. No. 6,287,569 to Kipps et al., incorporated herein by reference in its entirety, and the methods provided herein can readily be adapted by those of skill in the art to create the vaccines of the present invention. The DNA segments encoding antibody chains are operably linked to control sequences in the expression vector(s) that ensure the expression of antibody chains. Such control sequences may include a signal sequence, a promoter, an enhancer, and a transcription termination sequence.

Expression vectors are typically replicable in the host organisms either as episomes or as an integral part of the host chromosome. *E. coli* is one procaryotic host particularly useful for expressing antibodies of the present invention. Other microbial hosts suitable for use include bacilli, such as *Bacillus* subtilus, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda. Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired. Mammalian tissue cell culture can also be used to express and produce the antibodies of the present invention (see, e.g., Winnacker, From Genes to Clones VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line; baby hamster kidney cells (BHK, ATCC CCL 10); Chinese hamster ovary-cells (CHO); mouse sertoli cells; monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and TRI cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts (see, e.g., Sambrook et al., Molecular Cloning: A Laboratory Manual, Cold Spring Harbor Press, 2nd ed., 1989). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, e.g., Scopes, Protein Purification, Springer-Verlag, N.Y., 1982). Substantially pure immunoglobulins of at least about 90 to 95% homogeneity are preferred, and 98 to 99% or more homogeneity most preferred.

Multiple Specific Antibodies, Antibody Immunoconjugates and Fusion Molecules

ROR1 antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether an ROR1 antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an ROR1 antibody, binding polypeptide or antibody. Each binding domain specifically binds one epitope. When an ROR1 antibody, binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731, 168; 5,807,706; 5,821,333; and U.S. Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

The present invention includes multispecific ROR1 antibodies. For example, a bispecific antibody comprised of two scFv antibody fragments, both of which bind ROR1. The scFv antibody fragments may bind the same or different epitopes on ROR1. As an additional example, the multispecific antibody may be a diabody which binds to the epitopes of the antibodies with a heavy chain variable region selected from the group consisting of SEQ ID NO:1. SEQ ID NO:5, SEQ ID NO:9, SEQ ID NO: 13, SEQ ID NO:17, SEQ ID NO:39 or SEQ ID NO:42 and a light chain variable region selected from the group consisting of SEQ ID NO:3. SEQ ID NO:7, SEQ ID NO:11, SEQ ID NO: 15, SEQ ID NO:19, SEQ ID NO:41 or SEQ ID NO:45.

The invention further extends to fusion proteins. Fusion proteins are chimeric molecules that comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

ROR1 antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, ROR1-specific antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387. Radiolabled ROR1 antibodies of the invention will be particularly useful, while antibody drug conjugates (ADCs) remain to be developed.

ROR1 antibodies, or antigen-binding fragments, variants, or derivatives thereof of the invention include derivatives that are modified, i.e., by the covalent attachment of any type of molecule to the antibody such that covalent attachment does not prevent the antibody binding ROR1. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

ROR1 antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. ROR1-specific antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the ROR1-specific antibody, including the peptide backbone, the amino acid side-chains and the amino or carboxyl termini, or on moieties such as carbohydrates. It will be appreciated that the same type of modification may be present in the same or varying degrees at several sites in a given ROR1-specific antibody.

The present invention also provides for fusion proteins comprising an ROR1 antibody, or antigen-binding fragment, variant, or derivative thereof, and a heterologous polypeptide. The heterologous polypeptide to which the antibody is fused may be useful for function or is useful to target the ROR1 polypeptide expressing cells. In one embodiment, a fusion protein of the invention comprises a polypeptide having the amino acid sequence of any one or more of the VH regions of an antibody of the invention or the amino acid sequence of any one or more of the VL regions of an antibody of the invention or fragments or variants thereof, and a heterologous polypeptide sequence.

In another embodiment, a fusion protein for use in the treatment methods disclosed herein comprises a polypeptide having the amino acid sequence of any one, two, three of the VH-CDRs selected from the group consisting of SEQ ID NO:27, SEQ ID NO: 28 and SEQ ID NO:29 of an ROR1-specific antibody, or fragments, variants, or derivatives thereof, or the amino acid sequence of any one, two, three of the VL-CDRs selected from the group consisting of SEQ ID NO:30, SEQ ID NO:31 and SEQ ID NO:32 of an ROR1-specific antibody, or fragments, variants, or derivatives thereof, and a heterologous polypeptide sequence. In one embodiment, the fusion protein comprises a polypeptide having the amino acid sequence of a VH-CDR3 of an ROR1-specific antibody of the present invention, or fragment, derivative, or variant thereof, and a heterologous polypeptide sequence, which fusion protein specifically binds to at least one epitope of ROR1. In another embodiment, a fusion protein comprises a polypeptide having the amino acid sequence of at least one VH region of a ROR1-specific antibody of the invention and the amino acid sequence of at least one VL region of an ROR1-specific antibody of the invention or fragments, derivatives or variants thereof, and a heterologous polypeptide sequence. Preferably, the VH and VL regions of the fusion protein correspond to a single source antibody (or scFv or Fab fragment) that specifically binds at least one epitope of ROR1. In yet another embodiment, a fusion protein for use in the diagnostic and treatment methods disclosed herein comprises a polypeptide having the amino acid sequence of any one, two, three or more of the VH CDRs of an ROR1-specific antibody and the amino acid sequence of any one, two, three or more of the VL CDRs of an ROR1-specific antibody, or fragments or variants thereof, and a heterologous polypeptide sequence. Preferably, two, three, four, five, six, or more of the VH-CDR(s) or VL-CDR(s) correspond to single source antibody (or scFv or Fab fragment) of the invention. Nucleic acid molecules encoding these fusion proteins are also encompassed by the invention.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

The invention provides for a particularly preferred anti-human ROR1 antibody; i.e., an isolated anti-ROR1 antibody having the same binding specificity as antibody 99961. In one aspect, the antibody binds to the Ig-like domain that is contiguous with the CRD domain of ROR1. In an additional aspect, the antibody binds to amino acids 42-160 of hROR1. In a further aspect, the antibody binds to amino acids 130-160 of ROR-1. In another aspect, the antibody requires glutamic acid at position 138 of hROR1 to be present for binding In an additional embodiment, the invention provides for an isolated anti-ROR1 antibody comprising a heavy chain variable region is selected from the group consisting of SEQ ID. NO:1, SEQ ID. NO:5, SEQ ID. NO:9, SEQ ID. NO:13, and SEQ ID. NO:17, and the light chain variable region is selected from the group consisting of SEQ ID. NO:3, SEQ ID. NO:7, SEQ ID. NO:11, SEQ ID. NO:15 and SEQ ID. NO:19. In one aspect, the antibody according the heavy chain variable region is SEQ ID NO:5 and the light chain variable region is SEQ ID NO:7.

In one embodiment, the invention provides for an isolated anti-human ROR1 antibody comprising a heavy chain variable region comprised of CDR1, CDR2 and CDR3 selected from the group consisting of SEQ ID. NO:27, SEQ ID. NO:28, SEQ ID. NO:29, SEQ ID. NO:33, SEQ ID NO:34 and SEQ ID. NO:35, and the light chain variable region comprised of CDR1, CDR2 and CDR3 selected from the group consisting of SEQ ID. NO:30, SEQ ID. NO:31, SEQ ID. NO:32, SEQ ID. NO:36, SEQ ID NO:37 and SEQ ID. NO:38. In one aspect the a heavy chain variable region comprised of CDR1, CDR2 and CDR3 is comprised of SEQ ID. NO:27, SEQ ID. NO:28 and SEQ ID. NO:29, and the light chain variable region comprised of CDR1, CDR2 and CDR3 selected from the group consisting of SEQ ID. NO:30, SEQ ID. NO:31 and SEQ ID. NO:32.

In a further embodiment, the invention provides for an anti-human ROR1 antibody with a binding affinity greater than 41 nM. In an aspect, the antibody binding affinity is between about 4 nM and about 6 nM. In one aspect, the antibody binding affinity is about 5 nM.

In another aspect, the antibody inhibits metastasis. In an additional aspect, the antibody internalizes and inhibits cell migration. In a further aspect, the antibody internalizes and down modulates vimentin, snail1/2 or ZEB. In another aspect, the antibody is human, humanized or chimeric.

One embodiment of the invention provides for a pharmaceutical formulation comprising the antibody against ROR1 and a pharmaceutically acceptable carrier. In an additional embodiment, the invention provides an isolated nucleic acid encoding the antibody against ROR1. In another embodiment, the invention provides for an expression vector comprising the nucleic acid according to nucleic acid encoding an antibody against ROR1. In an additional embodiment, the invention provides for a host cell comprising the nucleic acid encoding an antibody against ROR1. In a further embodiment, the invention provides for a method of producing an anti-ROR1 antibody comprising culturing the host cells under conditions to produce the antibody. In one aspect, the method of producing an antibody further comprises recovering the antibody.

As shown in the examples, anti-ROR1 antibody D10 inhibits mouse and human CLL engraftment, can direct complement-dependent cytotoxicity, induces significant reduction in leukemic burden, and blocks metastasis of breast cancer cells to lung and bone.

D10 has been shown to have biologic activity while other known anti-ROR1 antibodies (e.g., 4A5 and K19) do not exhibit biologic activity despite 4A5 having a significantly higher binding affinity for ROR1. Antibody 4A5 has been shown to bind to different epitopes than D10. It has also been shown that a subset of cancer patients, in which the cancer is ROR+, antisera to ROR1 is produced. A further subset of patients make antibodies that inhibit Wnt5a activity, thus leading to the conclusion that not all ROR1 antibodies have biologic activity.

As described further in the Examples, epitope mapping was performed to determine the epitope of D10 and 4A5.

These studies determined that D10 binds to an epitope at the C-terminus of the Ig like domain that is contiguous to the CRD on ROR1. The epitope for 4A5 was also mapped to the Ig like domain, but closer to the amino terminal of the domain. These findings have led to the conclusion that antibodies which bind to the same epitope as D10 will inhibit ROR1 biologic activity while antibodies that bind elsewhere may not.

As shown in the examples, high affinity antibodies, i.e. 99961, were derived using the D10 epitope to select for high affinity recombinant antibodies. One of the selected antibodies, 99961 has a significantly higher binding affinity for ROR1 than D10. The 99961 antibody has 50× greater binding affinity than D10, i.e. 800 pM v. 41 nM. Additionally, 99961 was humanized generating four different antibodies. Experiments confirmed that 99961 has the same epitope as D10. Experiments confirmed that this epitope is not expressed on normal hematopoietic stem and progenitor cells. Further, 99961 does not cross react with normal adult tissues. This antibody also demonstrated activity against CLL cells, activity in ROR+ primary AML and induction of ROR1 internalization.

Vaccines

Additionally, the invention provides a vaccine for the treatment or prevention of cancer or the inhibition of metastasis in a subject that consists of a pharmaceutically acceptable composition of an isolated or synthetically produced ROR1 binding peptide. The invention also provides for a ROR1 binding peptide with at least 95% sequence identity to the ROR-1 binding region of D10. In a further aspect, the invention provides for a ROR1 binding peptide with at least 95%, 96%, 97%, 98%, 99% or 100% sequence identity to the binding region of D10. In one aspect, the binding region of D10 is VATNGKEVVSSTGVLFVKFGPC (SEQ ID NO:25). In an additional aspect, the binding region of D10 is EVVSSTGVLFVKFGPC (SEQ ID NO:26). In one aspect the D10 binding region is at least 22 amino acids. In a further aspect, the D10 binding region is at least 10, 11, 12, 13, 14, 15, 16, 17, 18, 19 20, 21 or 22 amino acids.

The present invention also provides for use of ROR1 binding peptide vaccines against diseases, such as a lymphoma, e.g., CLL, that involve the expression of ROR1. Because normal adult tissues do not appear to express ROR-1, it represents a tumor-specific antigen that can be targeted in active immune therapy. For example, the levels of ROR1 can be down-regulated by administering to the patient a therapeutically effective amount of a ROR1 binding peptide vaccine that produces in animals a protective or therapeutic immune response against ROR1 and the effects of its expression. The vaccines can include peptides. Methods of using such peptides include use in vaccines and for generating antibodies against ROR1. The ROR1 binding peptide may also include an immune adjuvant. The immunoadjuvant may be an immunogenic carrier moiety conjugated to the binding peptide. In one aspect, the immunogenic carrier moiety is a peptide. Examples of a suitable carrier for the vaccine further comprises an immunogenic adjuvant. In a further aspect, the adjuvant is an immunogenic carrier moiety conjugated to the binding peptide. The immunogenic carrier moiety may be a carrier peptide, such as keyhole limpet hemocyanin (KLH), bovine serum albumin (BSA), ovalbumin, aluminum hydroxide or other pharmaceutically acceptable immune adjuvant. Examples of pharmaceutically acceptable immune adjuvants can be found in Methods in Molecular Medicine, Vol. 42: Vaccine adjuvants: Preparation, Methods and Research Protocols; Edited by D. T. O'Hagan; Humana Press Inc., Totowa N.J. and European Agency for the Evaluation of Medicinal Products, Committee for Proprietary Medicinal Products, Guidelines on Adjuvants in Vaccines, London 2004. Typically the vaccine composition will also include a pharmaceutically acceptable carrier or diluent.

In one embodiment the invention provides for a vaccine against ROR-1 expressing cells, the vaccine comprising a pharmaceutically acceptable composition of an isolated or synthetically produced peptide having an amino acid sequence with at least 95% sequence identity to the ROR-1 binding region of antibody D10. In one aspect, the vaccine the amino acid sequence of the ROR-1 binding region of antibody D10 is VATNGKEVVSSTGVLFVKFGPC (SEQ ID NO:25). In a further aspect, the vaccine the amino acid sequence of the ROR-1 binding region of antibody D10 is EVVSSTGVLFVKFGPC (SEQ ID NO:26). In another aspect, the ROR1 expressing cell is a cancer cell. In an additional aspect, the cancer cell is from a B cell leukemia, lymphoma, CLL, AML, B-ALL, T-ALL, ovarian, colon, lung, skin, pancreatic, testicular, bladder, uterine, prostate, or adrenal cancer.

In another embodiment, the invention provides for a vaccine comprising a ROR1 binding peptide having an amino acid sequence with at least 95% sequence identity to VATNGKEVVSSTGVLFVKFGPC (SEQ ID NO:25) and a pharmaceutically acceptable carrier. In one aspect, the peptide is mammalian. In an additional aspect, the peptide is chimeric and/or of human, mouse, rat, porcine, bovine, primate, feline, canine, rabbit, goat, chicken or ursine origin. In another aspect, the vaccine further comprises an immunogenic adjuvant. In a further aspect, the adjuvant is an immunogenic carrier peptide conjugated to the binding peptide. In one aspect, the amino acid sequence of the binding peptide is VATNGKEVVSSTGVLFVKFGPC (SEQ ID NO:25). In another aspect, the immunogenic carrier peptide is keyhole limpet hemocyanin (KLH). The vaccine further comprises an immunogenic adjuvant. In a further aspect, the adjuvant is an immunogenic carrier moiety conjugated to the binding peptide. In one aspect, the amino acid sequence of the binding peptide is VATNGKEVVSSTGVLFVKFGPC (SEQ ID NO:25). The immunogenic carrier moiety may be a carrier peptide, such as keyhole limpet hemocyanin (KLH), bovine serum albumin (BSA), ovalbumin, aluminum hydroxide or other pharmaceutically acceptable immune adjuvant. Examples of pharmaceutically acceptable immune adjuvants can be found in Methods in Molecular Medicine, Vol. 42: Vaccine adjuvants: Preparation, Methods and Research Protocols; Edited by D. T. O'Hagan; Humana Press Inc., Totowa N.J. and European Agency for the Evaluation of Medicinal Products, Committee for Proprietary Medicinal Products, Guidelines on Adjuvants in Vaccines, London 2004.

In another embodiment, the invention provides for a vaccine comprising a ROR1 binding peptide having an amino acid sequence with at least 95% sequence identity to EVVSSTGVLFVKFGPC (SEQ ID NO:26) and a pharmaceutically acceptable carrier. In one aspect, the peptide is mammalian. In an additional aspect, the peptide is chimeric and/or of human, mouse, rat, porcine, bovine, primate, feline, canine, rabbit, goat, chicken or ursine origin. In another aspect, the vaccine further comprises an immunogenic adjuvant. In a further aspect, the adjuvant is an immunogenic carrier peptide conjugated to the binding peptide. In one aspect, the amino acid sequence of the binding peptide is EVVSSTGVLFVKFGPC (SEQ ID NO:26). The immunogenic carrier moiety may be a carrier peptide, such as keyhole limpet hemocyanin (KLH), bovine serum albumin (BSA) ovalbumin, aluminum hydroxide or other pharmaceutically acceptable immune adjuvant. Examples of pharmaceutically acceptable immune adjuvants can be found in Methods in Molecular Medicine, Vol. 42: Vaccine adjuvants: Preparation, Methods and Research Protocols; Edited by D. T. O'Hagan; Humana Press Inc., Totowa N.J. and European Agency for the Evaluation of Medicinal Products, Committee for Proprietary Medicinal Products, Guidelines on Adjuvants in Vaccines, London 2004.

In an additional embodiment, the invention provides for a pharmaceutical formulation comprising the vaccine comprising a ROR1 binding peptide having an amino acid sequence with at least 95% sequence identity to VATNGKEVVSSTGVLFVKFGPC (SEQ ID NO:25) and a pharmaceutically acceptable carrier.

In an additional embodiment, the invention provides for a pharmaceutical formulation comprising the vaccine comprising a ROR1 binding peptide having an amino acid sequence with at least 95% sequence identity to EVVSSTGVLFVKFGPC (SEQ ID NO:26) and a pharmaceutically acceptable carrier.

As shown in the examples, peptide vaccines were developed as shown in FIG. 18. Three peptides were used based on the epitopes of ROR1 antibodies D10, 4A5 and K19. Animals were immunized with the three peptides. All three peptides induced the production of ROR1 antisera. The results demonstrate that immunization with R22 peptide produced the greatest antibody titer. As indicated in the examples, the ROR1 antisera binds to ROR1, decreases leukemic burden, induce ROR1 internalization, mediate complement dependent cytotoxicity, inhibit breast cancer cell migration and inhibit engraftment of ROR+ leukemia cells. Thus, the invention provides a method to immunize patients against ROR1 to allow for the induction of antibodies to inhibit the capacity of ROR+ cancer cells to migrate and metastasize.

ROR1 Binding Peptide

In one embodiment, the invention provides for a ROR1 binding peptide comprising the amino acid sequence selected from the group consisting of: SEQ ID NO:25 and SEQ ID NO:26. In one aspect, the peptide has an amino acid sequence with at least 95% sequence identity to VATNGKEVVSSTGVLFVKFGPC (SEQ ID NO:25). In another aspect, the peptide has an amino acid peptide sequence at least 95% sequence identity to EVVSSTGVLFVKFGPC (SEQ ID NO:26). In another aspect, the binding peptide is mammalian. In an additional aspect, the binding peptide is chimeric and/or of human, mouse, rat, porcine, bovine, primate, feline, canine, rabbit, goat, chicken or ursine origin.

In an embodiment, the invention provides for a pharmaceutical formulation comprising a ROR1 binding peptide comprising the amino acid sequence selected from the group consisting of: SEQ ID NO:25 and SEQ ID NO:26 and a pharmaceutically acceptable carrier.

In another embodiment, the invention provides for an isolated nucleic acid encoding a ROR1 binding peptide comprising the amino acid sequence of SEQ ID NO:25 and SEQ ID NO:26.

In another embodiment, the invention provides for an expression vector comprising the nucleic encoding a ROR1 binding peptide comprising the amino acid sequence of SEQ ID NO:25 and SEQ ID NO:26. In a further embodiment, the invention provides for a host cell comprising the nucleic acid encoding a ROR1 binding peptide comprising the amino acid sequence of SEQ ID NO:25 and SEQ ID NO:26. In an additional embodiment, the invention provides for a method of producing a peptide comprising culturing the host cell encoding a ROR1 binding peptide comprising the amino acid sequence of SEQ ID NO:25 and SEQ ID NO:26 under conditions to produce the binding peptide. In one aspect, the method to produce a peptide further comprises recovering the binding peptide.

Suppression of Metastasis

In one embodiment, the invention provides for a method of suppressing metastasis of ROR-1 expressing cancer, the method comprising disrupting epithelial-mesenchymal transition of tumor cells by administering an antibody having the binding specificity of monoclonal antibody 99961, a vaccine comprised of a peptide having an amino acid sequence with at least 95% sequence identity to the ROR-1 binding region of antibody D10, a ROR-1 binding peptide having an amino acid sequence with at least 95% sequence identity to VATNGKEVVSSTGVLFVKFGPC (SEQ ID NO:25) or a ROR-1 binding peptide having an amino acid sequence with at least 95% sequence identity to EVVSSTGVLFVKFGPC (SEQ ID NO:26). In one aspect, the ROR-1 expressing cancer is B cell leukemia, lymphoma, CLL, AML, B-ALL, T-ALL, ovarian, colon, lung, skin, pancreatic, testicular, bladder, uterine, prostate, or adrenal cancer.

The examples provide evidence that ROR1 antibodies, binding peptides and vaccines have the ability to inhibit ROR+ cancer cells from migrating or metastasizing.

Treatment

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "cancer" or "cancer cell" or "ROR1 expressing cancer" or "ROR1 expressing cancer cell" refers to all neoplastic cell growth and proliferation, whether malignant or benign, including all transformed cells and tissues and all cancerous cells and tissues. Cancer includes, but is not limited to neoplasms, whether benign or malignant, located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract. Such neoplasms, in certain embodiments, express, over-express, or abnormally express ROR1.

Cancer also includes but is not limited to B cell leukemia, lymphoma, CLL, AML, B-ALL, T-ALL, ovarian, colon, lung, skin, pancreatic, testicular, bladder, uterine, prostate, and adrenal cancer.

The anti-ROR1 antibodies, ROR1 binding peptides and ROR1 vaccines described herein can be used for the treatment or prevention of a ROR1 cancer or to inhibit metastasis of a ROR1 cancer cell in a subject.

Antibodies

In certain therapeutic embodiments, the selected antibody will typically be an anti-ROR1 antibody, which may be administered alone, or in combination with, or conjugated to, one or more combinatorial therapeutic agents. When the antibodies described herein are administered alone as therapeutic agents, they may exert a beneficial effect in the subject by a variety of mechanisms. In certain embodiments, monoclonal antibodies that specifically bind hROR-1 are purified and administered to a patient to neutralize one or more forms of hROR-1, to block one or more activities of hROR-1, or to block or inhibit an interaction of one or more forms of hROR-1 with another biomolecule.

The immunotherapeutic reagents of the invention may include humanized antibodies, and can be combined for therapeutic use with additional active or inert ingredients, e.g., in conventional pharmaceutically acceptable carriers or diluents, e.g., immunogenic adjuvants, and optionally with adjunctive or combinatorially active agents such as antineoplastic drugs.

In other embodiments, therapeutic antibodies described herein are coordinately administered with, co-formulated with, or coupled to (e.g., covalently bonded) a combinatorial therapeutic agent, for example a radionuclide, a differentiation inducer, a drug, or a toxin. Various known radionuclides can be employed, including 90Y, $^{123}$I, $^{125}$I, $^{131}$I, $^{186}$Re, $^{188}$Re, and $^{211}$At. Useful drugs for use in such combinatorial treatment formulations and methods include methotrexate, and pyrimidine and purine analogs. Suitable differentiation inducers include phorbol esters and butyric acid. Suitable toxins include ricin, abrin, diptheria toxin, cholera toxin, gelonin, Pseudomonas exotoxin, Shigella toxin, and pokeweed antiviral protein. These combinatorial therapeutic agents can be coupled to an anti-ROR1 antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Alternatively, it may be desirable to couple a combinatorial therapeutic agent and an antibody via a linker group as a spacer to distance an antibody from the combinatorial therapeutic agent in order to avoid interference with binding capabilities. A linker group can also serve to increase the chemical reactivity of a substituent on an agent or an antibody, and thus increase the coupling efficiency. It will be further evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be affected, for example, through amino groups, carboxyl groups, sulfhydryl groups or oxidized carbohydrate residues.

It may also be desirable to couple more than one agent to an anti-ROR1 antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A variety of routes of administration for the antibodies and immunoconjugates may be used. Typically, administration is intravenous, intramuscular, or subcutaneous.

It will be evident that the precise dose of the antibody/immunoconjugate will vary depending upon such factors as the antibody used, the antigen density, and the rate of clearance of the antibody. A safe and effective amount of an anti-ROR1 agent is, for example, that amount that would cause the desired therapeutic effect in a patient while minimizing undesired side effects. Generally, a therapeutically effective amount is that sufficient to promote production of one or more cytokines and/or to cause complement-mediated or antibody-dependent cellular cytotoxicity. The dosage regimen will be determined by skilled clinicians, based on factors such as the exact nature of the condition being treated, the severity of the condition, the age and general physical condition of the patient, and so on.

In an additional embodiment, the invention provides a method for treating or preventing a cancer in a subject, the method comprising administering to the subject an antibody having the binding specificity of monoclonal antibody 99961, a vaccine comprised of a peptide having an amino acid sequence with at least 95% sequence identity to the human ROR-1 binding region of antibody D10, a ROR-1 binding peptide having an amino acid sequence with at least 95% sequence identity to VATNGKEVVSSTGVLFVKFGPC (SEQ ID NO:25) or a ROR-1 binding peptide having an amino acid sequence with at least 95% sequence identity to EVVSSTGVLFVKFGPC (SEQ ID NO:26). In one aspect, the cancer is B cell leukemia, lymphoma, CLL, AML, B-ALL, T-ALL, ovarian, colon, lung, skin, pancreatic, testicular, bladder, uterine, prostate, or adrenal cancer.

Inhibition of Metastasis by Targeting ROR1.

The spread of neoplastic cells from its original site to distant areas of the body is responsible for 90% of cancer-related deaths. The metastatic process includes the physical translocation of primary tumor cells to a distant organ and subsequent colonization. Some poor-prognostic gene signatures suggest that cells in some primary tumors are predisposed to metastasis. However, understanding of the molecular and cellular determinants of metastasis is limited, and the processes whereby tumor cells undergo this event are largely unknown. Recent attention has focused on a cell-biological program called the epithelial-mesenchymal transition (EMT), which now is considered to factor prominently in tumor progression, acquisition of motility, invasiveness, metastasis, and self-renewal traits.

EMT confers on neoplastic epithelial cells the biological traits needed to accomplish most of the steps of the invasion-metastasis cascade. In both normal development and cancer metastasis, EMT appears regulated by contextual signals that epithelial cells receive from their microenvironment. Through use of multiple pathways involved in embryonic morphogenesis and wound healing, cancer cells can concomitantly acquire attributes that enable invasion and metastasis.

Work to define cancer stem cells (CSCs) that can account for metastasis or relapse of cancer after therapy has identified a variety of traits associated with one or more subpopulations of CSCs within various tumors. Some of these studies have found acquisition of phenotypic characteristic of cells in EMT can induce non-CSCs to enter into a CSC-like state. Therefore, metastatic cancer cells, which have presumably undergone EMT, may exhibit a CSC phenotype and acquire invasive properties that promote survival in the circulation, extravasation into a distant organ, angiogenesis, and uncontrolled growth at the metastatic sites.

As detailed further in the Examples, high-level expression of ROR1 in cancer cells is associated with higher rates of relapsed and/or metastatic disease. The effects of ROR1 expression and silencing in patients with adenocarcinoma of the breast, described in Example 1, illustrates practice of the invention to inhibit metastasis. As shown, silencing ROR1 expression in metastatic-prone breast cancer cell lines reverses phenotypic features associated with EMT and impairs migration, invasion, and metastasis in vitro and in vivo. Further, the inventive antibodies specific for ROR1 inhibit metastases of human breast cancer cells xenografted into immune-deficient mice. These studies identify a previously unknown pathway for breast cancer metastasis and validate ROR1 as a promising target for cancer treatment. Low ROR1 expression levels were correlated with longer metastasis-free survival, and more importantly, therapeutic targeting of ROR1 with anti-ROR1 antibodies can inhibit breast cancer metastasis development.

Metastasis is the spread of cancer cells from their primary location to other parts of the body. Once cancer becomes metastatic, it cannot be effectively treated by surgery or radiation therapy. Moreover, the predominant cause of cancer patient' mortality is metastasis. Receptor tyrosine kinases (RTKs) are known to play crucial roles in many cellular processes, including differentiation, proliferation, migration, angiogenesis and survival. Although ROR2 has been found to facilitate melanoma and prostate cancer cell metastasis, there is not a significant difference in ROR2 expression between aggressive and non-aggressive breast cancer cell lines. However, expression of ROR1 has a strong correlation with the aggressive breast cancer cell lines.

While the invention is not limited by theories as to its mechanism of action, it is notable that ROR1 activates genes that encode proteins implicated in breast cancer metastasis, such as Snail-1, Snail-2, TCF8/ZEB, CK-19, Vimentin, CXCR4. AKT was recently reported to be involved with functions of metastasis, including EMT, resistance to apoptosis and angiogenesis. As demonstrated in the Examples, ROR1 up-regulated AKT activity and exposure of MDA-MB-231 cells to anti-ROR1 antibody D10 reduced p-AKT activity. These data suggest that inhibition of ROR1-regulated AKT activation may be one mechanism by which D10 exerts its anti-tumor effect.

With respect to breast cancer metastasis in particular, using gene expression signatures it was found that expression of ROR1 in primary breast tumors is associated with breast cancer metastasis including bone, lung, and brain metastasis. Among 582 cases that were analyzed, the relapse rate was 55% in the ROR1 high group compared to 37% in the ROR1 low group. Importantly, this relapse rate increased to 63% in ROR1 the 75th-100th group. ROR1 expression is also strongly correlated with clinically aggressive breast cancer tumor markers, including ER–, PR–, and Her2–. Although there was no statistically significant difference between the groups based on the breast cancer T-stage, the percentage of ROR1 high patients increased from 51% to 77% in the T1 and T4 stages, respectively. Organ specific metastasis (breast cancer to lung or bone) was significantly inhibited by ROR1 knockdown according to the invention. These data suggest that ROR1 may regulate certain lung and bone specific-genes, such as CXCR4.

Human chemokines are comprised of a superfamily of 48 ligands that bind to 19 different G protein-coupled chemokine receptors. It has been hypothesized that metastatic tumor cells can 'hijack' chemokine receptor-mediated cell migration highways. Breast cancer tumor cells express selected chemokine receptors including CXCR4. Inhibition of the CXCL12-CXCR4 axis according to the invention can block the in vivo metastasis of the cell line MDA-MB 231 to the lung. MDA-MB-231 cells silenced for ROR1 had lower expression of CXCR4 than parental MDA-MB-231 or MBA-MB-231 transfected with CTRL-shRNA.

Using gene expression analysis, it was found that the expression of ROR1 was also associated with lung (FIG. 1B), bone (FIG. 1C), and brain (FIG. 1D) metastasis. Based on a hazard ratio analysis, ROR1 was determined to be an even better predictor of overall, bone, and lung metastasis than ER, PR and HER2. ROR1 can also be a metastasis-related predictor gene based on the overall relapse rate of breast cancer patients overall relapse by ER and ROR1 status. Although there was some difference between ER+ and ER– cases in the early stage of metastasis-free survival, only ROR1 low and ROR1 high cases had significantly differences in the late stages of metastasis-free survival. Thus, the invention provides a path to inhibit metastasis and improve patient survival.

In general, the dosage of administered ROR1 antibodies, ROR1 antibody components, binding peptide vaccine compositions, immunoconjugates thereof and fusion proteins will vary depending upon such factors as the patient's age, weight, height, sex, general medical condition and previous medical history. Typically, it is desirable to provide the recipient with a dosage of antibody component, vaccine, immunoconjugate or fusion protein that is in the range of from about 1 ng/kg to 20 mg/kg (amount of agent/body weight of patient), although a lower or higher dosage also may be administered as circumstances dictate.

Administration of antibodies, antibody components, vaccines, immunoconjugates or fusion proteins to a patient can be intravenous, intraarterial, intraperitoneal, intramuscular, subcutaneous, intrapleural, intrathecal, by perfusion through a regional catheter, or by direct intralesional injection. When administering therapeutic proteins, peptides or conjugates by injection, the administration may be by continuous infusion or by single or multiple boluses.

Those of skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catherization of lymphatic vessels, also provide a useful means of treating lymphomas.

Preferably, ROR1 antibodies, binding peptides, immunoconjugates thereof and fusion proteins are administered at low protein doses, such as 20 to 3000 milligrams protein per dose, given once, or repeatedly, parenterally. Alternatively, administration is in doses of 100 to 300 milligrams protein per dose, or 300 to 1000 milligrams protein per dose, 1000 to 2000 milligrams protein per dose.

The present invention also contemplates therapeutic methods in which ROR1 antibody components are radiolabeled or supplemented with radiolabeled immunoconjugate or fusion protein administration. In one variation, ROR1 antibodies are administered as or with low-dose radiolabeled ROR1 antibodies or fragments. As an alternative, ROR1 antibodies may be administered with low-dose radiolabeled ROR1-cytokine immunoconjugates. Those of ordinary skill in the art will be familiar with pharmaceutically acceptable radiolabelling molecules and their appropriate dosing levels. For reference, consider "low doses" of $^{131}$I-labeled immunoconjugates, wherein a preferable dosage is in the range of 15 to 40 mCi, while the most preferable range is 20 to 30 mCi. In contrast, a preferred dosage of $^{90}$Y-labeled immunoconjugates is in the range from 10 to 30 mCi, while the most preferable range is 10 to 20 mCi.

The invention in all its aspects is illustrated further in the following Examples. The Examples do not, however, limit the scope of the invention, which is defined by the appended claims.

Example 1

ROR1 is Associated with Early Metastatic Relapse in Breast Adenocarcinoma

Figure 1:
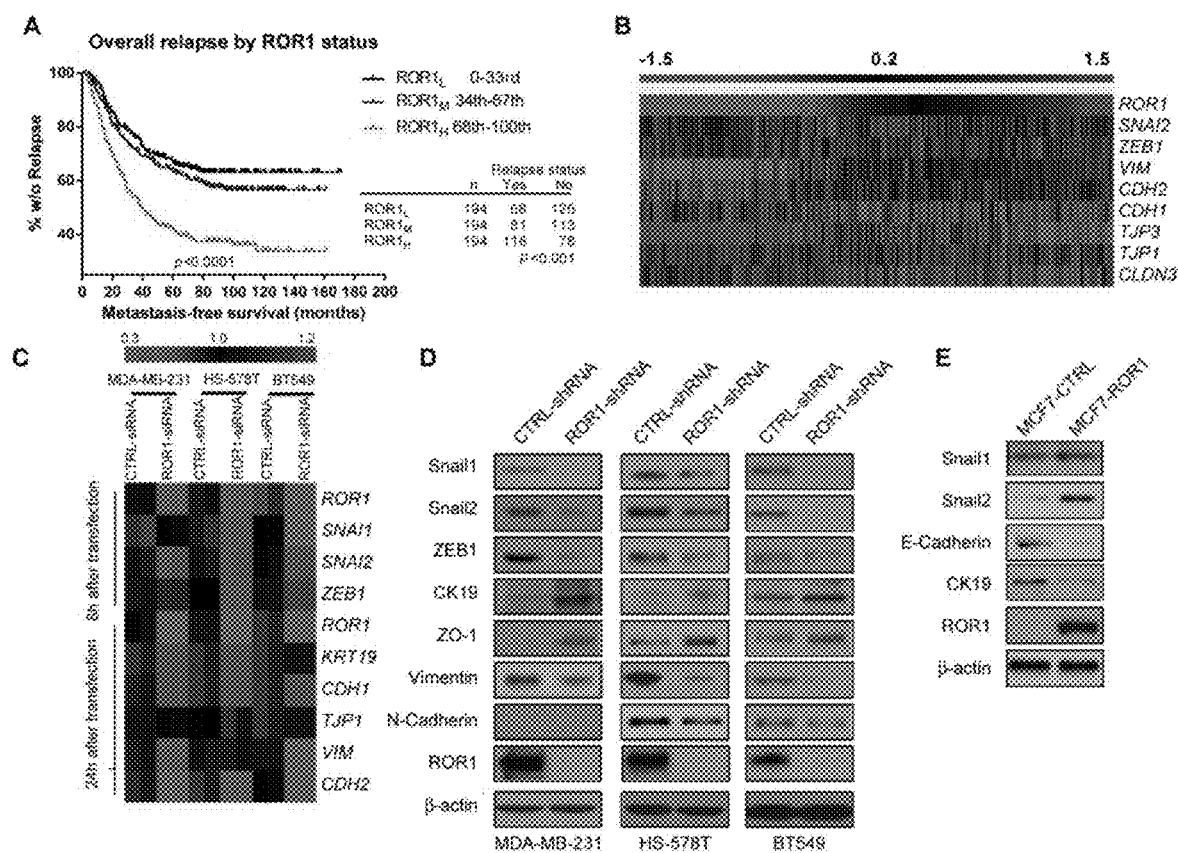
FIG. 1 shows high-level expression of ROR1 in breast cancer is associated with shorter metastasis-free survival and EMT gene signature. (A) The graph was derived from published data available through the PubMed GEO database (GSE2603, GSE5327, GSE2034, and GSE12276). Kaplan-Meier curves depict the prognostic impact of ROR1 expression on overall metastasis-free survival. For each analysis, 582 cases were segregated into tertiles with group designated ROR1H representing the one-third of the patients who had tumors with the highest levels of ROR1 mRNA, and the group designated ROR1L representing the one-third of patients who had cancers with the lowest levels of ROR1 mRNA. The one-third of patients who had tumors with intermediate expression of ROR1 mRNA was designated as ROR1M. Metastasis-free survival was determined by Kaplan-Meier analyses, and statistical differences were determined by log-rank test. The number of patients in each category, the total metastatic events, and the corresponding P values (chi-square test) are shown in the embedded tables. (B) Heat map showing the expression of ROR1 (top), EMT-related genes (SNAI1 and SNAI2 encoding Snail-1 and Snail-2, ZEB1 encoding ZEB-1, VIM encoding vimentin, CDH2 encoding N-Cadherin, CDH1 encoding E-Cadherin, TJP1 encoding ZO-1, TJP3 encoding ZO-3, KRT19 encoding CK-19, or CLDN3 encoding Claudin 3, in primary breast cancer cells isolated from patients. (C) Heat map showing the expression of EMT-related genes isolated from MDA-MB-231 (left), HS-578T (middle), BT549 (right) cells treated with ROR1-siRNA or CTRL-siRNA. (D) Immunoblots of protein lysates of MDA-MB-231, HS-578T, or BT549 (as indicated on the bottom) transfected with CTRL-shRNA or ROR1-shRNA, as indicated at the top. Immunoblots were probed with antibodies specific for the proteins indicated on the left. (E) Immunoblots of protein lysates of MCF7 transfected with a control vector or a ROR1-expressing vector, as indicated at the top. Immunoblots were probed with antibodies specific for the proteins indicated on the left.

The transcriptome data in the GEO database on breast cancer cells isolated from patients in a combined cohort of 582 patients was interrogated. Approximately two-thirds (426 of 582) of these cases did not have detectable cancer in the regional lymph nodes at the time of surgery and were not administered adjuvant therapy. The remaining cases had detectable disease in regional lymph nodes and received adjuvant hormonal therapy and/or chemotherapy. Among the 582 cases, 46% relapsed (n=270), and had a median metastasis-free survival time of 22.1 months. We segregated patients into three groups based upon their relative cancer-cell expression of ROR1. Patients with tumors having the upper-third level of ROR1 mRNA expression (ROR1H) had a significantly shorter metastasis-free survival than patients with tumors that had the lower-third-level (ROR1$_L$) or intermediate-level (ROR1$_M$) expression of ROR1 (p<0.0001; FIG. 1A). Metastasis-free survival by organ sites was examined. It was found that patients with ROR1H tumors had higher rates of metastasis to the lung (p=0.002; FIG. 45A), bone (p=0.004; FIG. 45B), or brain (p=0.04; FIG. 45C) than did patients with ROR1L or ROR1$_M$ breast cancers. ROR1H cancers had significantly lower proportions of tumors with favorable prognostic features, such as estrogen/progesterone receptors or HER2, than cancers with ROR1$_L$ or ROR1$_M$.

High-level expression of ROR1 also performed as an independent factor in predicting shorter metastasis-free survival. Patients with ROR1H tumors had a higher rate of metastasis, earlier relapse, and poorer survival than patients with ROR1$_{L/M}$ tumors, irrespective of ER, PR, or HER2 status (FIG. 46). Furthermore, interrogation of the GSE2034, GSE2603, GSE5327, and GSE12276 array data for EMT gene signatures in breast cancer revealed that ROR1L tumors had significantly higher expression levels of genes associated with epithelial cells, such as CDH1 (encoding E-cadherin), TJP1 (encoding ZO1), and TJP3 (encoding ZO3), but lower expression-levels of genes associated with mesenchymal cells, such as SNAI1 (encoding Snail-1), SNAI2 (encoding Snail-2), CDH2 (encoding N-Cadherin) or VIM (encoding Vimentin), than ROR1$_H$ tumors (FIG. 1B).

Example 2

ROR1+ Breast-Cancer Cell Lines

Fourteen distinct breast-cancer epithelial cell lines expression of ROR1 were examined, including six basal-type breast cancer cell lines and eight luminal-type breast cancer cell lines. The level of expression of ROR1 was significantly greater in basal-type breast cancer cell lines relative to that in luminal-type breast-cancer cell lines, which generally did not express ROR1. Moreover, the relative expression-levels of ROR1 correlated with aggressive tumor phenotypes, such as triple negative ER$^{Neg}$PR$^{Neg}$HER2/Neu$^{Neg}$, and high-level migration and invasion capacity in vitro.

ROR1 was silenced in highly-invasive, basal-type breast cancer cell lines (e.g. MDA-MB-231) using short hairpin RNAs (shRNAs) that targeted either of two different ROR1 sequences. Expression of ROR1 protein was inhibited in cells transfected with either ROR1-shRNA1 or ROR1-shRNA2, in contrast to cells transfected with a control shRNA (CTRL-shRNA) (FIG. 47A). Interrogation of the array data for gene-expression differences between MDA-MB-231 transfected with CTRL-shRNA or ROR1-shRNA (GEO accession: GSE31631) revealed that cells silenced for ROR1 had higher expression-levels of KRT19 (encoding CK19), lower expression-levels of CXCR4 and VIM than parental MDA-MB-231 or MDA-MB-231 transfected with CTRL-shRNA. These findings were confirmed by qRT-PCR (FIG. 47B, FIG. 48A). Flow cytometry analyses also demonstrated that cell-surface expression of CXCR4 was lower in cells silenced for ROR1 (FIG. 48B).

To assess the potential roles of ROR1 in the regulation of EMT, we examined for EMT-associated markers in cells treated with CTRL-shRNA or ROR1-shRNA. Suppressing expression of ROR1 with either ROR1-siRNA or ROR1-shRNA1/2 in either of three distinct, basal-type breast-cancer cell-lines (MDA-MB-231, HS-578T, or BT549) attenuated their expression of mRNA and/or encoded proteins associated with EMT (e.g. vimentin, SNAIL-1/2, and ZEB1). Conversely, silencing ROR1 increased expression of mRNA and encoded epithelial cytokeratins (e.g. CK-19). Although there were no significant changes in the TJP1 mRNA encoding ZO-1 in any of the 3 cell lines examined, cells silenced for ROR1 had higher expression levels of this tight-junction protein, suggesting that ZO-1 might be under post-transcriptional control (FIG. 1C-D and FIG. 49). Finally, transfection of ROR1-negative MCF7 cells to express ROR1 decreased expression of epithelial proteins (e.g. E-Cadherin and CK19), and increased expression of EMT transcriptional factors, such as SNAIL1/2 (FIG. 1E).

Figure 2:
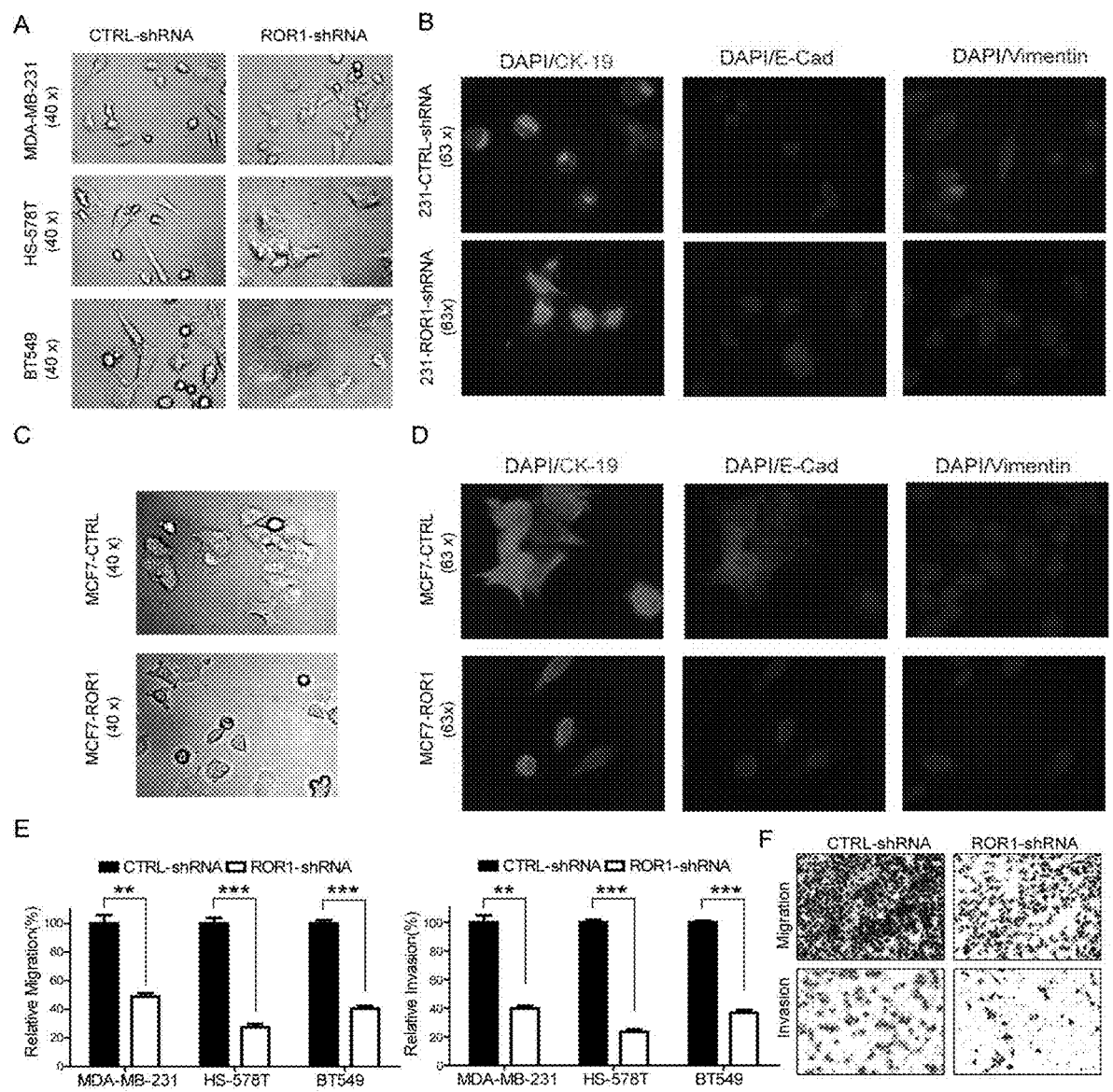
FIG. 2 shows expression of ROR1 by breast cancer cell lines is associated with features of EMT and higher metastatic potential. (A) Morphological changes (40×) of MDA-MB-231, HS-578T, or BT549 (as indicated on the left) transfected with CTRL-shRNA or ROR1-shRNA, as indicated at the top. (B) Expression of CK-19, E-cadherin, or vimentin were detected by immunofluorescence staining in MDA-MB-231 cells transfected with CTRL-shRNA or ROR1-shRNA under 63× magnification. (C) Morphological changes (40×) of MCF7 cells transfected with control vector or ROR1-expressing vector (as indicated at the top). (D) Expression of CK-19, E-cadherin, or vimentin was detected by immunofluorescence staining of MCF7 cells transfected with either control vector or ROR1-expression vector (63× magnification). (E) Assays for cell migration (left histograms) or invasion (right histograms) on MDA-MB-231, HS-578T, or BT549 transfected with either CTRL-shRNA (black) or ROR1-shRNA (white). All data were normalized to the results of cells transfected with CTRL-shRNA, which did not differ from those noted for the parental cell lines. Results are the mean value for each test group (±SEM) (n=3 per test group). (F) Representative photomicrographs of CTRL-shRNA-transfected MDA-MB-231 (left panels) or ROR1-shRNA-transfected MDA-MB-231 (right panels) in assays for cell-migration (top) or invasion (bottom). Data are shown as means±SEM; *P<0.05, P<0.01, *P<0.001, compared with CTRL-shRNA group.

In culture, MDA-MB-231, HS-578T, or BT549 cells typically had exhibited a stellate morphology, which is similar to that of mesenchymal cells in vitro. However, following transfection with ROR1-shRNA these cells assumed a more spherical morphology, which was similar to that of epithelial cells (FIG. 2A). Transfection of these cells with CTRL-shRNA did not induce such changes. Furthermore, immunofluorescence staining revealed that transfection with ROR1-shRNA induced MDA-MB-231 cells to express modest levels of E-cadherin and higher-levels of CK-19, but reduced expression of vimentin (FIG. 2B). Similar results also were observed for HS-578T or BT549 cells. On the other hand, compared to untreated cells or cells transfected with a control vector, ROR1-negative MCF7 cells developed a morphologic resemblance to mesenchymal cells and had decreased expression of epithelial markers (e.g. CK19 and E-Cadherin), and increased expression of mesenchymal markers, such as vimentin, when transfected to express ROR1. Furthermore, cells silenced for ROR1 had less migration/invasion capacity compared to that of cells treated with CTRL-shRNA (FIGS. 2E and F). It was also found that chemotaxis toward CXCL12 was significantly reduced in cells silenced for ROR1 (FIG. 48). Virtually identical results were obtained using cells silenced with either ROR1-shRNA1 or ROR1-shRNA2. Collectively, these results indicate that expression of ROR1 may contribute to EMT and tumor metastasis.

Example 3

Silencing ROR1 Inhibits Orthotopic Lung Metastasis

Cell Culture

The breast cancer cell lines MDA-MB-231, HS-578T, BT549,MDA-MB-415, MDA-MB-435s, MDA-MB-436, MDA-MB-157, MDA-MB-134, MCF7, BT-474, MDA-MB-453, SKBR3, MDA-MB-330, and BT-483 were obtained from American Type Culture Collection (ATCC) and maintained as previously described (Neve et al. Cancer Cell, 10:515 (2006)).

ROR1-Knockdown

Knockdown of ROR1 was achieved by targeting the sequences 5'-TCC GGA TTG GAA TTC CCA TG-3' (shRNA1), and 5'-CTT TAC TAG GAG ACG CCA ATA-3' (shRNA2) as previously described (Zhang, S. Et al., Cancer Cell, 16:67 (2009)). A nonspecific shRNA control was created by targeting the sequences 5'-AGC GGA CTA AGT CCA TTG C-3'. Virapower™ lentiviral expression systems (Invitrogen) were used to express the shRNA according to the manufacturer's instructions. The ROR1-shRNA1 and CTRL-shRNA1 constructs also encoded red fluorescence protein (RFP). Oligonucleotides for the ROR1-shRNA1 and CTRL-shRNA1 constructs were synthesized (Integrated DNA Technologies) and inserted into the RFP-pLKO.1 vector. ROR1-shRNA2 and CTRL-shRNA2 constructs were purchased from Open Biosystems (Rockford, Ill.). The viral particles for infection of breast cancer cells lines were obtained by transfection of the 293-FT packaging cell line, and collected from cell supernatants at 48 and 72 hrs post-transfection. Supernatants were filtered and centrifuged at 43,000×g to concentrate the viral particles, which were used to infect sub-confluent cultures in the presence of 5 μg/ml polybrene overnight.

Twenty-four hours post-transfection, cells were selected with 2 μg/ml puromycin. Knockdown cells were sorted by flow cytometry using an anti-ROR1 mAb (4A5). Sorted cells stably expressing shRNA1 or shRNA2 were designated ROR1-shRNA1 or ROR1-shRNA2, respectively. Pooled populations of knockdown cells, obtained in the first 10 generation after cell sorting without subcloning, were injected into rag−/−γ−/− mice for in vivo experiments. The efficiency of the knockdown of ROR1 was confirmed by quantitative PCR with reverse transcription (qRT-PCR) Sybr green gene expression assays (Applied Biosystems), or western immunoblot analysis (anti-ROR1 antibody, 54102, Cell Signaling). β2-microglobulin and actin were used as endogenous controls for qRT-PCR and western blot, respectively.

Trans-Well Migration and Invasion Assays

Cancer cells were conditioned overnight in Dulbecco's modified Eagle's medium supplemented with 0.2% fetal bovine serum (FBS) without growth factors. The following day, cells were trypsinized and resuspended in 0.2% FBS DMEM media without growth factors. Tumors cells were seeded at a density of 25,000 cells per well into trans-well inserts (3 μM pore size, BD Falcon) for migration assays or at a density of 50,000 cells per well into matrigel-coated, growth-factor-reduced, invasion chambers (8 μM pore size, BD Biosciences). Wells were washed with phosphate buffered saline (PBS) and fixed with 4% parafomaldehyde after 6 h for migration assays or after 22 h for invasion assays. The cells on the apical side of each insert were removed by scraping. Cells that had migrated to the basal side of the membrane were stained and visualized with a Nikon inverted microscope.

Analysis of mRNA and Protein Expression

Total RNA was purified using the RNeasy kit (Qiagen) and 2 μg of each sample was used for generating cDNA using the high-capacity cDNA Reverser transcription kits (ABI). Each cDNAs was analyzed in triplicate using an ABI 7500 Fast Real-Time PCR System (Applied Biosystem). Protein expression levels were assessed by immunoblot analysis with cell lysates (40-60 μg) in lysis buffer (20 mM HEPES (pH 7.9), 25% glycerol, 0.5 N NaCl, 1 mM EDTA, 1% NP-40, 0.5 mM dithiothreitol, and 0.1% deoxycholate) containing protease inhibitors (Roche) using anti-ROR1 (Cell Signaling) and anti-β-actin antibodies (Cell Signaling).

Flow Cytometry

Breast cancer cells were stained or pool sorted by flow cytometry. Cells were washed and resuspended in 2% bovine serum albumin (BSA) (Sigma) in PBS solution and stained for ROR1 expression using an Alex488-conjugated antibody (clone 4A5 or clone D10) or an Alex488-conjugated IgG2b or IgG2a isotype control according to the manufacturer's protocol. Flow cytometry data were collected using a FACSCalibur cytometer (BD Biosciences) and analyzed using FlowJo software.

Immunofluorescence and Immunohistochemistry Analysis

Mouse lungs were fixed with 4% paraformaldehyde and embedded in paraffin or frozen in OCT for histopathological examination. The tissue sections (5 μm thick) were prepared and stained with hematoxylin & eosin (H&E) or p-AKT (Ser473, D9E, Cell Signaling), p-Creb (Ser133, 87G3, Cell Signaling), CK-19 (RCK108, Dako), or Vimentin (D21H3, Cell Signaling) primary antibodies. Images were collected using a Delta Vision microscope and processed with SPOT software.

Analysis of Metastasis

Female Rag−/−γ−/− mice were injected with: a pool of parental MDA-MB-231 ROR1-shRNA1 cells (group 1), and control shRNA cells for parental MDA-MB-231 (group 2). Cells were injected intravenously through the lateral tail vein in 100 μl PBS ($5\times10^5$ for groups 1-2; $2\times10^5$ for groups 3-4) or administered by intracardiac injection in 100 μl PBS ($1\times10^5$ for groups 5-6). Non-invasive bioluminescence imaging was performed weekly by IVIS 200 imaging systems. All mice that had not previously died or appeared sick were euthanized at 3-4 wks post-injection, and their lungs were removed and fixed in 10% formalin.

To study the effect of ROR1 on the in vivo metastasis of a mammary pad xenograft, breast cancer tumors were induced in eight-week-old female Rag−/−γ−/− mice by injecting 100 μl of a single-cell suspension ($1\times10^6$ viable cells/mouse) subcutaneously into the second fat pad area of the right abdominal mammary gland. The tumor size was measured every 3 days. The tumors were removed when the tumor volumes reach 300 mm$^3$. To study the therapeutic effect of anti-ROR1 monoclonal antibodies in breast cancer metastasis, breast cancer tumors were induced in eight-week-old female Rag−/−γ−/− mice through intravenous injection 100 μl of a single-cell suspension ($5\times10^5$ cells/ mouse). Mouse IgG or anti-ROR1 mAbs were injected intravenously weekly. Non-invasive bioluminescence imaging was performed weekly. Five weeks after establishment of the xenograft, mice were sacrificed and lungs were removed and fixed in 10% formalin.

Oncomine Gene Expression Data Analysis

A microarray dataset of 582 patients from the Pubmed GEO database (GE02603, GSE5327, GSE2034 and GSE12276) was compiled. These datasets were transformed by log 2 and each microarray was centered to the median of all probes. For each patient, metastasis free survival was defined as the time interval between the surgery and the diagnosis of metastasis. Relative levels of ROR1 mRNA expression in human tissues were determined by Oncomine Cancer Microarray database analysis (available on the World Wide Web at the oncomine.org website) of a published gene expression data set. The data were log-2-transformed, with the median set to zero and s.d. set to one.

Statistical analyses. Comparisons between Kaplan-Meier curves were performed using the log rank test. Data are presented as means±standard error of the mean (SEM). An Unpaired Student's t test was used to compare two group unless otherwise indicated. A $p<0.05$ was considered statistically significant.

The performance of ROR1 in predicting metastasis-free survival was analyzed by multivariate analyses with Cox proportional hazard regression models. The hazard ratio of each covariate and its 95% confidence interval are reported. P-values are calculated based on the Normal Distribution, assessing the probability for the null hypothesis (hazard ratio=1, i.e. no prognostic significance) to be true.

Figure 3:
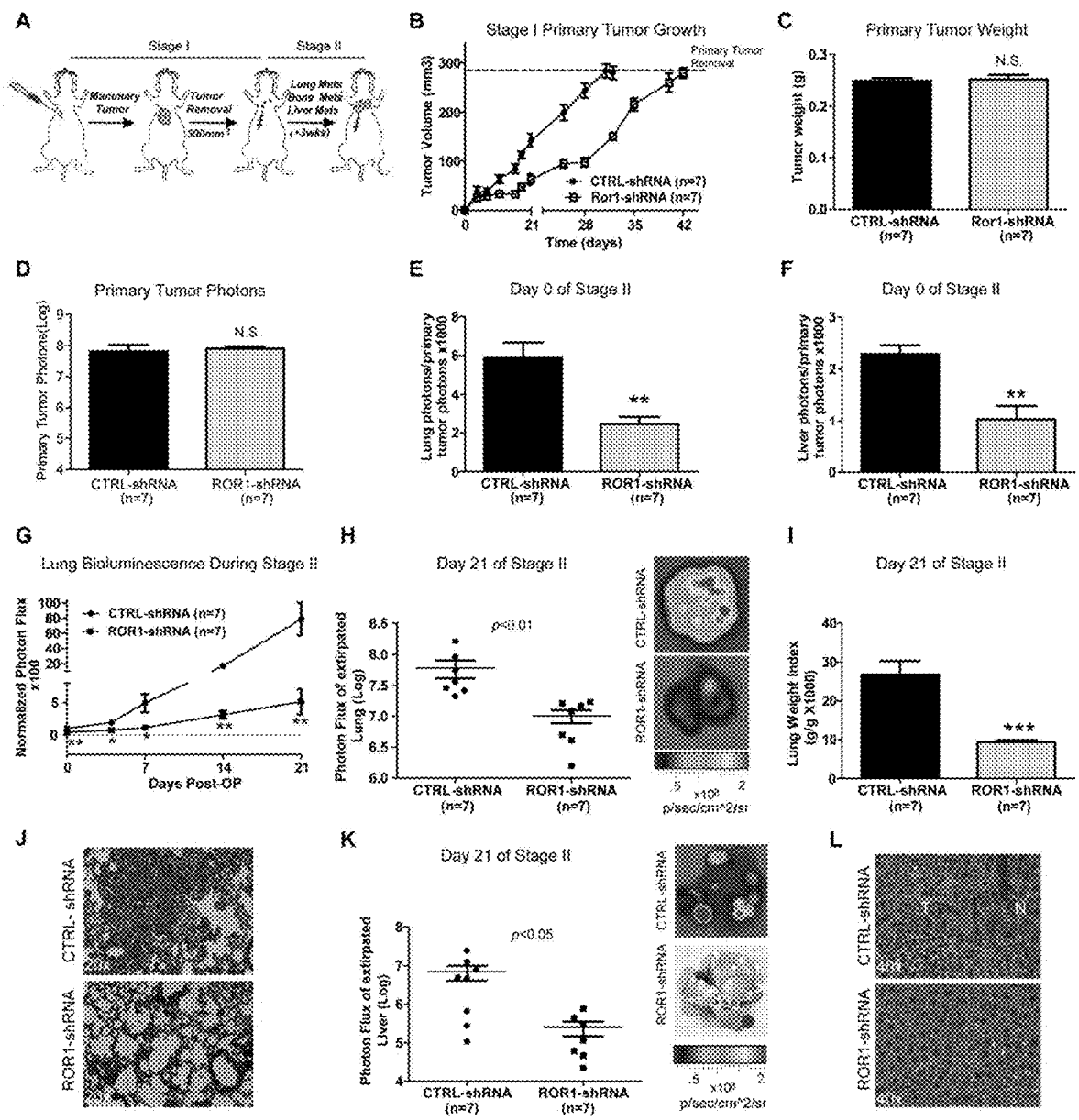
FIG. 3 shows ROR1 silencing reduces breast cancer metastasis after mammary pad xenograft. (A) Diagram depicting Stage I or II of the study. (B) Tumor volumes over time (days) during stage I. (C) Weight of the tumors excised from each group. (D) Ex vivo photon flux of primary tumors of each group. (E-F) The in vivo (e) lung photon flux or (f) liver photon flux of each mouse during stage II was normalized with primary-tumor photon flux for each mouse. Histograms depict the normalized lung and liver photon flux of each group. (G) The in vivo lung photon flux during stage II of each group. (H) Horizontal bars indicate mean ex vivo lung photon flux of mice on d21 for each group (left). To the right are representative bioluminescence images of the extirpated lungs from each group. (I) Histograms represent lung-weight-index for each group. (J) Representative H&E-stained lung sections. (K) Horizontal bars indicate mean ex vivo liver photon flux of mice on d21 for each group (left). To the right are representative bioluminescence-images of extirpated livers on d21 of each group. (L) Representative H&E-stained sections of the liver on d21 of mice injected for each group. Data are shown as means±SEM. Data are shown as means±SEM; P>0.05 is considered not significant (N.S.), *P<0.05, P<0.01, *P<0.001, compared with CTRL-shRNA group.

The metastatic potential of CTRL-shRNA-transfected was compared to ROR1-shRNA-transfected MDA-MB-231 cells that were stably transfected using a luciferase/GFP-expression vector in an orthotopic model (FIG. 3A). Injection of $2.5-10\times10^5$ cells into the subcutaneous mammary fat-pad of immune-deficient RAG−/−γc−/− mice generated primary tumors at the site of injection that we could monitor via bioluminescence. We did not observe significant differences in the progressive increases in bioluminescence of tumors that resulted from injection of CTRL-shRNA-transfected versus ROR1-shRNA-transfected cells until 3 or more weeks after the injection of at least $1\times10^6$ cells, as noted in prior studies. To examine for differences in the rates of 'spontaneous' cancer metastasis, the primary tumors resulting from injection of $1\times10^6$ cells were surgically removed when they reached a volume of 300 mm³ (dotted line, FIG. 3B). Because of different growth rates, the median number of days from cell-injection to surgical removal of the primary tumors was significantly greater for mice injected with cells silenced for ROR1 (40±2.5 days) than for mice that received equal numbers of CTRL-shRNA-transfected cells (31±0.5 days) (FIG. 3B). The extirpated primary tumors had similar volume, weight, and ex vivo bioluminescence (FIG. 3, C to E). Following the removal of the primary tumor we monitored for metastatic disease via bioluminescence. Animals injected with CTRL-shRNA-transfected cells had significantly greater bioluminescence in the lung or liver at the time of primary-tumor excision than did the mice engrafted with cells silenced for ROR1 at the later time when they had their primary tumors excised (FIGS. 3, E and F). Animals injected with cells silenced for ROR1 had less detectable increase in lung bioluminescence relative to that of mice injected with CTRL-shRNA-transfected cells (FIG. 3G). The animals were sacrificed 21 days after their primary tumors were excised to examine the ex vivo bioluminescence, size, and histology of the lung (FIG. 3, H to J) and liver (FIGS. 3, K and L). The extirpated lungs and livers of mice injected with CTRL-shRNA-transfected cells had significantly greater bioluminescence and weight than those of mice injected with ROR1-silenced cells. Moreover, the lungs and livers of mice injected with CTRL-shRNA-transfected cells universally had extensive metastatic disease, which was not observed in the tissues of mice injected with ROR1-silenced cells (FIGS. 3, J and L).

Example 4

Silencing ROR1 Inhibits Experimental Lung and Bone Metastasis

The ROR1-shRNA or CTRL-shRNA transfected MDA-MB-231 cells was administered to 6-week-old Rag−/−γ−/− mice via intravenous ($5\times10^5$ cells) or intracardiac ($1\times10^5$ cells) injection to evaluate for differences in metastatic potential of cells injected into either the venous or arterial blood. All animals that received CTRL-shRNA-transfected cells into the lateral tail vein died within 32 days of injection due to lung metastasis. Animals that had equal numbers of ROR1-shRNA-transfected cells injected into the tail vein survived significantly longer (FIG. 4A). Animals injected with CTRL-shRNA-transfected cells had 19-fold or 60-fold greater bioluminescence in the lungs at day 21 or day 28, respectively, than mice injected with cells silenced for ROR1 (FIG. 4B). We also sacrificed animals in another experiment at various times to examine the lungs for metastatic disease. Whereas nascent metastatic foci were readily detected at 3 days after injection of CTRL-shRNA-transfected cells, few, if any, metastatic foci could be detected in the lungs of animals injected with ROR1-silenced cells, even at later time points (FIG. 4C-E). Moreover the lungs extirpated from mice injected with CTRL-shRNA-transfected cells had significantly greater ex vivo bioluminescence and median weight (3-fold and 6-fold on days 21 and 28, respectively) than the lungs of mice injected with ROR1-silenced cells (FIG. 4F-G, data not shown). The metastatic foci that developed in animals injected with CTRL-shRNA-transfected cells also expressed higher levels of phospho-AKT and phospho-CREB and had higher proportions of proliferating cells than the few metastatic foci that we detected in mice injected with ROR1-silenced cells, which instead expressed higher levels of CK-19 and lower levels of vimentin (FIG. 4J).

Figure 4:
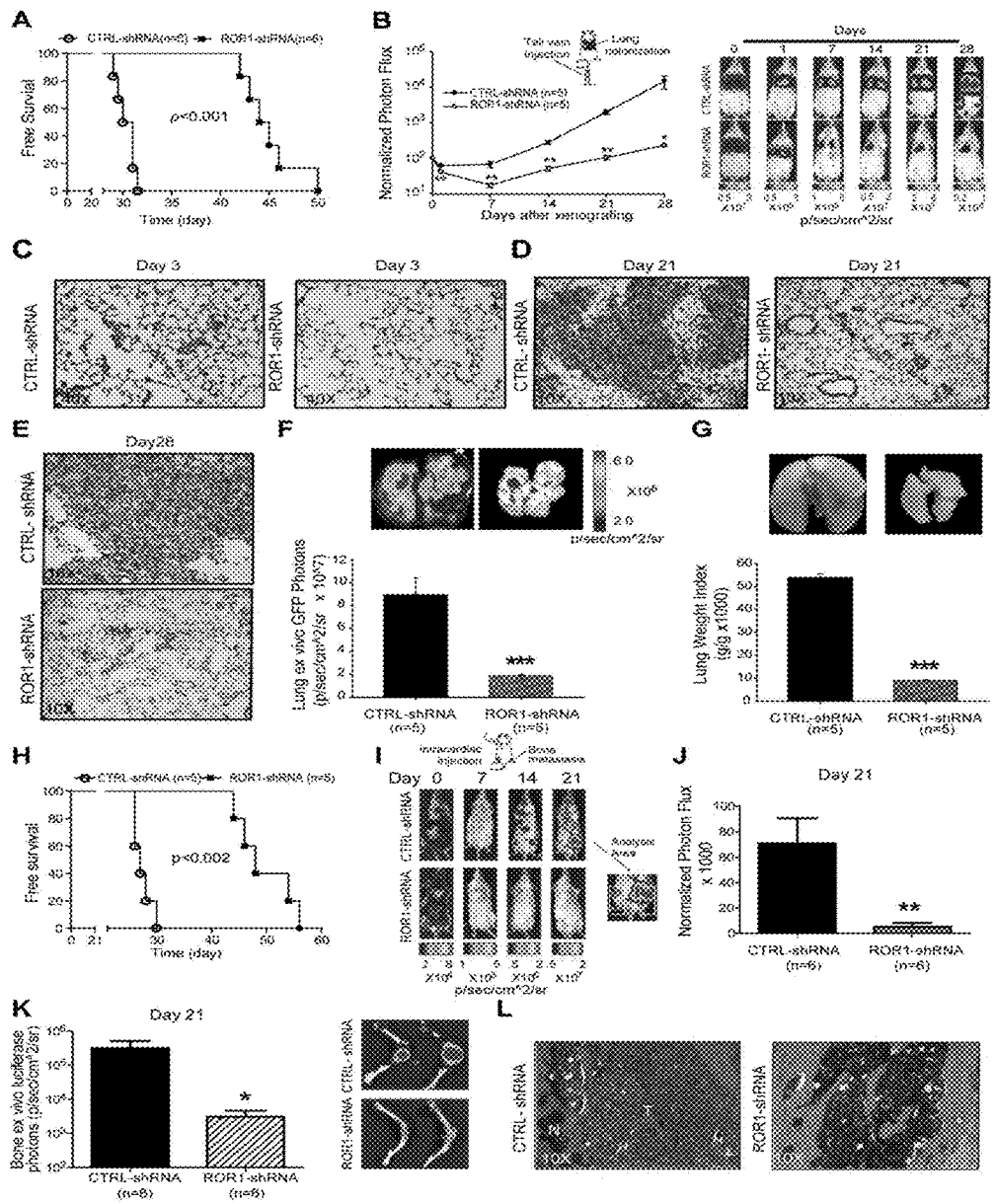
FIG. 4 shows ROR1 silencing reduces experimental pulmonary metastasis and bone metastasis of MDA-MB-231 cell in vivo. A) Kaplan-Meier survival curves of mice injected i.v. with 5×105 CTRL-shRNA-transfected or ROR1-shRNA-transfected cells (P<0.001 by log-rank test). (B) The in vivo lung photon flux of each group over time following injection (left). Representative bioluminescence images of mice from each group are depicted to the right. (C-E) Representative H&E-stained sections of the lung on (c) d3, (d) d21, and (e) d28. (F) Bottom histograms provide ex vivo lung GFP photon flux on d28 for each group. Representative bioluminescence images of the lungs extirpated on d28. (G) The lung-weight-index from each group on d28 (bottom). Representative photographs of the lungs (top) of each group. (H) Kaplan-Meier survival curves of mice injected i.c. with 1×105 CTRL-shRNA-transfected or ROR1-shRNA-transfected cells (P=0.0017 by log-rank test). (I) Representative bioluminescence images of mice following i.c. tumor injection. The white boxes define the area from which we acquired the bioluminescence data presented in (j). (J) The histograms provide the normalized in vivo bone photon flux of each group. (K) The ex vivo bone photon flux of the extracted pelvic bones of each group on d21. Representative bioluminescence images of the extracted pelvic bones are depicted to the right. (L) Representative H&E-stained histological bone sections of mice from each. Mouse cartoon is modified from reference (30). Data are shown as the means±SEM *P<0.05, P<0.01, *P<0.001, compared with CTRL-shRNA group.

We also examined for metastatic disease following injection of $1\times10^5$ cells into the left cardiac ventricle. All mice that received CTRL-shRNA-transfected cells died within 30 days of this injection, whereas animals injected with ROR1-silenced cells survived significantly longer (FIG. 4H). Mice injected with CTRL-shRNA-transfected cells developed substantial femoral/pelvic-area bioluminescence, which was not detected in mice injected with tumor cells silenced for ROR1 (FIGS. 4, I and J). We sacrificed animals on day 21 and found the isolated femoral/pelvic bones of mice injected with CTRL-shRNA-transfected cells had high bioluminescence (FIG. 4K) due to extensive marrow metastasis (FIG. 4L), which was not apparent in mice injected with cells silenced for ROR1.

Recent studies have found that different tissue-sites impose different requirements for the establishment of metastases by circulating cancer cells. Human breast cancer cell lines BoM1833 and LM2-4175 were selected from MDA-MB-231 to have different tissue tropism. BoM-1833 preferentially metastasizes to the bone and LM2-4175 preferentially metastasizes to the lung. We found that each of these cell lines retained expression of ROR1 (FIG. 5A). Transfection of each cell-line with ROR1-shRNA2 silenced expression of ROR1 (FIGS. 5B and C), allowing us to examine the ROR1-dependency of organ-specific metastasis following intravenous injection of 2×10$^5$ LM2-4175 or intracardiac injection of 1×10$^5$ BoM-1833 into 6-week-old RAG–/–γc–/– mice. Mice injected with LM2-4175 silenced for ROR1 had a significantly lower median increase in lung bioluminescence and significantly longer median survival than did mice injected with CTRL-shRNA-transfected LM2-4175 (FIGS. 5D and E). Consistent with these observations, the lungs of mice isolated 21 days after the injection of ROR1-silenced LM2-4175 had significantly lower median weight, ex vivo bioluminescence, and fewer and smaller metastatic foci than mice injected with CTRL-shRNA-transfected LM2-4175 (FIGS. 5F to H). Similarly, mice injected with BoM-1833 silenced for ROR1 had significantly lower increases in skeletal bioluminescence than did mice injected with equal numbers of CTRL-shRNA-transfected BoM-1833 (FIGS. 5I and J). Moreover, necropsy of animals sacrificed 21 days after intracardiac injection revealed few, if any, detectable metastatic foci in the bone or liver. This was in marked contrast to the extensive metastatic disease detected at each of these sites in animals injected with CTRL-shRNA-transfected BoM-1833 (FIGS. 5J and K).

Example 5

An Anti-ROR1 Antibody Inhibits Cancer Metastasis

Monoclonal antibodies (mAb) specific for the extracellular domain of ROR1 were generated and one, designated D10, could induce rapid down-modulation of surface ROR1 at 37° C. (FIG. 5A). Treatment of MDA-MB-231 with D10 caused ROR1 internalization, as assessed via confocal microscopy (FIG. 5B). This resulted in significant reduction of surface ROR1, as assessed via flow cytometry using a different mAb specific for a distinct, non-cross-blocking epitope of ROR1 (FIG. 5C). Treatment of MDA-MB-231 with D10 also reduced expression of cytoplasmic vimentin (FIG. 5D), which was bound to ROR1 in co-immune-precipitation studies (FIG. 5E). Treatment with D10 also significantly inhibited the migration and invasion capacity of MDA-MB-231 in vitro (FIGS. 5F and G). D10 also could inhibit the migration/invasion capacity of other ROR1+ cancer cell-lines (e.g. HS-578T and BT549 (FIG. 9)).

Figure 5:
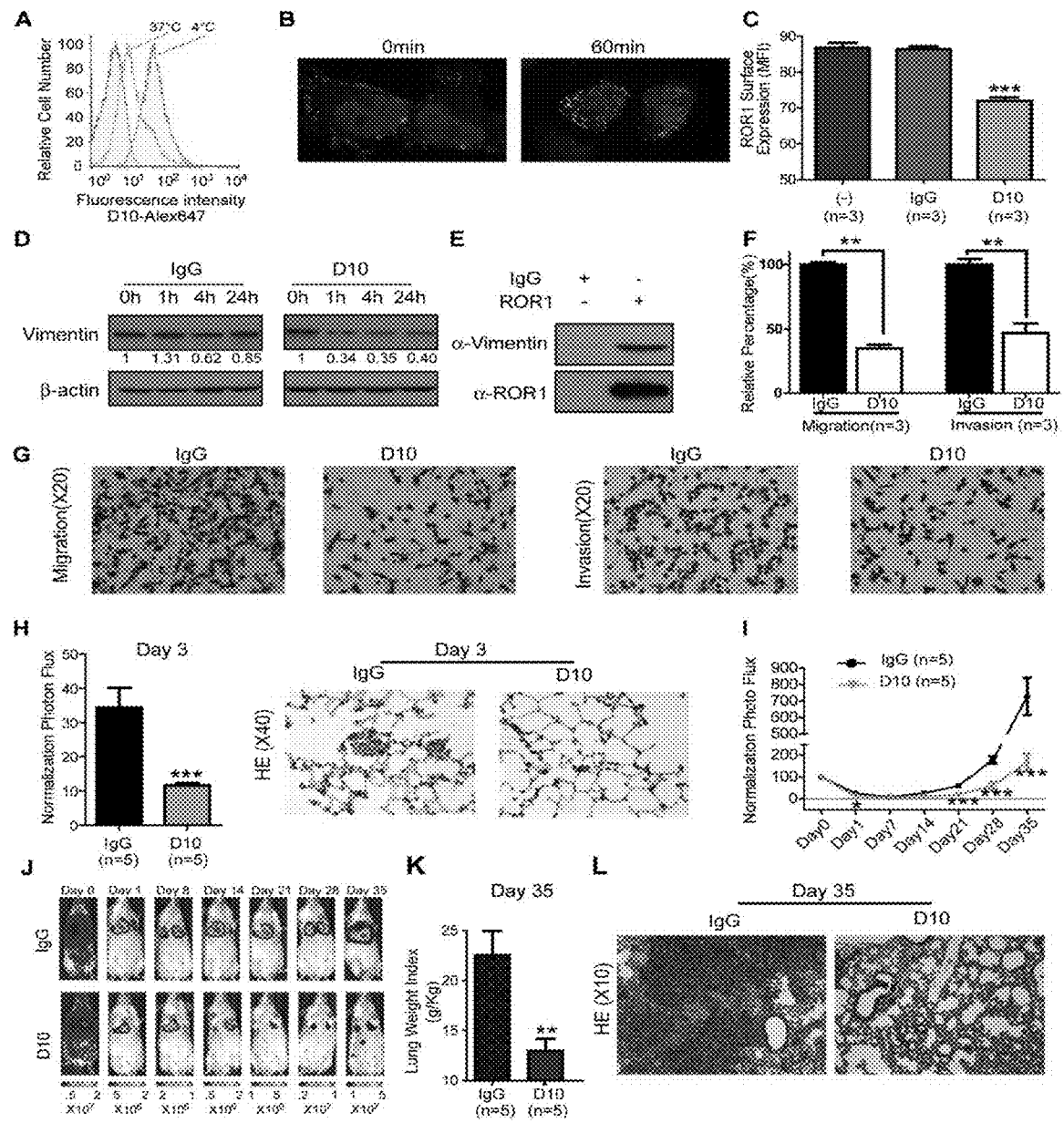
FIG. 5 shows an anti-ROR1 antibody reduces pulmonary metastasis of MDA-MB-231 cell in vivo. (A) D10 mAb causes internalization of ROR1. MDA-MB-231 cells were stained with control-IgG-Alexa647 (red), or D10-Alexa647 for 30 min on ice, and then either kept on ice (blue) or transferred to 37° C. for 1 h (orange) prior to flow cytometry. (B) Confocal microscopy of D10-stained (green) MDA-MB-231 cells before and after 1 h incubation at 37° C. (C) MDA-MB-231 cells were treated with or without (−) control IgG (IgG) or D10 for 24 h prior to staining with a fluorochrome-labeled, non-cross-blocking anti-ROR1, without loss in viability. Mean fluorescence intensity (MFI) of treated cells is shown (***P<0.001 by One-way ANOVA). (D) Representative Immunoblots probed for vimentin (top) or β-actin (bottom) of lysates prepared from MDA-MB-231 before (0 h) or after 1, 4, or 24 h treatment with D10 or control IgG. The ratios of vimentin to β-actin band-intensity are provided below. (E) Immunoprecipitates of MDA-MB-231 cell-lysate using control IgG (IgG) or anti-ROR1 (ROR1) were used for immunoblot analyses probed with antibodies specific for vimentin (top) or ROR1 (bottom). (F) Histograms provide the number of migrated MDA-MB-231 cells that were pre-treated for 1 h with D10 or control IgG.

D10 was assessed for inhibition of invasion and metastasis of MDA-MB-231 injected into the tail vein of RAG–/– γc–/– mice. Following injection of 5×10$^5$ cells, the mice were given an intravenous injection of control IgG or D10 at 5 mg/kg and then sacrificed 3 days later. The ex vivo bioluminescence of the lungs from animals given D10 was significantly lower than that of animals treated with control IgG (FIG. 5H). Moreover, the lungs of animals that received control IgG had multiple metastatic foci, which were not detectable in mice treated with D10. In another experiment, each mouse received an intravenous injection of 5×10$^5$ MDA-MB-231 and then given 3 weekly intravenous injections of control IgG or D10 at 5 mg/kg. Mice treated with D10 developed significantly less pulmonary bioluminescence than mice given control IgG (FIGS. 5, I and J). When sacrificed at day 35, the lungs of mice treated with D10 had significantly lower weight (FIG. 5K) and fewer metastatic foci (FIG. 5L) than the lungs of animals given control IgG. Collectively, these data indicate that D10 can inhibit metastasis in immune-deficient mice.

In conclusion, it is hereby demonstrated that ROR1 can mediate breast cancer metastasis and that therapeutic targeting of ROR1 can retard breast cancer metastasis development. Although embryonic stem cells express detectable ROR1 protein and the loss of ROR1 can enhance heart and skeletal abnormalities in ROR2-deficient mice, major adult tissues rarely express ROR1 protein, except at low levels in the pancreas and adipose tissue, providing the antibodies and methods for their use of the invention with ROR1 cancer specificity Example 6

ROR1 High Affinity Antibodies

Epitope studies were performed on ROR1 antibody D10, described above. A series of chimeric proteins with stretches of human and mouse ROR1 were generated to map the epitope(s) recognized by D10 that can down-modulate ROR1, effect reduction in expression of vimentin, and inhibit cancer-cell migration in vitro (a good surrogate marker of the cancer's capacity to form metastases). The only region of ROR1 that is involved is the Ig-like domain that is on the amino terminus of ROR1. Each construct contains a chimeric Ig-like domain and human CRD and Kringle domain (mouse portion is light, human portion is dark). Only the Ig-like domains are shown here (FIG. 6). These constructs were expressed in free-style 293 cells. Culture media was used immunoblot and purified proteins were used for ELISA. Since the D10 mAb anti-ROR1 recognized human ROR1, but not mouse ROR1, finding which of these constructs could or could not bind could help map the epitope recognized by D10. The results indicate that antibody D10 binds to ROR1 at the C-terminus of the Ig like domain contiguous to the CRD domain (FIG. 7). FIG. 8 shows the mapping of the epitope for ROR1 antibody 4A5. As indicated the 4A5 epitope differs from the D10 epitope.

As described above, an anti-ROR1 antibody, i.e. D10, can inhibit pulmonary metastasis of MDA-MB-231 cell in vivo. The D10 monoclonal antibody facilitates ROR1 receptor internalization (FIG. 9A-9B). The MDA-MB-231 cells were stained with iso-Alex647, or D10-Alex647 for 30 min on ice. The stained cells were then separated into two fractions. One fraction was kept on ice for 1 h and the other fractions were transferred to 37° C. for 15 min, 30 min. Twenty four hours anti-ROR1 antibody D10 treatment decrease ROR1 surface expression in MDA-MB-231 cells (FIG. 9C). ROR1 forms complex with vimentin in breast cancer MDA-MB-231 cells (FIG. 9D). D10 antibody treatment in vitro could decrease vimentin expression (FIG. 9E). Anti-ROR1 antibodies decrease breast cancer migration in vitro. (FIG. 9F). The D10 monoclonal antibody inhibits MDA-MB-231 breast cancer early-stage (day 2) lung metastasis (FIG. 9G). The D10 monoclonal antibody inhibits MDA-MB-231 breast cancer lung metastasis (FIG. 9H). Xenograft mice were intravenously (i.v.) injected with 200 mg anti-ROR1 antibody on day 1, and 100 mg anti-ROR1 antibody on day 3, 7, 14, and 21. The normalized photo fluxes from the lung of MDA-MB-231 bearing mice are shown. Representative mice injected with 5E5 MDA-MB-231 cells are shown in the dorsal position (FIG. 9I). Anti-ROR1 antibody treatment reduced the lung weight of MDA-MB-231-bearing mice (FIG. 9J). Representative pulmonary H&E histology from MDA-MB-231-bearing mice after anti-ROR1 antibody treatment (FIG. 9K). The error bars indicate SEM; *p<0.05, **p<0.01; based on a unpaired two-sided student's t-test.

Constructs depicted in FIG. 6 were used to select high affinity recombinant antibodies. Native western also indicated all three humanized D10-like mAbs target the same epitope as D10 and require amino acid 138 for binding to human ROR1 (FIG. 10). Human and chimeric ROR1-ex constructs were transfected into 293 cells. This allowed for production of recombinant human-mouse chimeric ROR1 proteins that could be size separated in a non-denaturing PAGE gel or SDS PAGE gel for immunoblot analysis with different anti-ROR1 mAb. The results indicate that both D10 and 99961 antibodies bind to the same region, on the C-terminus of Ig-like domain, and that D10 and 99961 can bind to ROR1 under both denatured and native conditions. The full human extracellular domain is provided on the far left lane of either gel (FIG. 11). Antibody 99961 has a 50× higher binding affinity for ROR1 than D10 and reduced leukemic burden more than D10 (FIG. 12). The 99961 antibody was humanized to produce four antibodies designated 99961.1, 99961.2, 99961.3 and 99961.4

Characterization of ROR1 Antibody 99961

Assays were performed to demonstrate specific activity of 99961 against CLL cells in human cord blood reconstituted immune deficient mice. Rag-/-γ-/- mice reconstituted with human cord blood (CB) cells so as to develop a human immune system were injected i.p. with fresh or frozen CLL PBMC. The next day the mice were given 1 mg/kg 99961 or D10 or control mIgG i.v. Seven days later, the CLL PBMC cells from peritoneal cavity were harvested and analyzed by flow cytometry (FIG. 13A). The data indicate that 99961 eliminates >90% of the CLL cells and has no effect on normal human B or T cell development (FIG. 13B, C).

Studies were also performed to demonstrate the specific activity of 99961 in ROR+ primary AML. The results indicate that 99961 decreases the survival of primary colonies and the self renewal capabilities of secondary colonies (FIGS. 14B-14C).

Epitope mapping of the 99961 mAb demonstrated that this epitope is only expressed on various cancers and not on cord blood cell or adult human and progenitor cells or stem cells derived from fetal liver (FIG. 15). It has also been shown that 99961 binds to leukemic cells but does not cross react with normal adult tissues (FIG. 16). The Lymphoma multi-tissue array was from Lifescan Biosciences (LS-SLYCA5) with sections from 40 lymphomas, had 5 cases where Ab9991 bound to the malignant cells. The normal multi-tissue array from Biomax (FDA999) with sections from multiple different normal tissues, showed no specific areas of binding with 99961. The immunohistochemistry was performed using heat induced antigen retrieval with high pH buffer from DAKO (Carpenteria, Calif.) followed by enhancement using biotinyl tyramide amplification (CSA kit from DAKO).

PK studies of 99961 were performed with 1 mg/mouse antibody injected iv to in Rag-/-γ-/- mice. Blood was drawn at different time points and levels of 99961 mAb in plasma were measured by ELISA. The results indicate that the antibody half-life was 11.4 days, volume was 1.18 mL (47 mL/kg) and clearance was 0.072 mL/day (0.12 mL/hr/kg) all consistent with other macromolecules and clinically utilized antibodies (FIGS. 17A-17B).

Example 7

ROR1 Peptide Vaccine

As discussed above, it has been shown that D10 binds at the carboxy terminus of the Ig-like domain that is contiguous to the CRD domain of ROR1. Antibody 4A5 binds to a different epitope in the Ig-like domain and lacks biologic activity. The epitopes of the mAbs were confirmed by chimeric ROR1-ex and site-mutation of the different amino acids between human and mouse ROR1. Peptides corresponding to the extracellular domain of ROR1 where D10, 4A5 and other ROR1 antibodies bind were constructed, A19, R22 and K19. The A19 peptide corresponds to the epitope recognized by the 4A5 mAb; R22 peptide corresponds to the epitope recognized by the D10 mAb, the 99961 mAb (i.e. VATNGKEVVSSTGVLFVKFGPC, SEQ ID NO:25), and the humanized 99961 mAbs; and K19 peptide corresponds to a region in the Kringle domain that is recognized by other mAb specific for ROR1 (FIG. 18). The three peptides were each conjugated at the C-terminus with keyhole limpet hemocyanin (KLH) for immunization in adjuvant complete Freund's adjuvant (CFA) or incomplete Freund's adjuvant (IFA). A cysteine (C) was added at the C-terminus and used for conjugation to KLH with MBS (FIG. 20). The conjugation reaction is depicted in FIG. 19. The conjugated peptides were shown to bind to D10 and 99961 (FIG. 21). C57BL/6 and transgenic mice were immunized with the conjugated peptides. Antibody titers were collected 4 weeks after immunization. R22-KLH vaccine induced the highest titers of anti-ROR1 antisera in either C57BL/6 mice or ROR1-Tg mice (FIG. 28). This experiment was repeated with a 16 amino acid peptide of the D10 epitope, R16 which also induced antibodies that reacted with the human ROR1 protein, although titers were generally lower than those induced by R22-KLH (data not shown).

The anti-ROR1 antibodies induced by R22-KLH vaccine were shown to bind to surface ROR1 present on EW36, JeKo-1, or CLL cells (FIG. 29). For this study, a dilution of antisera from mice immunized with R22-KLH were incubated with the cells for 20 minutes at 4° C. The cells then were washed and then labeled with a goat anti-mouse Ig that was conjugated with a fluorochrome for detection by flow cytometry. The open histograms are the cells stained with the goat anti-mouse Ig without first incubating the cells with the R22-KLH antisera. The shaded histograms are the fluorescence of cells that first were incubated with the anti-R22-KLH antisera. The increase in fluorescence of the cells is due to the mouse anti-ROR1 antibodies bound to the surface, which then were detected with the goat anti-mouse Ig. The pre-immunization antisera of these mice or the antisera of mice immunized with KLH did not bind to these cells (FIG. 29)

The R22-KLH induced antisera was tested for complement dependent cytotoxicity. EW36, Jeko-1, CLL-1 and CLL-2 cells were washed and plated at 25 µl with 5×10$^5$ cells per well in RPMI/10% FBS in round-bottom 96-well plates (Corning Costar). The diluted antisera (250 and 25 µl of a 1:5 dilution of baby rabbit complement were added per well. D10 mAb was used as a positive control. All conditions were performed in triplicate. Plates were incubated for 4 h at 37° C., and cells were immediately quantitated for viability by DiOC6/PI staining and Flow Cytometric Analysis. This study indicates that either D10 or the antisera generated against the R22 peptide could direct complement-mediated lysis of cells bearing human ROR1 (FIG. 30). Cells that did not bear ROR1 were not killed.

The Ig sub-classes of the antibodies induced by R22-KLH were examined. For this, we used an ELISA using plates coated with human ROR1, which then were incubated with diluted antisera, washed and then detected using enzyme-conjugated secondary antibodies specific for each of the IgG subclasses, as indicated on the x axis. The results showed that IgG1, IgG2a, IgG2b and IgG3 were all induced in varying degrees. IgG2a, IgG2b and IgG3 are associated with Th1 profile and IgG1 is associated with Th2 profile. These results indicate that Th1 and Th2 CD4+T helper cells are both activated after vaccination.

R22-KLH was used to immunize C57BL/6 mice as shown in FIG. 31. The first injection of KLH or R22-KLH peptide was in CFA. The second and subsequent injections were in IFA. The animals were bled on the days marked with the purple arrow. Forty four days after the day of the first injection, the C57BL/6 mice were challenged with human-ROR1-expressing CLL cells that originated in a human ROR1-transgenic mouse. This mouse was transgenic for the T-cell-leukemia 1 (TCL1 gene). Both transgenes are under the control of a B-cell specific promoter/enhancer (E-Cμ). This leukemia resembles human CLL and expresses human surface ROR1.

The collected antisera produced a significant reduction in the leukemia cell burden in mice immunized with R22-KLH, but not in mice immunized with KLH. (FIG. 32)

C57BL/6 Mice

R22-KLH was used to immunize C57BL/6 mice according to the schema as shown in FIG. 33. The first injection of KLH or R22-KLH peptide was in CFA. The second and subsequent injections were in IFA. The animals were bled on the days marked with the purple arrow. Forty four days after the day of the first injection, the C57BL/6 mice were challenged with human-ROR1-expressing CLL cells that originated in a human ROR1-transgenic mouse that also was transgenic for the T-cell-leukemia 1 (TCL1 gene). Both transgenes are under the control of a B-cell specific promoter/enhancer (E-Cμ). This leukemia resembles human CLL and expresses human surface ROR1.

Antibody response to human ROR1 observed in mice immunized with R22-KLH at day 42, but not in mice immunized with KLH. All 4 mice immunized with R22-KLH generated high-titer antibodies against human ROR1 as detected via ELISA using plates coated with the extra-cellular domain of recombinant human ROR1 protein. These data indicate that immunization with the R22-KLH peptide can break self-tolerance to ROR1, which is expressed on all B cells of these ROR1-Tg mice. The spleens from the mice given the R22-KLH peptide remained similar to control animals, but the KLH mice had significantly larger spleens (FIG. 34).

Flow cytometry of splenocytes from C57BL/6 mice immunized with either KLH or R22-KLH, using flurochrome-conjugated mAb specific for CD5 or ROR1. The mAb used to stain the cells binds to a non-crossblocking epitope of ROR1 than the antibodies induced by R22-KLH. Note that there are much fewer, if any, leukemia cells in the spleens of mice immunized with the R22-KLH vaccine (FIGS. 39A and 39B).

The total number of leukemia cells found in the spleens of C57BL/6 mice injected with R22-KLH peptide 30 days earlier with 1×10$^5$ human-ROR1+ CLL cells was significantly lower than the spleens of mice injected with KLH. The number of leukemia cells per spleen was derived by multiplying the percent of leukemia cells in the splenocyte populations (as assessed via flow cytometry) by the number of splenocytes harvested from the spleen (FIG. 34).

The number of CD8+ cells in the spleens of mice immunized with KLH or R22-KLH was determined by flow cytometry. Following immunization with R22-KLH there were dramatic increases in CD8 T cells, which were not increased in mice immunized with KLH. The bottom row indicate the absolute number of CD8 T cells harvested from the spleens of mice on day 75 (FIGS. 37A and 37B)

C57BL/6 ROR1 Transgenic Mice

Transgenic mice were injected with either R22-KLH or KLH as shown in FIG. 38. The mice are transgenic for human ROR1 under a B-cell specific promoter/enhancer (E-Cμ). The first injection of KLH or R22-KLH peptide was in CFA. The second and subsequent injections were in IFA. The animals were bled on the days marked with the purple arrow. Forty four days after the day of the first injection, the C57BL/6 mice were challenged with human-ROR1-expressing CLL cells that originated in a ROR1-Tg mouse that also was transgenic for the T-cell-leukemia 1 (TCL1 gene). Both transgenes are under the control of a B-cell specific promoter/enhancer (E-Cμ). Hence these ROR1-Tg mice have B cells that express human ROR1. The results demonstrate that the R22-KLH peptide can induce anti-ROR1protective immunity in mice that express ROR1 and hence break self-tolerance.

Antibody response to human ROR1 was observed in ROR1-Tg mice immunized with R22-KLH at day 42, but not in mice immunized with KLH. All 4 mice immunized with R22-KLH generated high-titer antibodies against human ROR1 as detected via ELISA using plates coated with the extra-cellular domain of recombinant human ROR1 protein. Further analysis by flow cytometry demonstrated that there are fewer, if any, leukemia cells in the spleens of mice immunized with the R22-KLH vaccine than mice immunized with KLH (FIG. 40). FACs analysis also showed that ROR1 was down modulated in the mice immunized with R22-KLH but not the mice immunized with KLH. Spleens from mice immunized with R22-KLH had significantly fewer leukemia cells compared to mice immunized with KLH. As with the C57BL/6 mice, immunization with R22-peptide-KLH led to dramatic increases in CD8 T cells, which were not increased in mice immunized with KLH (FIGS. 39A and 39B). Similar results were seen with CD4+ T cells (FIGS. 43A and 43B) and CD3+ T cells (FIGS. 42A and 42B).

BALB/c Mice

BALB/c mice were immunized with KLH or R22-KLH as shown in FIG. 22. For this, KLH or KLH-conjugated peptide each was formed into an emulsion with adjuvant (CFA or IFA). CFA was used for the first immunization and IFA was used for the subsequent boost. The bleeding and peptide injection days are indicated.

R22-KLH induced anti-ROR1 antibody levels were determined by ELISA. Purified ROR1-extacellular domain was coated to 96-well plate and incubated anti-sera with indicated dilution times from individual bleeding days. ELISA results indicated that the concentrations of anti-ROR1 antibodies were induced in immunized BALB/c mice over time. The sera from these animals collected prior to immunization did not react with the ROR1 protein, even at low serum dilution.

Immunoblot analysis also indicated that anti-ROR1 antibodies generated by R22-KLH immunization of BALB/c mice produced anti-ROR1 antibodies that had the same epitope specificity as D10 (FIG. 23). In addition, it appears that the antisera also react with the mouse protein.

FACS analysis was confirmed the binding of anti-sera from R22-KLH immunized BALB/c mice to ROR1 on the surface of cells.

Transgenic Mice II

Transgenic mice were immunized with either KLH or R22-KLH as shown in FIG. 24. The KLH conjugated peptide was mixed with adjuvant (CFA or IFA). CFA was used for the first immunization and IFA was used for the following boost. ELISA results indicated that the concentrations of anti-ROR1 antibodies were induced in R22-KLH immunized ROR1 transgenic mice over time. FACS analysis confirmed the binding of anti-sera from R22-KLH immunized ROR1 transgenic mice to ROR1 on the surface of cells.

Antisera from R22-KLH immunized mice were examined for ROR1 receptor internalization ability. MDA-MB-231 cells were incubated with anti-sera from transgenic mice at 4° C. or 37° C. for 1 h and then stained with isotype-Alexa647, or 4A5-Alexa647 for 30 min on ice prior to FACS analysis of ROR1 expression. The results showed that Anti-ROR1 sera from transgenic mice immunized with R22-KLH induced ROR1 receptor internalization (FIG. 25)

Antisera from R22-KLH immunized mice were examined to determine their affect in breast cancer migration. Migrated cells were observed under 10× magnification after 1 h of anti-sera treatment and then 16 h of incubation at 37° C. Results are means±s.e.m. n=3. **p<0.01. The results indicated that Anti-ROR1 sera from transgenic mice could decrease breast cancer migration in vitro (FIGS. 26A-26B).

Chimeric Antigen Receptors (CAR)

T cells can be transduced with chimeric antigen receptors (CAR) specific for surface antigen or a target cell population, allowing the CAR-bearing T cells to specific kill cells bearing the target antigen. We hypothesize that the epitope (s) of ROR1 recognized by a CAR might influence the capacity of CAR-expressing T cells to kill CLL cells in vitro or in vivo. We are collaborating with Drs. Cooper and Wierda in the CRC for CRC038 (Core D). Dr. Cooper has conducted seminal studies, evaluating the safety and clinical activity of autologous T cells genetically modified to express CAR specific for CD19 or CD20 (e.g. BB-IND1141, clinical Trials.gov identifier: NCT00182650). He has advanced the Sleeping Beauty (SB) system, which uses a DNA salmonid transposon, to transfect T cells with vectors encoding the CAR. This system employs a transposon CAR expression cassette flanked by terminal inverted repeats (IR), which bind a SB transposase encoded by a co-transfected vector. The SB transposase excises a precise DNA sequence flanked by the IRs, allowing for insertion of the transposon into any of—z200 million TA sites in the mammalian genome. This system allows for ex vivo transfection of T-cells, which subsequently are propagated on artificial antigen-presenting cells (aAPC) consisting of genetically-modified K562 cells that lack MHC class I antigens, but have been genetically-modified to express the target antigen (e.g. ROR1 for the anti-ROR1 CAR), along with 4-1BBL (CD137) and a cell-surface bound form of human interleukin-15 (e.g. IL-15-Fc). Blood—derived T cells expressing the specific CAR are stimulated to produce IL-2 and proliferate when co-cultured on such aAPC.

We generated a 4A5-CAR by inserting the gene encoding the 4A5 scFv upstream of gene segments encoding an IgG4 CH domain, the TM domain of CD28, the cytoplasmic domains of CD28 (CD28Cyto) and CD3-zeta chain, CD247. This generated 4A5-CAR, which, except for the 4A5 scFv segment, is identical to the CD19– specific CAR used by Dr. Cooper in clinical studies. JURKAT transfected to express 4A5-CAR, but not JURKAT or mock-transfected JURKAT, could bind Alexa-647-conjugated Ex-ROR1 by flow cytometry. We generated an expression vector in which 4A5-CAR was flanked by the IRs necessary for transposon-facilitated transduction of activated T cells using the SB System. We already have generated GMP-quality human ROR1-expressing aAPC for planned clinical trials, designated hROR1+-K562 aAPC, which can be used in our studies to induce proliferation of T cells that express functional anti-ROR1 CAR in vitro.

We propose to generate CAR that binds distinct epitopes of ROR1 recognized by 4A5 or D10. Each construct will be evaluated for its capacity to encode a surface receptor on transfected cells that is capable of binding fluorescence-tagged ex-ROR1 via flow cytometry and validated by nucleic acid sequence analysis. Using the SB system, each validated construct will be used for transposon-facilitated transfection of activated T cells initially induced to proliferate via CD3/CD28 co-stimulation. Transduced T-cells will be monitored for expression of ROR1-specific CAR by flow cytometry and expanded further using hROR1+-K562 aAPC. Following expansion, the T cells will again be evaluated for expression levels of the ROR1-specific CAR and cell viability prior to measuring their relative capacity to kill ROR1+ CLL cells or ROR1-transduced target cells (e.g. P815-hROR1, CHO-hROR1), but not atypical ROR1-negative CLL cells or mock transduced ROR1-negative target cells (P815, CHO) at varying effector:target cell ratios, using flow cytometric assays developed in our laboratory. An additional specificity control will include addition of exogenous ex-ROR1 to compete with surface ROR1 for binding to ROR1-specific CAR. Reproducible differences between T cells that express similar levels of different ROR1-specific CAR of two-fold or greater will be considered biologically significant. These in vitro studies will precede in vivo studies performed using immune deficient mice engrafted with luciferase-expressing CLL cells. The ROR1-specific CAR providing T cells the greatest capacity to kill ROR1+ CLL cells specifically will be used in CRC038 under IND BB-IND1141.

What is claimed is:

1. A polypeptide comprising a single-chain variable fragment (scFv) that specifically binds a ROR1 protein and comprises a heavy chain variable region and a light chain variable region, wherein the heavy chain variable region comprises the sequences set forth in SEQ ID NO:27, SEQ ID NO:28, and SEQ ID NO:29; and wherein the light chain variable region comprises the sequences set forth in SEQ ID NO:30, SEQ ID NO:31, and SEQ ID NO:32.

2. The polypeptide of claim 1, wherein the scFv binds to amino acids 130-160 of hROR-1.

3. The polypeptide of claim 2, wherein the scFv requires that hROR1 amino acid 138 is glutamic acid for binding to hROR-1.

4. The polypeptide of claim 1, wherein the heavy chain variable region comprises the amino acid sequence set forth in SEQ ID NO: 5, and wherein the light chain variable region comprises the amino acid sequence set forth in SEQ ID NO: 7.

5. The polypeptide of claim 1, wherein the scFv is humanized.

6. The polypeptide of claim 1, wherein the scFv forms a part of a fusion protein.

7. The polypeptide of claim 6, wherein the fusion protein is a multi-specific antibody.

8. The polypeptide of claim 6, wherein the fusion protein is a chimeric antigen receptor.

9. The polypeptide of claim 8, wherein the chimeric antigen receptor is expressed on a T cell.

10. A method of treating an ROR-1 expressing cancer in a subject, the method comprising administering to the subject a composition comprising a single-chain variable fragment (scFv) that specifically binds ROR1 protein, wherein the scFv comprises a heavy chain variable region and a light chain variable region, wherein the heavy chain variable region comprises the sequences set forth in SEQ ID NO:27, SEQ ID NO:28, and SEQ ID NO:29; and wherein the light chain variable region comprises the sequences set forth in SEQ ID NO:30, SEQ ID NO:31, and SEQ ID NO:32.

11. The method of claim 10, wherein the cancer is selected from the group consisting of: B cell leukemia, lymphoma, chronic lymphocytic leukemia (CLL), acute myelogenous leukemia (AML), B cell lymphoblastic acute lymphoblastic leukemia (B-ALL), T cell lymphoblastic acute lymphoblastic leukemia (T-ALL), ovarian cancer, colon cancer, lung cancer, skin cancer, pancreatic cancer, testicular cancer, bladder cancer, uterine cancer, prostate cancer, adrenal cancer, and combinations thereof.

12. The method of claim 10, wherein the scFv binds to amino acids 130-160 of hROR-1.

13. The method of claim 10, wherein the scFv requires that hROR1 amino acid 138 is glutamic acid for binding to hROR-1.

14. The method of claim 10, wherein the heavy chain variable region comprises the amino acid sequence set forth in SEQ ID NO: 5, and wherein the light chain variable region comprises the amino acid sequence set forth in SEQ ID NO: 7.

15. The method of claim 10, wherein the composition comprises a therapeutic agent.

16. The method of claim 15, wherein the therapeutic agent is conjugated to the scFv.

17. The method of claim 10, wherein the composition comprises a fusion protein comprising the scFv.

18. The method of claim 17, wherein the fusion protein is a chimeric antigen receptor.

19. The method of claim 18, wherein the chimeric antigen receptor is expressed on a T cell.

20. The method of claim 10, wherein the scFv is humanized.

* * * * *